US010005832B2

(12) United States Patent
Yoshida et al.

(10) Patent No.: US 10,005,832 B2
(45) Date of Patent: Jun. 26, 2018

(54) METHOD FOR TREATING A DISEASE ORIGINATED FROM RECEPTOR ACTIVATION BY EREG AND TGFα

(71) Applicant: Chugai Seiyaku Kabushiki Kaisha, Tokyo (JP)

(72) Inventors: Kenji Yoshida, Tokyo (JP); Hirotaka Ito, Tokyo (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days. days.

(21) Appl. No.: 14/873,861

(22) Filed: Oct. 2, 2015

(65) Prior Publication Data

US 2016/0017028 A1  Jan. 21, 2016

Related U.S. Application Data

(63) Continuation of application No. 13/375,050, filed as application No. PCT/JP2010/059008 on May 27, 2010, now abandoned.

(30) Foreign Application Priority Data

May 29, 2009 (JP) ................................. 2009-131331

(51) Int. Cl.
| | |
|---|---|
| *C07K 16/22* | (2006.01) |
| *A61K 39/395* | (2006.01) |
| *A61K 45/06* | (2006.01) |
| *G01N 33/50* | (2006.01) |
| *A61K 39/00* | (2006.01) |

(52) U.S. Cl.
CPC .......... *C07K 16/22* (2013.01); *A61K 39/3955* (2013.01); *A61K 45/06* (2013.01); *G01N 33/5011* (2013.01); *A61K 2039/507* (2013.01); *C07K 2317/24* (2013.01); *C07K 2317/31* (2013.01); *C07K 2317/565* (2013.01); *C07K 2317/73* (2013.01); *C07K 2317/76* (2013.01); *G01N 2333/4703* (2013.01); *G01N 2333/485* (2013.01)

(58) Field of Classification Search
None
See application file for complete search history.

(56) References Cited

U.S. PATENT DOCUMENTS

| | | | |
|---|---|---|---|
| 5,190,858 A | 3/1993 | Sorvillo et al. | |
| 5,783,417 A | 7/1998 | Komurasaki et al. | |
| 5,994,511 A | 11/1999 | Lowman et al. | |
| 6,172,213 B1 | 1/2001 | Lowman et al. | |
| 6,852,318 B1 | 2/2005 | Varner | |
| 6,949,245 B1 | 9/2005 | Sliwkowski | |
| 7,435,590 B2 | 10/2008 | Komurasaki | |
| 8,084,584 B2 | 12/2011 | Sugo et al. | |
| 9,017,684 B2 | 4/2015 | Aburatani et al. | |
| 2002/0160014 A1 | 10/2002 | Rodriguez et al. | |
| 2003/0105000 A1 | 6/2003 | Pero et al. | |
| 2003/0115614 A1 | 6/2003 | Kanda et al. | |
| 2004/0044187 A1 | 3/2004 | Sato et al. | |
| 2004/0197328 A1 | 10/2004 | Young et al. | |
| 2004/0236078 A1 | 11/2004 | Carter et al. | |
| 2005/0171339 A1 | 8/2005 | Sugo et al. | |
| 2006/0154333 A1 | 7/2006 | Pienkos et al. | |
| 2006/0188497 A1 | 8/2006 | Rodriguez et al. | |
| 2006/0252105 A1 | 11/2006 | Komurasaki | |
| 2008/0166756 A1 | 7/2008 | Tsuchiya et al. | |
| 2009/0061485 A1 | 3/2009 | Tsuchiya et al. | |
| 2009/0324491 A1 | 12/2009 | Aburatani et al. | |
| 2010/0092490 A1 | 4/2010 | Uenaka et al. | |
| 2010/0310463 A1 | 12/2010 | Cicortas Gunnarsson et al. | |
| 2010/0310464 A1 | 12/2010 | Cicortas Gunnarsson et al. | |
| 2012/0141501 A1 | 6/2012 | Yoshida et al. | |
| 2014/0073005 A1 | 3/2014 | Umana et al. | |
| 2014/0199294 A1 | 7/2014 | Mimoto et al. | |
| 2015/0110793 A1 | 4/2015 | Shiraiwa et al. | |
| 2015/0344570 A1 | 12/2015 | Igawa et al. | |
| 2016/0159904 A1 | 6/2016 | Yamazaki et al. | |
| 2017/0129950 A1 | 5/2017 | Shiraiwa et al. | |

FOREIGN PATENT DOCUMENTS

| | | |
|---|---|---|
| CA | 2 665 528 A1 | 4/2008 |
| CN | 1761682 A | 4/2006 |
| CN | 101594883 A | 12/2009 |
| CN | 104136610 A | 11/2014 |
| EP | 1 069 185 B1 | 1/2001 |
| EP | 1 331 266 A1 | 7/2003 |
| EP | 1 350 521 A1 | 10/2003 |
| EP | 1 607 404 A1 | 12/2005 |
| EP | 1 829 962 A1 | 9/2007 |
| EP | 2 070 548 A1 | 6/2009 |
| EP | 2 436 397 A1 | 4/2012 |
| EP | 2 728 002 A1 | 5/2014 |
| EP | 2 799 543 A1 | 11/2014 |

(Continued)

OTHER PUBLICATIONS

Jonker et al, new England Journal of Medicine, 2007, vol. 357, No. 20, pp. 2040-2048.*
Imanishi et al, Journal of the National Cancer Institute, 1989, vol. 81, pp. 220-223.*
Peggs et al reference, Clinical and Experimental Immunology, 2009; vol. 157, pp. 9-19.*
Spano et al, Annals of Oncology; 2005, vol. 16, pp. 189-194.*
Beidler et al, Journal of Pharmacology and Experimental Therapeutics, 2014; vol. 349, pp. 330-343.*
Baba, I., et al., "Involvement of Deregulated Epigregulin Expression in Tumorgenesis in Vivo through Activated Ki-Ras Signaling Pathway in Human Colon Cancer Cells," *Cancer Research* 60:6886-6889, American Association for Cancer Research, United States (2000).

(Continued)

*Primary Examiner* — Bridget E Bunner
*Assistant Examiner* — Fozia Hamud
(74) *Attorney, Agent, or Firm* — Nixon & Vanderhye P.C.

(57) ABSTRACT

The present inventors identified inhibition of a combination of EGFR ligands that serve as targets for inhibition of cancer cell proliferation. More specifically, EREG antagonists and TGFα antagonists were found to be useful as inhibitors of cell growth. The present invention relates to pharmaceutical compositions containing EGF family ligand antagonists as components.

3 Claims, 12 Drawing Sheets

(56) References Cited

FOREIGN PATENT DOCUMENTS

| | | |
|---|---|---|
| JP | 2003-503366 A | 1/2003 |
| JP | 2005-519023 A | 6/2005 |
| JP | 2006-516893 A | 7/2006 |
| JP | 2008-527978 A | 7/2008 |
| KR | 10-2005-0108389 | 11/2005 |
| RU | 2270029 C2 | 9/2003 |
| RU | 2 312 109 C2 | 12/2007 |
| WO | WO 94/29340 A1 | 12/1994 |
| WO | WO 99/51743 A1 | 10/1999 |
| WO | WO 01/00245 A2 | 1/2001 |
| WO | WO 02/31140 A1 | 4/2002 |
| WO | WO 02/45747 A1 | 6/2002 |
| WO | WO 02/079255 A1 | 10/2002 |
| WO | WO 03/057881 A1 | 7/2003 |
| WO | WO 2004/003019 A2 | 1/2004 |
| WO | WO 2004/065540 A2 | 8/2004 |
| WO | WO 2004/081047 A1 | 9/2004 |
| WO | WO 2005/068503 A2 | 7/2005 |
| WO | WO 2005/076979 A2 | 8/2005 |
| WO | WO 2006/029497 A | 3/2006 |
| WO | WO 2006/067913 A1 | 6/2006 |
| WO | WO 2007/015578 A1 | 2/2007 |
| WO | WO 2007/092932 A2 | 8/2007 |
| WO | WO 2008/047723 A1 | 4/2008 |
| WO | WO 2010/137654 A1 | 12/2010 |
| WO | WO 2010/142952 A2 | 12/2010 |
| WO | WO 2010/142990 A1 | 12/2010 |
| WO | WO 2013/002362 A1 | 1/2013 |
| WO | WO 2013/100120 A1 | 7/2013 |
| WO | WO 2014/208482 A1 | 12/2014 |

OTHER PUBLICATIONS

Dean. C., et al., "Immunotherapy With Antibodies to the EGF Receptor," *Int. J. Cancer Supplement* 8:103-107, Wiley-Liss, Inc., United States (1994).

Force, T., et al., "Molecular mechanisms of cardiotoxicity of tyrosine kinase inhibition," *Nature Reviews Cancer* 7:332-334, Nature Publishing Group, England (2007).

Higashiyama, S., et al., "Membrane-anchored growth factors, the epidermal growth factor family: Beyond receptor ligands," *Cancer Sci.* 99(2):214-220, Japanese Cancer Association, Japan (2008).

Ito, M., et al., "Expression of several growth factors and their receptor genes in human colon carcinomas," *Virchows Archiv B Cell Pathol.* 59:173-178, Springer-Verlag, Germany (1990).

Johnson, G.R., et al., "Autocrine Action of Amphiregulin in a Colon Carcinoma Cell Line and Immunocytochemical Localization of Amphiregulin in Human Colon," *J. Cell Biol.* 118(3):741-751, The Rockefeller University Press, United States (1992).

Lacouture, M.E., "Mechanisms of cutaneous toxicities to EGFR inhibitors," *Nature Reviews Cancer* 6:803-812, Nature Publishing Group, England (2006).

Lu, Y., et al., "Immunogene Therapy of Tumors with Vaccine Based on Xenogenic Epidermal Growth Factor Receptor," *J. Immunol.* 170:3162-3170, The American Association of Immunologists, Inc., United States (2003).

Modjtajedi, H., et al., "Anti-EGFR Monoclonal Antibodies Which Act As EGF, TGFα, HB-EGF and BTC Antagonists Block the Binding of Epiregulin to EGFR-Expressing Tumors," *Int. J. Cancer* 75:310-316, Wiley-Liss, Inc., United States (1998).

Qian, J.F., et al., "Human transforming growth factor alpha: sequence analysis of the 4.5-kb and 1.6-kb mRNA species," *Gene* 132:291-296, Elsevier Science Publishhers B.V., Netherlands (1993).

Schneider, M.R. and Wolf, E., "The Epidermal Growth Factor Receptor Ligands at a Glance," *J. Cell Physiol.* 218:460-466, Wiley-Liss, Inc., United States (2008).

Seth, D., et al., "Complex post-transcriptional regulation of EGF-receptor expression by EGF and TGF-α in human prostate cancer cells," *Br. J. Cancer* 80(5/6):657-669, Cancer Research Campaign, England (1999).

Tejpar, S., et al., "Magnesium wasting associated with epidermal-growth-factor receptor-targeting antibodies in colorectal cancer: a prospective study," *Lancet Oncol.* 8:387-394, Lancet Publishing Group, England (2007).

Tiel Groenestege, W.M., et al., "Impaired basolateral sorting of pro-EGF causes isolated recessive renal hypomagnesemia," *J. Clin. Invest.* 117(8):2260-2267, American Society for Clinical Investigation, United States (2007).

Willmarth, N.E., and Ethier, S.P., "Autocrine and Juxtacrine Effects of Amphiregulin on the Proliferative, Invasive, and Migratory Properties of Normal and Neoplastic Human Mammary Epithelial Cells," *J. Biol. Chem.* 281(49):37728-37737, The American Society for Biochemistry and Molecular Biology, Inc., United States (2006).

Wilson, K.J., et al., "Functional selectivity of EGF family peptide growth factors: Implications for cancer," *Pharmacol. Ther.* 122(1):1-8, Elsevier B.V., Netherlands (2009).

Unverified English language translation of WO 2008/047723 A1, published Jun. 24, 2008.

International Search Report for International Application No. PCT/JP2010/059008, Japanese Patent Office, dated Jul. 6, 2010.

Nicholson, B.E. et al., "Profiling the Evolution of Human Metastatic Bladder Cancer," *Cancer Res.* 64:7813-7821, American Association for Cancer Research, United States (2004).

Beckman, R.A., et al., "Antibody Constructs in Cancer Therapy Protein Engineering Strategies to Improve Exposure in Solid Tumors," *Cancer* 109:170-179, American Cancer Society, United States (2007).

Brorson, K., et al., "Mutational Analysis of Avidity and Fine Specificity of Anti-Levan Antibodies," *J. Immunol.* 163:6694-6701, The American Association of Immunologists, United States (1999).

Brummell, D.A., et al., "Probing the Combining Site of an Anti-Carbohydrate Antibody by Saturation-Mutagenesis: Role of the Heavy-Chain CDR3 Residues," *Biochemistry* 32:1180-1187, American Chemical Society, United States (1993) (Abstract Only).

Burks, E.A., et al.,"In vitro Scanning Saturation Mutagenesis of an Antibody Binding Pocket," *Proc. Natl. Acad. Sci. U.S.A.* 94:412-417, National Academy of Sciences, United States (1997).

Casset, F., et al., "A Peptide Mimetic of an Anti-CD4 Monoclonal Antibody by Rational Design," *Biochem. Biophys. Res. Commun.* 307:198-205, Academic Press, United States (2003).

Céspedes, M.V., et al., "Mouse Models in Oncogenesis and Cancer Therapy," *Clin. Transl. Oncol.* 8:318-329, Springer Italia, Italy (2006).

Chen, Y., et al., "Selection and Analysis of an Optimized Anti-VEGF Antibody: Crystal Structure of an Affinity-Matured Fab in Complex with Antigen," *J. Mol. Bio.* 293:865-881, Academic Press, United States (1999).

Colman, P.M., "Effects of Amino Acid Sequence Changes on Antibody-Antigen Interactions," *Res. Immunol.* 145:33-36, Elsevier Science Publishers B.V., Netherlands (1994).

De Pascalis, R., et al., "Grafting of "Abbreviated" Complementarity-Determining Regions Containing Specificity-Determining Residues Essential for Ligand Contact to Engineer a Less Immunogenic Humanized Monoclonal Antibody," *J. Immunol.* 169:3076-3084, The American Association of Immunologists, Inc., United States (2002).

Dennis, C., "Off by a Whisker," *Nature* 442:739-741, Nature Publishing Group, England (2006).

Friedberg, J.W., "Unique Toxicities and Resistance Mechanisms Associated with Monoclonal Antibody Therapy," *Hematology* 2005:329-334, American Society of Hematology, United States (2005).

Fujimori, K., et al., "A Modeling Analysis of Monoclonal Antibody Percolation Through Tumors: A Binding-Site Barrier," *J. Nuc. Med.* 31:1191-1198, Society of Nuclear Medicine, United States (1990).

Hanai, N., "Antibody Modification and Transgenic Mice," *Biotherapy* 17:415-421, Kluwer Academic Publishers, Netherlands (2003).

Holm, P., et al., "Functional Mapping and Single Chain Construction of the Anti-Cytokeratin 8 Monoclonal Antibody TS1," *Mol. Immunol.* 44:1075-1084, Elsevier Ltd., England (2007).

(56) References Cited

OTHER PUBLICATIONS

Jang, Y.-J., et al., "The Structural Basis for DNA Binding by an Anti-DNA Autoantibody," *Molec. Immunol.* 35:1207-1217, Elsevier Science Ltd., England (1998).

Kobayashi, H., et al., "Tryptophan H33 Plays an Important Role in Pyrimidine (6-4) Pyrimidone Photoproduct Binding by a High-Affinity Antibody," *Protein Eng.* 12:879-884, Oxford University Press, England (1999).

Koo, B.-H. and Kim, D.-S., "Factor Xa Induces Mitogenesis of Vascular Smooth Muscle Cells via Autocrine Production of Epiregulin," *J. Biol. Chem.* 278:52578-52586, The American Society for Biochemistry and Molecular Biology, Inc., United States (2003).

Kumar, S., et al., "Molecular Cloning and Expression of the Fabs of Human Autoantibodies in *Escherichia coli,*" *J. Biol. Chem.* 275:35129-35136, The American Society for Biochemistry and Molecular Biology, Inc., United States (2000).

Kuntz, E., et al., "Effect of Epiregulin on Pancreatic Beta Cell Growth and Insulin Secretion," *Growth Factors* 23:285-293 (2005) (Abstract Only).

MacCallum, R.M., et al., "Antibody-Antigen Interactions: Contact Analysis and Binding Site Topography," *J. Mol. Biol.* 262:732-745, Academic Press Limited, United States (1996).

Minn, A.J., et al., "Genes that Mediate Breast Cancer Metastasis to Lung," *Nature* 436:518-524, Nature Publishing Group, England (2005).

R&D Systems, Inc., "Anti-Human Epiregulin Antibody," *R&D Systems Catalog*, Catalog No. AF1195, 2 pages, Minneapolis, MN (2003).

R&D Systems, Inc., "Monoclonal Anti-Human Epiregulin Antibody," *R&D Systems Catalog*, Catalog No. MAB1425, 1 page, Minneapolis, MN (2003).

Rudikoff, S., et al., "Single Amino Acid Substitution Altering Antigen-Binding Specificity," *Proc. Natl. Acad. Sci. U.S.A.* 79:1979-1983, National Academy of Sciences, United States (1982).

Rudnick, S.I., and Adams, G.P., "Affinity and Avidity in Antibody-Based Tumor Targeting," *Can. Biother. & Radiopharm.* 24:155-161, Mary Ann Liebert, Inc., United States (2009).

Shirakata, Y., et al., "Epiregulin, a Novel Member of the Epidermal Growth Factor Family, is an Autocrine Growth Factor in Normal Human Keratinocytes," *J. Biol. Chem.* 275:5748-5753, American Society for Biochemistry and Molecular Biology, United States (2000).

Shirasawa, S., et al., "Dermatitis Due to Epiregulin Deficiency and a Critical Role of Epiregulin in Immune-Related Responses of Keratinocyte and Macrophage," *Proc. Natl. Acad. Sci. U.S.A.* 101:13921-13926, National Academy of Sciences, United States (2004).

Smith-Gill, S.J., et al., "Contributions of Immunoglobulin Heavy and Light Chains to Antibody Specificity for Lysozyme and Two Haptens," *J. Immunol.* 139:4135-4144, The American Association of Immunologists, United States (1987).

Song, M.-K., et al., "Light Chain of Natural Antibody Plays a Dominant Role in Protein Antigen Binding," *Biochem. Biophys. Res. Commun.* 268:390-394, Academic Press, United States (2000).

Takahashi, M., et al., "Epiregulin as a Major Autocrine/Paracrine Factor Released From ERK- and p38MAPK-Activated Vascular Smooth Muscle Cells," *Circulation* 108:2524-2529, American Heart Association, Inc., United States (2003).

Talmadge, J.E., et al., "Murine Models to Evaluate Novel and Conventional Therapeutic Strategies for Cancer," *Am. J. Pathol.* 170:793-804, American Society for Investigative Pathology, United States (2007).

Thurber, G.M., et al., "Antibody Tumor Penetration: Transport Opposed by Systemic and Antigen-Mediated Clearance," *Adv. Drug Deliv. Rev.* 60:1421-1434, Elsevier B.V., Netherlands (2008).

Toyoda, H., et al., "Distribution of mRNA for Human Epiregulin, a Differentially Expressed Member of the Epidermal Growth Factor Family," *Biochem. J.* 326:69-75, Portland Press, England (1997).

Toyoda, H., et al., "Epiregulin. A Novel Epidermal Growth Factor with Mitogenic Activity for Rat Primary Hepatocytes," *J. Biol. Chem.* 270:7495-7500, American Society for Biochemistry and Molecular Biology, United States (1995).

Vajdos, F.F., et al., "Comprehensive Functional Maps of the Antigen-binding Site of an Anti-ErbB2 Antibody Obtained with Shotgun Scanning Mutagenesis," *J. Mol. Biol.* 320:415-428, Elsevier Science Ltd., England (2002).

Voskoglou-Nomikos, T., et al., "Clinical Predictive Value of the in Vitro Cell Line, Human Xenograft, and Mouse Allograft Preclinical Cancer Models," *Clin. Can. Res.* 9:4227-4239, American Association for Cancer Research, United States (2003).

Ward, E.S., et al., "Binding Activities of a Repertoire of Single Immunoglobulin Variable Domains Secreted from *Escherichia coli,*" *Nature* 341:544-546, Nature Publishing Group, England (1989).

Wu, H., et al., "Humanization of a Murine Monoclonal Antibody by Simultaneous Optimization of Framework and CDR Residues," *J. Mol. Biol.* 294:151-162, Academic Press, United States (1999).

Zhu, Z., et al., "Epiregulin is Up-Regulated in Pancreatic Cancer and Stimulates Pancreatic Cancer Cell Growth," *Biochem. Biophys. Res. Commun.* 273:1019-1024, Academic Press, United States (2000).

International Search Report for International Patent Application No. PCT/JP2007/069988, Japanese Patent Office, Japan, dated Nov. 20, 2007 (5 pages) (Not a Corresponding Application).

International Preliminary Report on Patentability of the International Searching Authority for International Application No. PCT/JP2007/069988, dated Apr. 28, 2009, The International Bureau of WIPO, Switzerland (Not a Corresponding Application).

International Preliminary Report on Patentability of the International Searching Authority for International Application No. PCT/JP2010/059008, dated Jul. 6, 2010, The International Bureau of WIPO, Switzerland.

Supplementary European Search Report in European Patent Application No. 07 82 9724, dated Jul. 29, 2010, European Patent Office, Munich, Germany (Not a Corresponding Application).

Office Action dated Sep. 6, 2012, in U.S. Appl. No. 12/444,916, Aburatani, H., et al., Int'l filed Oct. 12, 2007, U.S. Patent and Trademark Office, Alexandria, VA.

Office Action dated Jan. 18, 2012, in U.S. Appl. No. 12/444,916, Aburatani, H., et al., Int'l filed Oct. 12, 2007, U.S. Patent and Trademark Office, Alexandria, VA.

Restriction Requirement in U.S. Appl. No. 12/444,916, Aburatani, H., et al., Int'l filed Oct. 12, 2007, dated May 25, 2011, U.S. Patent and Trademark Office, Alexandria, VA.

Response to Restriction Requirement filed on Nov. 22, 2011, in U.S. Appl. No. 12/444,916, Aburatani, H., et al., Int'l filed Oct. 12, 2007, U.S. Patent and Trademark Office, Alexandria, VA.

Amendment and Reply to Office Action filed on Jun. 28, 2012, in U.S. Appl. No. 12/444,916, inventors Aburatani, H., et al., Int'l filed Oct. 12, 2007, U.S. Patent and Trademark Office, Alexandria, VA.

Unverified English language translation of Asano, R., et al., "The Advance on the Antibody Therapy—the Expectation to the Clinical Application," *Igaku no Ayumi* 211:723-727, Maruzen Co Ltd., Tokyo, Japan (2004).

Unverified English language translation of Sunanaga, N., et al., "Haigan ni okeru Epiregulin Idenshi no Hatsugen ni tsuite no Kento," *The Journal of the Japanese Respiratory Society* 45:167, The Japanese Respiratory Society, Japan (2007).

Normanno, N. et al., "Target-based agents against ErbB receptors and their ligands: a novel approach to cancer treatment," *Endocrine-Related. Cancer* 10:1-21, Society for Endocrinology (2003).

Tamura, M. et al., "Structural Correlates of an Anticarcinoma Antibody: Identification of Specificity-Determining Residues (SDRs) and Development of a Minimally Immunogenic Antibody Variant by Retention of SDRs Only," *J. Immunol.* 164:1432-1441, The American Association of Immunologists (2000).

Sato, K., et al., "Solution structure of epiregulin and the effect of its C-terminal domain for receptor binding affinity," *FEBS Letters* 553:232-238, Elsevier Science B.V., Netherlands (2003).

(56) References Cited

OTHER PUBLICATIONS

Kairemo, K.J.A., "Positron Emission Tomography of Monoclonal Antibodies," *Acta Oncol.* 32:825-830, Informa Healthcare, London (1993).
NCBI GenBank Accession No. AAX36706, Hines, L., et al., Entry Date Mar. 16, 2005.
NCBI GenBank Accession No. AAF61510, Cassady-Cain, R.L. and Kaushik, A.K., Entry Date May 2, 2006.
NCBI GenBank Accession No. AAR90995, Liang, Z., et al., Entry Date Mar. 15, 2004.
Nautiyal, J. et al., "Targeting EGFRs and Src signaling with a modified ectodomain of human EGFR (EBIP) and dasatinib in breast cancer," *Cancer Research* 69(2) Suppl 1:3069, American Association for Cancer Research, United States (2008) (Abstract #3069).
Database NCBI on STN, Accession No. NP_001423, "epiregulin [*Homo sapiens*]," Entry Date Apr. 22, 2005.
Flessner, M.F., et al., "Resistance of Tumor Interstitial Pressure to the Penetration of Intraperitoneally Delivered Antibodies into Metastatic Ovarian Tumors," *Clin Cancer Res* 11:3117-3125, American Association for Cancer Research (2005).
Jain, R.K., "Physiological Barriers to Delivery of Monoclonal Antibodies and Other Macromolecules in Tumors," *Cancer Res* 50:814s-819s, American Association for Cancer Research (1990).
Spinelli, G.P., et al., "Long-Term Survival in Metastatic Pancreatic Cancer. A Case Report and Review of the Literature," *J Pancreas (Online)* 7(5):486-491, E.S. Burioni Ricerche Bibliografiche, Italy (2006).
Kurachi, H., et al., "Importance of Transforming Growth Factor α/Epidermal Growth Factor Receptor Autocrine Growth Mechanism in an Ovarian Cancer Cell Line in Vivo," *Cancer Res* 51:5956-5959, American Association for Cancer Research, United States (1991).
Zhang, J., et al., "Intratumoral Epiregulin Is a Marker of Advanced Disease in Non-Small Cell Lung Cancer Patients and Confers Invasive Properties on EGFR-Mutant Cells," *Cancer Prev Res* 1:201-207, American Association for Cancer Research, United States (2008).
Cacia, J., et al., "Isomerization of an Aspartic Acid Residue in the Complementarity-Determining Regions of a Recombinant Antibody to Human IgE: Identification and Effect on Binding Affinity," *Biochemistry* 35:1897-1903, American Chemical Society, United States (1996).
Bischoff, R. and Kolbe, H.V.J., "Deamidation of asparagine and glutamine residues in proteins and peptides: structural determinants and analytical methodology," *Journal of Chromatography B* 662:261-278, Elsevier Science B.V., Netherlands (1994).
Blanche, F., et al., "Stabilization of Recombinant Adenovirus: Site-Directed Mutagenesis of Key Asparagine Residues in the Hexon Protein," *Analytical Biochemistry* 297:1-9, Academic Press, United States (2001).
Bugelski, P.J., et al., "Preclinical development of keliximab, a Primatized™ anti-CD4 monoclonal antibody, in human CD4 transgenic mice: characterization of the model and safety studies," *Human & Experimental Toxicology* 19:230-243, Nature America, Inc., United States (2000).
Chothia, C. and Lesk, A.M., "Canonical Structures for the Hypervariable Regions of Immunoglobulins," *J. Mol. Biol.* 196:901-917, Academic Press, United States (1987).
Chothia, C., et al., "Structural Repertoire of the Human $V_H$ Segments," *J. Mol. Biol.* 227:799-817, Academic Press, United States (1992).
Geiger, T. and Clarke, S., "Deamidation, Isomerization, and Racemization at Asparaginyl and Aspartyl Residues in Peptides," *The Journal of Biological Chemistry* 262(2):785-794, The American Society of Biological Chemists, Inc., United States (1987).
Goolcharran, C., et al., "The Effects of a Histidine Residue on the C-Terminal Side of Asparaginyl Residue on the Rate of Deamidation Using Model Pentapeptides," *Journal of Pharmaceutical Sciences* 89(6):818-825, Wiley-Liss, United States (2000).

Harris, R.J., et al., "Identification of multiple sources of charge heterogeneity in a recombinant antibody," *Journal of Chromatography B* 752:233-245, Elsevier Science B.V., Netherlands (2001).
Manning, M.C., et al., "Stability of Protein Pharmaceuticals," *Pharmaceutical Research* 6(11):903-918, Plenum Publishing Corporation, United States (1989).
Perkins, M. et al., "Determination of the Origin of Charge Heterogeneity in a Murine Monoclonal Antibody," *Pharmaceutical Research* 17(9):1110-1117, Plenum Publishing Corporation, United States (2000).
Robinson, N.E. and Robinson, A.B., "Molecular clocks," *PNAS* 98(3):944-949, National Academy of Sciences, United States (2001).
Robinson, N.E. and Robinson, A.B., "Deamidation of human proteins," *PNAS* 98(22):12409-12413, National Academy of Sciences, United States (2001).
Sandusky, G.E., et al., "Use of Monoclonal Antibodies to Human Lymphocytes to Identify Lymphocyte Subsets in Lymph Nodes of the Rhesus Monkey and the Dog," *J. Med. Primatol* 15:441-451, Alan R. Liss, Inc., United States (1986).
Schlereth, B., et al., "T-cell activation and B-cell depletion in chimpanzees treated with a bispecific anti-CD19/anti-CD3 single-chain antibody construct," *Cancer Immunol. Immunother.* 55:503-514, Springer-Verlag (2006).
Scotchler, J.W. and Robinson, A.B., "Deamidation of Glutaminyl Residues: Dependence on pH, Temperature, and Ionic Strength," *Analytical Biochemistry* 59:319-322, Academic Press, Inc., United States (1974).
Sugo, I., et al., "Study on structural properties of antibody pharmaceuticals (3)—Activity reduction caused by deamidation of Asn residues and molecular design for preventing the reduction," Proc. 124th Ann. Meeting Pharmacol. Soc. Japan (Nihon Yakugakukai Dai124nenki Osaka 2004 youshishyu), 30[p2]III-389, p. 103 (Mar. 5, 2004) (unverified English language translation included).
Tomizawa, H., et al., "Stabilization of lysozyme against irreversible inactivation by alterations of the Asp-Gly sequences," *Protein Engineering* 8(10):1023-1028, Oxford University Press, England (1995).
Tyler-Cross, R. and Schirch, V. "Effects of Amino Acid Sequence, Buffers, and Ionic Strength on the Rate and Mechanism of Deamidation of Asparagine Residues in Small Peptides," *The Journal of Biological Chemistry* 266(33):22549-22556, The American Society for Biochemistry and Molecular Biology, Inc., United States (1991).
Uda, A., et al., "CD3 polymorphism in cynomolgus monkeys (*Macaca fascicularis*)," *J. Med. Primatol* 30:141-147, Munksgaard, Copenhagen, Denmark (2001).
International Search Report for International Patent No. PCT/JP2012/084042, filed Dec. 28, 2012, dated Feb. 5, 2013, Japanese Patent Office, Tokyo, Japan.
An, S.-J., et al., "Identification of Enriched Driver Gene Alterations in Subgroups of Non-Small Cell Lung Cancer Patients Based on Histology and Smoking Status," *PLoS ONE* 7(6):e40109, 13 pages, Open Access Article (2012).
International Search Report for International Application No. PCT/JP2014/066512, Japanese Patent Office, Japan, dated Aug. 12, 2014, 2 pages (Not a Corresponding Application).
Gold, K.A., "New Strategies in Squamous Cell Carcinoma of the Lung: Identification of Tumor Drivers to Personalize Therapy," *Clinical Cancer Research* 18(11):3002-3007, American Association for Cancer, United States (2012).
Langer, C.J., et al., "The Evolving Role of Histology in the Management of Advanced Non-Small-Cell Lung Cancer," *Journal of Clinical Oncology* 28(36):5311-5320, American Society of Clinical Oncology, United States (2010).
Pennell, N.A., "Selection of chemotherapy for patients with advanced non-small cell lung cancer," *Cleveland Clinic Journal of Medicine* 79:e-S46-e-S50, Cleveland Clinic Educational Foundation, United States (2012).
Sandler, A., et al., "Treatment Outcomes by Tumor Histology in Eastern Cooperative Group Study E4599 of Bevacizumab with Paclitaxel/Carboplatin for Advanced Non-small Cell Lung Cancer,"

(56) References Cited

OTHER PUBLICATIONS

*Journal of Thoracic Oncology* 5(9):1416-1423, International Association for the Study of Lung Cancer, United States (2010).
Co-Pending U.S. Appl. No. 14/900,928, inventors Suzuki, Masami, et al., 371(c) date of Dec. 22, 2015 (Not Yet Published).
"Antibody Structure and Function," in *Immunology*, Fifth Edition, Roitt, et al., Eds., pp. 110-111, Mir Publishers, Moscow (2000).
"Antibody Structure and Function," in *Immunology*, Fifth Edition, Roitt, et al., Eds., pp. 80-81, C.V. Mosby Co., United States (1998).
Imai-Nishiya, H., et al., "Double knockdown of α1,6-fucosyltransferase (FUT8) and GDP-mannose 4,6-dehydratase (GMD) in antibody-producing cells: a new strategy for generating fully non-fucosylated therapeutic antibodies with enhanced ADCC," *BMC Biotechnology* 7:84, BioMed Central Ltd., United Kingdom (2007).
Schildbach, J.F., et al., "Modulation of antibody affinity by a non-contact residue," *Protein Science* 2:206-214, Cambridge University Press, United States (1993).
IMGT Scientific Chart, "Correspondence between the IMGT unique numbering for C-DOMAIN, the IMGT exon number, the Eu and Kabat numberings: Human IGHG," www.imgt.org/IMGTScientificChart/Numbering/Hu_IGHGnber.html, accessed Sep. 5, 2017.

\* cited by examiner

EREG_HUMAN QVSITKCSSDMNGYCLHGQCIYLVDMSQNYCRCEVGTGYTGVRCEHFFL (SEQ ID NO:35)
TGFA_HUMAN VSHFNDCPDSHTQFCFHGTCRFLVQEDKPACVCHSGYVGARCEHADL (SEQ ID NO:36)

METHOD FOR TREATING A DISEASE ORIGINATED FROM RECEPTOR ACTIVATION BY EREG AND TGFα

TECHNICAL FIELD

The present invention relates to pharmaceutical compositions comprising an antagonist of an EGF family ligand as a component.

BACKGROUND ART erbB Receptor Family and EGF Family Ligands

The epidermal growth factor receptor (EGFR) family erbB receptors include the following four members: EGFR (erbB1), erbB2, erbB3, and erbB4. The EGF family ligands include the following 13 members: EGF, TGFα (transforming growth factor α), HB-EGF (heparin-binding EGF-like growth factor), BTC (betacellulin), AREG (amphiregulin), EREG (epiregulin), EPGN (epigen), and NRGs (neuregulin1-6) (see Non-Patent Document 3). Activation of an erbB receptor is regulated by the presence of a ligand (based on regulation of spatiotemporal expression) and posttranslational processing. EGF family ligands are produced as type I membrane proteins. These transmembrane proteins undergo protease-mediated processing and the processed proteins function as soluble ligands. Some of the ligands remain membrane-type and activate nearby receptors on cells. Specifically, the mechanisms of receptor activation by EGF family ligands include an endocrine mechanism in which secreted peptides spread systemically through the bloodstream and act on receptor-expressing cells, an autocrine mechanism in which secreted peptides stimulate receptors on the same cells expressing them, a paracrine mechanism in which secreted peptides activate receptors on nearby cells, and a juxtacrine mechanism in which membrane ligands stimulate adjacent cellular receptors (see Non-Patent Document 6).

EGF family ligands cause EGFR/EGFR homodimer formation, EGFR/erbB2 and EGFR/erbB4 heterodimer formation and such, and activate endogenous protein tyrosine kinases, and induce receptor autophosphorylation. The phosphorylated receptors attract several types of intracellular substrates and result in stimulation of cell growth or other cellular activities.

EGF family ligands exhibit different affinity to erbB receptors and show refined receptor-binding specificity. Furthermore, each EGF family ligand unexpectedly induces different and diverse physiological reactions in cells even though it binds to the same receptor (see Non-Patent Document 11). TGFα and AREG stimulate DNA synthesis to the same degree in MDCK cells. AREG causes E-cadherin redistribution and morphological changes in MDCK cells, while TGFα does not. In human mammary epithelial cells MCF10A, AREG enhances cell motility and invasiveness better than EGF. AREG stimulates NFκB signals and interleukin-1 secretion, but EGF does not. TGFα transduces signals through different effector molecules from those of EGF. Of the erbB family receptors, AREG, EGF, and TGFα selectively bind to EGFR. The above-mentioned differences cannot be simply explained by the degree of saturation of EGFR binding due to affinity strength.

Furthermore, data demonstrating the functional complementarity and specificity of ligands have been obtained from analyses of genetically manipulated mice (see Non-Patent Document 6). AREG-, BTC-, EGF-, EREG-, and TGFα-deficient mice are viable but each shows several characteristic phenotypes. The exception is HB-EGF, and deletion of this gene causes impairment of the heart and lungs leading to fetal death. AREG-deficient mice have a mammary gland defect and impaired liver regeneration. In TGFα-deficient mice, abnormalities were observed in hair follicles and eyelid closure. Skin abnormality is not reported in EGF-, BTC-, and AREG-deficient mice. However, delayed wound healing in HB-EGF-deficient mice, and chronic dermatitis symptoms that occur with aging in EREG-deficient mice have been reported. In TGFα-overexpressing mice, the skin thickens and undergoes carcinogenesis easily. In AREG-overexpressing mice, psoriasis-like inflammatory lesions are developed.

Difference in the affinities of EGF member ligands towards the four receptors is a determining factor of the ligands' signaling specificities. In addition, it is thought that difference in the physiological functions of the ligands can be due to differences in the receptor conformations induced when the ligands bind to the receptors, changes in the phosphorylated sites of the receptor tyrosine residues caused by the above conformational differences, and differences in the coupling with signal coupling factors (see Non-Patent Document 11).

erbB receptor activation affects, for example, proliferation, survival, and differentiation, and thus is important for the determination of cell fate. Therefore, abnormality of erbB receptor activation plays an important role in human tumor development. Furthermore, erbB receptor stimulation by functionally selective ligands may be involved in human tumor proliferation.

Cancer and erbB Receptor Signaling

EGFR mutation and up-regulation have been previously reported in human epithelial cancers, and it has been revealed that enhancement of the activity of EGFR itself or its downstream signals has an important role in the development and progression of cancer. Enhancement of the tyrosine phosphorylation activity of mutated EGFR, EGFR activation by ligands through the autocrine loop, and amplification of chromosomal receptor genes are common characteristics observed in various cancers such as breast cancer, prostate cancer, pancreatic cancer, colon cancer, lung cancer, and head and neck cancer. It has been experimentally demonstrated that when activated EGFR is introduced into non-neoplastic cell lines, malignant phenotypes are induced. EGFR on cancer cells is often constitutively activated by EGF ligands present in tumors. There are reports showing that cancers expressing TGFα, AREG, and HB-EGF are associated with poor prognosis and resistance to chemotherapeutic agents. Constitutive K-RAS activation by the EGFR signal pathway induces EREG expression, and enhances tumorigenicity (see Non-Patent Document 1).

Therefore, EGFRs are attractive candidate targets for molecular targeted therapy. To date, EGFR and erbB2 have been confirmed to be useful targets by therapeutic agents for treating colon cancer, lung cancer, head and neck cancer, breast cancer, and gastric cancer. The use of an anti-EGFR antibody is an essential therapeutic method for metastatic colon cancer patients. This is based on the evidence that the administration prolongs a progression-free period and shows high responsiveness.

The signal network of EGFR family receptors is not only critical to proliferation and survival of cancer cells, but also has an essential role in biological homeostasis which regulates proliferation and differentiation of normal cells. Inhibition of EGF receptor suppresses signals critical to biological homeostasis, and as a result causes serious side effects.

Hypersensitivity, pulmonary disorders, skin symptoms, photosensitivity, fever, and myocardial disorders have been reported to be side effects of anti-EGFR antibodies (see Non-Patent Document 5). In particular, skin toxicity is observed in many cases since EGFR signaling has an important role in the skin. In some cases, changes in the dosage and schedule of administration, and discontinuation of therapy become necessary due to moderate to severe toxicity.

Furthermore, it has been reported that administration of anti-EGFR antibodies frequently causes hypomagnesemia (see Non-Patent Document 8). There are also cases in which the treatment needs to be interrupted due to severe side effects. This hypomagnesemia has been shown to be related to magnesium consumption in the distal convoluted tubule. It has been shown that when renal EGFR does not receive sufficient stimulation, the epithelial magnesium channel TRPM6 is not sufficiently activated, and thus magnesium is consumed (see Non-Patent Document 9). EGF has been shown to be involved in renal EGFR activation.

As described above, the activation of EGFR family receptors by EGF family ligands is very complicated. One may consider the approach of selecting EGF family ligands as targets of cancer therapeutic agents; however, at present the approach of targeting the receptors is preferred. The reasons are the presence of multiple activating ligands for EGFR and erbB4, that the activating ligand for erbB2 is unknown, and that unidentified activating ligands may exist.

However, in approaches to prevent stimuli derived from all ligands by setting EGFR as target of inhibition, side effects caused by the intrinsic action of EGFR inhibition cannot be separated from its therapeutic effects. There is still a possibility that side effects could be reduced by limiting the suppression of signal transduction through ligand suppression. Elucidation of the mechanism in cancer cells is critical for developing antitumor agents that have anticancer effects with minimum side effects. Of the EGF-like ligands, TGFα, AREG, and HB-EGF have been reported to promote cancer cell proliferation as autocrine factors (see Non-Patent Document 4, Non-Patent Document 7, and Non-Patent Document 10).

PRIOR ART DOCUMENTS

Non-Patent Documents

[Non-Patent Document 1] Baba, I. et al. (2000) Cancer Res. 60: 6886-6889.
[Non-Patent Document 2] Force, T. et al. (2007) Nat. Rev. Cancer 7: 332-344.
[Non-Patent Document 3] Higashiyama, S. et al. (2008) Cancer Sci. 99: 214-220.
[Non-Patent Document 4] Johnson, G. R. et al. (1992) J. Cell Biol. 118: 741-751.
[Non-Patent Document 5] Lacouture, M. E. (2006) Nat. Rev. Cancer 6: 803-812.
[Non-Patent Document 6] Schneider, M. R. & Wolf, E. (2009) J. Cell. Physiol. 218: 460-466.
[Non-Patent Document 7] Seth, D. et al. (1999) Br. J. Cancer 80: 657-669.
[Non-Patent Document 8] Tejpar, S. et al. (2007) Lancet Oncol. 8:387-394.
[Non-Patent Document 9] Groenestege, W. M. et al. (2007) J. Clin. Invest. 117: 2260-2267.
[Non-Patent Document 10] Willmarth, N. E. et al. (2006) J. Biol. Chem. 281: 37728-37737
[Non-Patent Document 11] Wilson, K. J. et al. (2009) Pharmacol. Ther. 122: 1-8.

DISCLOSURE OF THE INVENTION

Problems to be Solved by the Invention

An objective of the present invention is to identify combinations of EGFR ligands that may serve as targets for inhibiting the proliferation of specific cancer cells. Another objective is to isolate antibodies having ligand-neutralizing ability, show examples of combinations of effective antibody sequences, and provide pharmaceutical compositions comprising the antibodies as a component.

Means for Solving the Problems

The present inventors conducted dedicated research to achieve the above objectives, and identified inhibition of a combination of EGFR ligands that serve as target for inhibition of cancer cell proliferation. More specifically, the present inventors discovered that EREG antagonists and TGFα antagonists are useful as inhibitors of cell proliferation.

The present invention relates to pharmaceutical compositions comprising an antagonist of an EGF family ligand as a component. Specifically, the present invention provides the following:

[1] A pharmaceutical composition comprising an EREG antagonist and a TGFα antagonist as active ingredients.
[2] The pharmaceutical composition of [1], wherein the pharmaceutical composition is an inhibitor of cell proliferation.
[3] The pharmaceutical composition of [1], wherein the pharmaceutical composition is an anticancer agent.
[4] The pharmaceutical composition of any one of [1] to [3], wherein the EREG antagonist is an anti-EREG antibody.
[5] The pharmaceutical composition of any one of [1] to [4], wherein the anti-EREG antibody is the antibody of any of (a) to (x) below:
(a) an antibody that comprises a heavy chain comprising CDR1 having the amino acid sequence of SEQ ID NO: 61, CDR2 having the amino acid sequence of SEQ ID NO: 62, and CDR3 having the amino acid sequence of SEQ ID NO: 63;
(b) an antibody that comprises a light chain comprising CDR1 having the amino acid sequence of SEQ ID NO: 64, CDR2 having the amino acid sequence of SEQ ID NO: 65, and CDR3 having the amino acid sequence of SEQ ID NO: 66;
(c) an antibody that comprises the heavy chain of (a) and the light chain of (b);
(d) an antibody that recognizes the same epitope recognized by the antibody of (c);
(e) an antibody that comprises a heavy chain comprising CDR1 having the amino acid sequence of SEQ ID NO: 67, CDR2 having the amino acid sequence of SEQ ID NO: 68, and CDR3 having the amino acid sequence of SEQ ID NO: 69;
(f) an antibody that comprises a light chain comprising CDR1 having the amino acid sequence of SEQ ID NO: 70, CDR2 having the amino acid sequence of SEQ ID NO: 71, and CDR3 having the amino acid sequence of SEQ ID NO: 72;
(g) an antibody that comprises the heavy chain of (e) and the light chain of (f);

(h) an antibody that recognizes the same epitope recognized by the antibody of (g);
(i) an antibody that comprises a heavy chain comprising CDR1 having the amino acid sequence of SEQ ID NO: 73, CDR2 having the amino acid sequence of SEQ ID NO: 74, and CDR3 having the amino acid sequence of SEQ ID NO: 75;
(j) an antibody that comprises a light chain comprising CDR1 having the amino acid sequence of SEQ ID NO: 76, CDR2 having the amino acid sequence of SEQ ID NO: 77, and CDR3 having the amino acid sequence of SEQ ID NO: 78;
(k) an antibody that comprises the heavy chain of (i) and the light chain of (j);
(l) an antibody that recognizes the same epitope recognized by the antibody of (k);
(m) an antibody that comprises a heavy chain comprising CDR1 having the amino acid sequence of SEQ ID NO: 79, CDR2 having the amino acid sequence of SEQ ID NO: 80, and CDR3 having the amino acid sequence of SEQ ID NO: 81;
(n) an antibody that comprises a light chain comprising CDR1 having the amino acid sequence of SEQ ID NO: 82, CDR2 having the amino acid sequence of SEQ ID NO: 83, and CDR3 having the amino acid sequence of SEQ ID NO: 84;
(o) an antibody that comprises the heavy chain of (m) and the light chain of (n);
(p) an antibody that recognizes the same epitope recognized by the antibody of (o);
(q) an antibody that comprises a heavy chain comprising CDR1 having the amino acid sequence of SEQ ID NO: 85, CDR2 having the amino acid sequence of SEQ ID NO: 86, and CDR3 having the amino acid sequence of SEQ ID NO: 87;
(r) an antibody that comprises a light chain comprising CDR1 having the amino acid sequence of SEQ ID NO: 88, CDR2 having the amino acid sequence of SEQ ID NO: 89, and CDR3 having the amino acid sequence of SEQ ID NO: 90;
(s) an antibody that comprises the heavy chain of (q) and the light chain of (r);
(t) an antibody that recognizes the same epitope recognized by the antibody of (s);
(u) an antibody that comprises a heavy chain comprising CDR1 having the amino acid sequence of SEQ ID NO: 91, CDR2 having the amino acid sequence of SEQ ID NO: 92, and CDR3 having the amino acid sequence of SEQ ID NO: 93;
(v) an antibody that comprises a light chain comprising CDR1 having the amino acid sequence of SEQ ID NO: 94, CDR2 having the amino acid sequence of SEQ ID NO: 95, and CDR3 having the amino acid sequence of SEQ ID NO: 96;
(w) an antibody that comprises the heavy chain of (u) and the light chain of (v); and
(x) an antibody that recognizes the same epitope recognized by the antibody of (w).
[6] The pharmaceutical composition of any one of [1] to [3], wherein the TGFα antagonist is an anti-TGFα antibody.
[7] The pharmaceutical composition of [6], wherein the anti-TGFα antibody is the antibody of any of (a) to (d) below:
(a) an antibody that comprises a heavy chain comprising CDR1 having the amino acid sequence of SEQ ID NO: 47, CDR2 having the amino acid sequence of SEQ ID NO: 48, and CDR3 having the amino acid sequence of SEQ ID NO: 49;
(b) an antibody that comprises a light chain comprising CDR1 having the amino acid sequence of SEQ ID NO: 50, CDR2 having the amino acid sequence of SEQ ID NO: 51, and CDR3 having the amino acid sequence of SEQ ID NO: 52;
(c) an antibody that comprises the heavy chain of (a) and the light chain of (b); and
(d) an antibody that recognizes the same epitope recognized by the antibody of (c).
[8] The pharmaceutical composition of any one of [1] to [3], wherein the EREG antagonist is an anti-EREG antibody, and the TGFα antagonist is an anti-TGFα antibody.
[9] The pharmaceutical composition of [8], wherein the anti-EREG antibody is the antibody of any of (a) to (x) below:
(a) an antibody that comprises a heavy chain comprising CDR1 having the amino acid sequence of SEQ ID NO: 61, CDR2 having the amino acid sequence of SEQ ID NO: 62, and CDR3 having the amino acid sequence of SEQ ID NO: 63;
(b) an antibody that comprises a light chain comprising CDR1 having the amino acid sequence of SEQ ID NO: 64, CDR2 having the amino acid sequence of SEQ ID NO: 65, and CDR3 having the amino acid sequence of SEQ ID NO: 66;
(c) an antibody that comprises the heavy chain of (a) and the light chain of (b);
(d) an antibody that recognizes the same epitope recognized by the antibody of (c);
(e) an antibody that comprises a heavy chain comprising CDR1 having the amino acid sequence of SEQ ID NO: 67, CDR2 having the amino acid sequence of SEQ ID NO: 68, and CDR3 having the amino acid sequence of SEQ ID NO: 69;
(f) an antibody that comprises a light chain comprising CDR1 having the amino acid sequence of SEQ ID NO: 70, CDR2 having the amino acid sequence of SEQ ID NO: 71, and CDR3 having the amino acid sequence of SEQ ID NO: 72;
(g) an antibody that comprises the heavy chain of (e) and the light chain of (f);
(h) an antibody that recognizes the same epitope recognized by the antibody of (g);
(i) an antibody that comprises a heavy chain comprising CDR1 having the amino acid sequence of SEQ ID NO: 73, CDR2 having the amino acid sequence of SEQ ID NO: 74, and CDR3 having the amino acid sequence of SEQ ID NO: 75;
(j) an antibody that comprises a light chain comprising CDR1 having the amino acid sequence of SEQ ID NO: 76, CDR2 having the amino acid sequence of SEQ ID NO: 77, and CDR3 having the amino acid sequence of SEQ ID NO: 78;
(k) an antibody that comprises the heavy chain of (i) and the light chain of (j);
(l) an antibody that recognizes the same epitope recognized by the antibody of (k);
(m) an antibody that comprises a heavy chain comprising CDR1 having the amino acid sequence of SEQ ID NO: 79, CDR2 having the amino acid sequence of SEQ ID NO: 80, and CDR3 having the amino acid sequence of SEQ ID NO: 81;
(n) an antibody that comprises a light chain comprising CDR1 having the amino acid sequence of SEQ ID NO: 82, CDR2 having the amino acid sequence of SEQ ID NO: 83, and CDR3 having the amino acid sequence of SEQ ID NO: 84;
(o) an antibody that comprises the heavy chain of (m) and the light chain of (n);
(p) an antibody that recognizes the same epitope recognized by the antibody of (o);
(q) an antibody that comprises a heavy chain comprising CDR1 having the amino acid sequence of SEQ ID NO: 85, CDR2 having the amino acid sequence of SEQ ID NO: 86, and CDR3 having the amino acid sequence of SEQ ID NO: 87;
(r) an antibody that comprises a light chain comprising CDR1 having the amino acid sequence of SEQ ID NO: 88, CDR2 having the amino acid sequence of SEQ ID NO: 89, and CDR3 having the amino acid sequence of SEQ ID NO: 90;
(s) an antibody that comprises the heavy chain of (q) and the light chain of (r);
(t) an antibody that recognizes the same epitope recognized by the antibody of (s);
(u) an antibody that comprises a heavy chain comprising CDR1 having the amino acid sequence of SEQ ID NO: 91, CDR2 having the amino acid sequence of SEQ ID NO: 92, and CDR3 having the amino acid sequence of SEQ ID NO: 93;
(v) an antibody that comprises a light chain comprising CDR1 having the amino acid sequence of SEQ ID NO: 94, CDR2 having the amino acid sequence of SEQ ID NO: 95, and CDR3 having the amino acid sequence of SEQ ID NO: 96;
(w) an antibody that comprises the heavy chain of (u) and the light chain of (v); and
(x) an antibody that recognizes the same epitope recognized by the antibody of (w).
[10] The pharmaceutical composition of [8] or [9], wherein the anti-TGFα antibody is the antibody of any of (a) to (d) below:
(a) an antibody that comprises a heavy chain comprising CDR1 having the amino acid sequence of SEQ ID NO: 47, CDR2 having the amino acid sequence of SEQ ID NO: 48, and CDR3 having the amino acid sequence of SEQ ID NO: 49;
(b) an antibody that comprises a light chain comprising CDR1 having the amino acid sequence of SEQ ID NO: 50, CDR2 having the amino acid sequence of SEQ ID NO: 51, and CDR3 having the amino acid sequence of SEQ ID NO: 52;
(c) an antibody that comprises the heavy chain of (a) and the light chain of (b); and
(d) an antibody that recognizes the same epitope recognized by the antibody of (c).
[11] An antibody that binds to EREG and TGFα.
[12] The antibody of [11], which has antagonistic activity against EREG and TGFα.
[13] The antibody of [11] or [12], which is the antibody of any one of (a) to (d) below:
(a) an antibody that comprises a heavy chain comprising CDR1 having the amino acid sequence of SEQ ID NO: 10, CDR2 having the amino acid sequence of SEQ ID NO: 12, and CDR3 having the amino acid sequence of SEQ ID NO: 14;
(b) an antibody that comprises a light chain comprising CDR1 having the amino acid sequence of SEQ ID NO: 16, CDR2 having the amino acid sequence of SEQ ID NO: 18, and CDR3 having the amino acid sequence of SEQ ID NO: 20;
(c) an antibody that comprises the heavy chain of (a) and the light chain of (b); and
(d) an antibody that recognizes the same epitope recognized by the antibody of (c).
[14] An antibody that recognizes the region from Gln at position 56 to Leu at position 102 of SEQ ID NO: 4 (human EREG), and/or the region from Val at position 41 to Leu at position 87 of SEQ ID NO: 26 (human TGFα).
[15] A pharmaceutical composition comprising an EREG- and TGFα-binding substance as an active ingredient.
[16] The pharmaceutical composition of [15], wherein the EREG- and TGFα-binding substance is the antibody of any one of [11] to [14].
[17] A method of screening for an anticancer agent, which comprises the steps of:
(a) measuring the antagonistic activity of a test substance against EREG;
(b) measuring the antagonistic activity of a test substance against TGFα; and
(c) selecting a test substance that has antagonistic activity against EREG and TGFα.

Furthermore, the present invention provides the following:
[18] a method for suppressing cell proliferation, which comprises the step of administering a pharmaceutical composition of the present invention (for example, an EREG antagonist and a TGFα antagonist) to a subject;
[19] a method for treating cancer, which comprises the step of administering a pharmaceutical composition of the present invention (for example, an EREG antagonist and a TGFα antagonist) to a subject;
[20] a composition comprising an EREG antagonist and a TGFα antagonist for use in cell proliferation inhibition or cancer treatment; and
[21] use of a composition comprising an EREG antagonist and a TGFα antagonist in the production of a cell proliferation inhibitor or an anticancer agent.

BRIEF DESCRIPTION OF THE DRAWINGS

FIG. 6a shows binding to EREG. FIG. 6b shows binding to TGFα.

MODE FOR CARRYING OUT THE INVENTION

Figure 1:
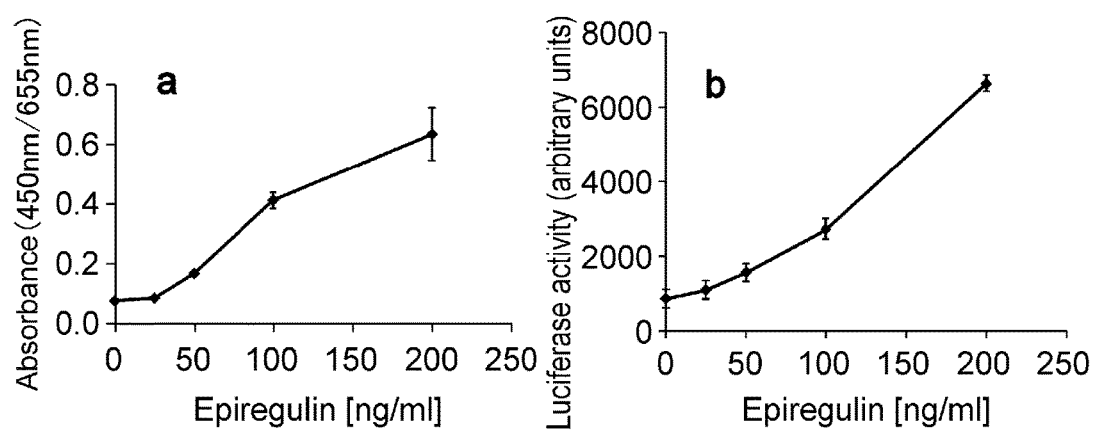
FIG. 1 shows that EGF(R) cells proliferate in response to EREG. (a) Cell proliferation was determined by WST-8 assay. (b) Cell proliferation was determined based on luciferase activity.

The present invention provides pharmaceutical compositions comprising an EREG antagonist and a TGFα antagonist as active ingredients.

In the present invention, "EREG antagonist" refers to substances that upon binding to EREG inhibit the binding between EREG and EGFR and EGFR-mediated EREG signal transduction, or substances that decrease the expression level of EREG.

The EREG antagonists are not particularly limited, and they may be any substances as long as they have the above-mentioned activity. Examples of the substances that upon binding to EREG inhibit the binding between EREG and EGFR and EGFR-mediated EREG signal transduction include antibodies that have antagonistic activity against EREG. Examples of substances that decrease the expression level of EREG include siRNAs or antisense oligonucleotides against the EREG gene.

The EREG antagonists are preferably, but are not limited to, antagonists against human EREG. The sequence of human EREG is already known (GenBank Accession No: NM_001432, and such).

The EREG antagonists may target soluble EREG or transmembrane EREG. Alternatively, they may target both of them.

The EREG antagonists may be any substances, and for example, the antagonists described in WO2008/047723, a commercially available anti-human EREG antibody (R&D Systems, AF1195), and such may be used.

In a preferred embodiment, an example of the antagonists described in WO2008/047723 is any one of the antibodies described below:
(a) an antibody that comprises a heavy chain comprising CDR1 having the amino acid sequence of SEQ ID NO: 61, CDR2 having the amino acid sequence of SEQ ID NO: 62, and CDR3 having the amino acid sequence of SEQ ID NO: 63;
(b) an antibody that comprises a light chain comprising CDR1 having the amino acid sequence of SEQ ID NO: 64, CDR2 having the amino acid sequence of SEQ ID NO: 65, and CDR3 having the amino acid sequence of SEQ ID NO: 66;
(c) an antibody that comprises the heavy chain of (a) and the light chain of (b);
(d) an antibody that recognizes the same epitope recognized by the antibody of (c);
(e) an antibody that comprises a heavy chain comprising CDR1 having the amino acid sequence of SEQ ID NO: 67, CDR2 having the amino acid sequence of SEQ ID NO: 68, and CDR3 having the amino acid sequence of SEQ ID NO: 69;
(f) an antibody that comprises a light chain comprising CDR1 having the amino acid sequence of SEQ ID NO: 70, CDR2 having the amino acid sequence of SEQ ID NO: 71, and CDR3 having the amino acid sequence of SEQ ID NO: 72;
(g) an antibody that comprises the heavy chain of (e) and the light chain of (f);
(h) an antibody that recognizes the same epitope recognized by the antibody of (g);
(i) an antibody that comprises a heavy chain comprising CDR1 having the amino acid sequence of SEQ ID NO: 73, CDR2 having the amino acid sequence of SEQ ID NO: 74, and CDR3 having the amino acid sequence of SEQ ID NO: 75;
(j) an antibody that comprises a light chain comprising CDR1 having the amino acid sequence of SEQ ID NO: 76, CDR2 having the amino acid sequence of SEQ ID NO: 77, and CDR3 having the amino acid sequence of SEQ ID NO: 78;
(k) an antibody that comprises the heavy chain of (i) and the light chain of (j);
(l) an antibody that recognizes the same epitope recognized by the antibody of (k);
(m) an antibody that comprises a heavy chain comprising CDR1 having the amino acid sequence of SEQ ID NO: 79, CDR2 having the amino acid sequence of SEQ ID NO: 80, and CDR3 having the amino acid sequence of SEQ ID NO: 81;
(n) an antibody that comprises a light chain comprising CDR1 having the amino acid sequence of SEQ ID NO: 82, CDR2 having the amino acid sequence of SEQ ID NO: 83, and CDR3 having the amino acid sequence of SEQ ID NO: 84;
(o) an antibody that comprises the heavy chain of (m) and the light chain of (n);
(p) an antibody that recognizes the same epitope recognized by the antibody of (o);
(q) an antibody that comprises a heavy chain comprising CDR1 having the amino acid sequence of SEQ ID NO: 85, CDR2 having the amino acid sequence of SEQ ID NO: 86, and CDR3 having the amino acid sequence of SEQ ID NO: 87;
(r) an antibody that comprises a light chain comprising CDR1 having the amino acid sequence of SEQ ID NO: 88, CDR2 having the amino acid sequence of SEQ ID NO: 89, and CDR3 having the amino acid sequence of SEQ ID NO: 90;
(s) an antibody that comprises the heavy chain of (q) and the light chain of (r);
(t) an antibody that recognizes the same epitope recognized by the antibody of (s);
(u) an antibody that comprises a heavy chain comprising CDR1 having the amino acid sequence of SEQ ID NO: 91, CDR2 having the amino acid sequence of SEQ ID NO: 92, and CDR3 having the amino acid sequence of SEQ ID NO: 93;

(v) an antibody that comprises a light chain comprising CDR1 having the amino acid sequence of SEQ ID NO: 94, CDR2 having the amino acid sequence of SEQ ID NO: 95, and CDR3 having the amino acid sequence of SEQ ID NO: 96;

(w) an antibody that comprises the heavy chain of (u) and the light chain of (v); and (x) an antibody that recognizes the same epitope recognized by the antibody of (w).

In the present invention, "TGFα antagonist" refers to substances that upon binding to TGFα inhibit the binding between TGFα and EGFR and EGFR-mediated TGFα signal transduction, or substances that decrease the expression level of TGFα.

There is no particular limitation on the TGFα antagonists, and they may be any substances as long as they have the above-mentioned activity. Examples of substances that upon binding to TGFα inhibit the binding between TGFα and EGFR and EGFR-mediated TGFα signal transduction include antibodies that have antagonistic activity against TGFα. Examples of substances that decrease the expression level of TGFα include siRNAs or antisense oligonucleotides against the TGFα gene.

The TGFα antagonists are preferably, but are not limited to, antagonists against human TGFα. The sequence of human TGFα is already known (GenBank Accession Nos: NM_003236, M31172, and such).

The TGFα antagonists may target soluble TGFα or transmembrane TGFα. Alternatively, they may target both of them.

The TGFα antagonists may be any substances, and for example, the antagonists described in WO2004/076622, commercially available anti-TGFα antibodies (GeneTex, GTX16811; and R&D Systems, AB-239-NA), and such may be used.

In a preferred embodiment, an example of an anti-TGFα antibody is any one of the antibodies described below:

(a) an antibody that comprises a heavy chain comprising CDR1 having the amino acid sequence of SEQ ID NO: 47, CDR2 having the amino acid sequence of SEQ ID NO: 48, and CDR3 having the amino acid sequence of SEQ ID NO: 49;

(b) an antibody that comprises a light chain comprising CDR1 having the amino acid sequence of SEQ ID NO: 50, CDR2 having the amino acid sequence of SEQ ID NO: 51, and CDR3 having the amino acid sequence of SEQ ID NO: 52;

(c) an antibody that comprises the heavy chain of (a) and the light chain of (b); and (d) an antibody that recognizes the same epitope recognized by the antibody of (c).

The EREG antagonist and the TGFα antagonist comprised in a pharmaceutical composition comprising as active ingredients an EREG antagonist and a TGFα antagonist of the present invention may be the same substance or different substances. Specifically, a substance having both EREG antagonist activity and TGFα antagonist activity may be used as an active ingredient, or a substance having EREG antagonist activity alone and a substance having TGFα antagonist activity alone may be used as active ingredients.

Furthermore, a substance having both EREG antagonist activity and TGFα antagonist activity and a substance having EREG antagonist activity alone, or a substance having both EREG antagonist activity and TGFα antagonist activity and a substance having TGFα antagonist activity alone may be used as active ingredients.

The present invention also provides antibodies that bind to EREG and TGFα. The antibodies that bind to EREG and TGFα are preferably antibodies that bind to human EREG and human TGFα. Human EREG and human TGFα are as described above.

Examples of EREG binding include binding to soluble EREG, binding to transmembrane EREG, binding to soluble and transmembrane EREG, and such.

Examples of TGFα binding include binding to soluble TGFα, binding to transmembrane TGFα, binding to soluble and transmembrane TGFα, and such.

There is no particular limitation on the antibodies that bind to EREG and TGFα in the present invention. However, they are preferably antagonist antibodies that have antagonist activity against EREG or TGFα, and more preferably antagonist antibodies that have antagonist activity against EREG and TGFα.

There is no particular limitation on the antibodies that bind to human EREG and TGFα. However, they preferably recognize a common region that is highly homologous between EREG and TGFα. Examples of such regions include the region from Gln at position 56 to Leu at position 102 of the amino acid sequence of SEQ ID NO: 4 (human EREG) in human EREG, and the region from Val at position 41 to Leu at position 87 of the amino acid sequence of SEQ ID NO: 26 (human TGFα) in human TGFα. Therefore, preferred examples of antibodies that recognize EREG and TGFα of the present invention include antibodies that recognize the region from Gln at position 56 to Leu at position 102 of the amino acid sequence of SEQ ID NO: 4 (human EREG) or the region from Val at position 41 to Leu at position 87 of the amino acid sequence of SEQ ID NO: 26 (human TGFα). More preferred examples include antibodies that recognize the region from Gln at position 56 to Leu at position 102 of the amino acid sequence of SEQ ID NO: 4 (human EREG) and the region from Val at position 41 to Leu at position 87 of the amino acid sequence of SEQ ID NO: 26 (human TGFα). The nucleotide sequence of human EREG is shown in SEQ ID NO: 3 and the nucleotide sequence of human TGFα is shown in SEQ ID NO: 25.

In another preferred embodiment, antibodies that bind to EREG and TGFα in the present invention include the antibody of any one of (a) to (d) below:

(a) an antibody that comprises a heavy chain comprising CDR1 having the amino acid sequence of SEQ ID NO: 10, CDR2 having the amino acid sequence of SEQ ID NO: 12, and CDR3 having the amino acid sequence of SEQ ID NO: 14;

(b) an antibody that comprises a light chain comprising CDR1 having the amino acid sequence of SEQ ID NO: 16, CDR2 having the amino acid sequence of SEQ ID NO: 18, and CDR3 having the amino acid sequence of SEQ ID NO: 20;

(c) an antibody that comprises the heavy chain of (a) and the light chain of (b); and (d) an antibody that recognizes the same epitope recognized by the antibody of (c).

The nucleotide sequences of the heavy-chain CDR1, CDR2, and CDR3 are shown in SEQ ID NOs: 9, 11, and 13, respectively. Furthermore, the nucleotide sequences of the light-chain CDR1, CDR2, and CDR3 are shown in SEQ ID NOs: 15, 17, and 19, respectively.

Antibodies that recognize the same epitope recognized by a certain antibody can be obtained, for example, by the following methods.

Whether a test antibody shares the epitope of a certain antibody can be confirmed by checking whether the two antibodies compete for the same epitope. Competition between antibodies can be detected by cross-blocking assay or such. For example, competitive ELISA assay is a preferred cross-blocking assay.

Specifically, in a cross-blocking assay, the wells of a microtiter plate are coated with the EREG protein, and then pre-incubated with or without a candidate competing antibody. Subsequently, an anti-EREG antibody of the present invention is added thereto. The quantity of the anti-EREG antibody of the present invention bound to the EREG protein in the wells indirectly correlates with the binding ability of the candidate competing antibody (test antibody) that competes for binding to the same epitope. More specifically, the greater the affinity the test antibody has for the same epitope, the lower the quantity of the above-mentioned antibody bound to the EREG protein-coated wells and/or the TGFα protein-coated wells. In other words, the greater the affinity the test antibody has for the same epitope, the greater the quantity of the test antibody bound to the EREG protein-coated wells and/or the TGFα protein-coated wells.

The quantity of an antibody bound to the wells can be easily measured by labeling the antibody in advance. For example, a biotin-labeled antibody can be measured using an avidin/peroxidase conjugate and a suitable substrate. In particular, cross-blocking assays using enzyme labels such as peroxidase are called competitive ELISA assays. The antibodies can be labeled with other detectable or measurable labeling substances. More specifically, radiolabels and fluorescent labels are known.

Furthermore, when the test antibody has a constant region derived from a species different from that of the above-described antibody, measurement can be performed for either one of the antibodies bound to the wells using a labeled antibody that recognizes its constant region. If the antibodies are derived from the same species but belong to different classes, the antibodies bound to the wells can be measured using antibodies that distinguish the classes.

If a candidate competing antibody can block the binding of the above-described antibody by at least 20%, preferably at least 20% to 50%, and even more preferably at least 50%, compared to the binding activity obtained in a control experiment performed in the absence of the candidate competing antibody, the candidate competing antibody is either an antibody that binds to substantially the same epitope as the above-described antibody, or an antibody that competes for binding to the same epitope.

In the present invention, antibodies that recognize the same epitope recognized by the antibody of (c) may be antibodies that recognize the EREG epitope recognized by the antibody of (c), or antibodies that recognize the TGFα epitope recognized by the antibody of (c). Preferably, they are antibodies that recognize both the EREG epitope and TGFα epitope recognized by the antibody of (c).

Therefore, antibodies that recognize the same epitope recognized by the antibody of (c) are preferably antibodies that compete with the antibody of (c) for binding to the EREG protein-coated wells or antibodies that compete with the antibody of (c) for binding to the TGFα protein-coated wells in the above-described cross-blocking assay. More preferably, they are antibodies that compete with the antibody of (c) for binding to the EREG protein-coated wells and the antibody of (c) for binding to the TGFα protein-coated wells in the above-described cross-blocking assay.

Antibodies used in the present invention may be derived from any origin, and may be of any type and in any form, as long as they bind to the protein of interest. Specifically, known antibodies such as non-human animal antibodies (for example, mouse antibodies, rat antibodies, and camel antibodies), human antibodies, chimeric antibodies, and humanized antibodies can be used. In the present invention, the antibodies used may be monoclonal or polyclonal antibodies. Monoclonal antibodies are preferred. Furthermore, antibodies used in the present invention are preferably antibodies that specifically bind to the protein of interest.

Antibodies used in the present invention can be obtained as polyclonal or monoclonal antibodies using known techniques. In particular, monoclonal antibodies derived from a mammal are preferable as antibodies used in the present invention. Monoclonal antibodies derived from a mammal include antibodies produced by hybridomas, and antibodies produced by a host transformed with an expression vector containing an antibody gene by genetic engineering techniques.

A monoclonal antibody-producing hybridoma can be basically prepared as follows using a known technique. First, immunization is performed using the EREG protein or TGFα as a sensitizing antigen according to a conventional immunization method. Immunocytes obtained from the immunized animal are then fused to known parent cells by a conventional cell fusion method to obtain hybridomas. Furthermore, a hybridoma that produces the antibody of interest can be selected from these hybridomas by screening cells that produce the antibody using a conventional screening method.

Specifically, monoclonal antibodies are prepared as follows. First, the EREG protein or TGFα protein for use as a sensitizing antigen for antibody production can be obtained by expressing the EREG gene or TGFα gene. Specifically, an EREG- or TGFα-encoding gene sequence is inserted into a known expression vector, and it is used to transform an appropriate host cell. Then, the human EREG protein or human TGFα protein of interest can be purified from the host cell or its culture supernatant using a known method. Alternatively, a purified naturally-derived EREG protein or TGFα protein may also be used. Furthermore, as used in the present invention, a fusion protein produced by fusing a desired partial polypeptide of the EREG protein or TGFα protein with another polypeptide may be used as an immunogen. For example, antibody Fc fragments, peptide tags, or such can be used to produce a fusion protein for use as an immunogen. A vector that expresses the fusion protein can be produced by fusing desired genes encoding two or more types of polypeptide fragments in frame, and inserting the fused genes into an expression vector as described above. Methods for producing fused proteins are described in Molecular Cloning 2nd ed. (Sambrook, J. et al., Molecular Cloning 2nd ed., 9.47-9.58, Cold Spring Harbor Lab. press, 1989).

The EREG protein or TGFα protein purified in this manner can be used as a sensitizing antigen to be used for immunization of mammals. A partial peptide of EREG or TGFα can also be used as a sensitizing antigen. For example, the following peptides can be used as sensitizing antigens:

peptides obtained from the amino acid sequence of the human EREG or TGFα protein by chemical synthesis;
peptides obtained by incorporating a portion of the EREG gene or TGFα gene into an expression vector and expressing it; and
peptides obtained by degrading the EREG protein or TGFα protein with a protease.

There are no limitations on the region of EREG or TGFα used for the partial peptide and its size.

Examples of preferable antigens for obtaining antibodies that bind to EREG and TGFα include polypeptides comprising the region from Gln at position 56 to Leu at position 102 of the amino acid sequence of SEQ ID NO: 4 (human EREG), or the region from Val at position 41 to Leu at position 87 of the amino acid sequence of SEQ ID NO: 26 (human TGFα).

There is no particular limitation on the mammal to be immunized with the sensitizing antigen. To obtain monoclonal antibodies by the cell fusion method, the animal to be immunized is preferably selected in consideration of the compatibility with the parent cells to be used for cell fusion. Generally, rodents are preferred as the animal to be immunized. Specifically, mice, rats, hamsters, or rabbits can be used as the animal to be immunized. In addition, monkeys and such may be used as the animal to be immunized.

The above-described animals can be immunized with a sensitizing antigen according to a known method. For example, as a general method, immunization can be performed by injecting a mammal intraperitoneally or subcutaneously with a sensitizing antigen. Specifically, the sensitizing antigen is administered to mammals several times every four to 21 days. The sensitizing antigen is diluted at an appropriate dilution with PBS (Phosphate-Buffered Saline), physiological saline, or such, and then used for immunization. Furthermore, the sensitizing antigen may be administered together with an adjuvant. For example, the sensitizing antigen can be prepared by mixing with a Freund's complete adjuvant, and then emulsifying it. Furthermore, an appropriate carrier can be used for immunization using the sensitizing antigen. Particularly when a partial peptide with a small molecular weight is used as a sensitizing antigen, the sensitizing antigen peptide is desirably bound to a carrier protein such as albumin or keyhole limpet hemocyanin, and then used for immunization.

Mammals are immunized as described, and after an increase in the amount of desired antibody in the serum is confirmed, immunocytes are collected from the mammals and subjected to cell fusion. A particularly preferred immunocyte is a splenocyte.

A mammalian myeloma cell is used as a cell to be fused with the above-mentioned immunocyte. The myeloma cells preferably comprise a suitable selection marker for screening. A selection marker confers characteristics to cells for their survival (or failure to survive) under a specific culturing condition. Hypoxanthine-guanine phosphoribosyltransferase deficiency (hereinafter abbreviated as HGPRT deficiency), and thymidine kinase deficiency (hereinafter abbreviated as TK deficiency) are known as selection markers. Cells having HGPRT or TK deficiency have hypoxanthine-aminopterin-thymidine sensitivity (hereinafter abbreviated as HAT sensitivity). HAT-sensitive cells cannot carry out DNA synthesis in a HAT selection medium, and are thus killed. However, when the cells are fused with normal cells, they can continue to synthesize DNA using the salvage pathway of the normal cells, and therefore they can grow in the HAT selection medium.

HGPRT-deficient and TK-deficient cells can be selected in a medium containing 6-thioguanine or 8-azaguanine (hereinafter abbreviated as 8AG), and 5'-bromodeoxyuridine, respectively. Normal cells are killed since they incorporate these pyrimidine analogs into their DNA. However, cells that are deficient in these enzymes can survive in the selection medium, since they cannot incorporate these pyrimidine analogs. Alternatively, a selection marker referred to as G418 resistance provides resistance to 2-deoxystreptamine-type antibiotics (gentamycin analogs) from the neomycin-resistance gene. Various types of myeloma cells that are suitable for cell fusion are known. For example, myeloma cells including the following cells can be used to produce the monoclonal antibodies of the present invention:

P3 (P3x63Ag8.653) (J. Immunol. (1979) 123, 1548-1550);
P3x63Ag8U.1 (Current Topics in Microbiology and Immunology (1978) 81, 1-7);
NS-1 (Kohler. G. and Milstein, C. Eur. J. Immunol. (1976) 6, 511-519);
MPC-11 (Margulies. D. H. et al., Cell (1976) 8, 405-415);
SP2/0 (Shulman, M. et al., Nature (1978) 276, 269-270);
FO (de St. Groth, S. F. et al., J. Immunol. Methods (1980) 35, 1-21);
S194 (Trowbridge, I. S. J. Exp. Med. (1978) 148, 313-323); and
8210 (Galfre, G. et al., Nature (1979) 277, 131-133).

Cell fusion of the above-mentioned immunocytes with myeloma cells is essentially performed according to a known method, for example, the method of Kohler and Milstein et al. (Kohler. G. and Milstein, C., Methods Enzymol. (1981) 73, 3-46).

More specifically, the above-mentioned cell fusion can be performed in a standard nutritional culture medium in the presence of, for example, a cell-fusion accelerator. A cell-fusion accelerator may be, for example, polyethylene glycol (PEG), Sendai virus (HVJ), or the like. If desired, an auxiliary agent such as dimethylsulfoxide can be added to further enhance fusion efficiency.

The ratio of immunocytes to myeloma cells used can be established at one's discretion. For example, the number of immunocytes is preferably set to one to ten times of that of myeloma cells. As a medium to be used for the above-mentioned cell fusion, for example, RPMI1640 medium and MEM medium, which are appropriate for the growth of the above-mentioned myeloma cell line, or other standard media that are used for this type of cell culture can be used. Moreover, a serum supplement solution such as fetal calf serum (FCS) can be added to the media.

Cell fusion is performed by thoroughly mixing predetermined amounts of the above-mentioned immunocytes and myeloma cells in the above-mentioned medium, adding and mixing with a PEG solution pre-heated to approximately 37° C., so as to form the desired fused cells (hybridomas). In the cell fusion method, for example, PEG with an average molecular weight of approximately 1000 to 6000 can generally be added at a concentration of 30 to 60% (w/v). Subsequently, the agent for cell fusion or the like which is unfavorable for the growth of hybridomas can be removed by successively adding an appropriate medium such as those listed above, removing the supernatant after centrifugation, and repeating these steps.

Hybridomas obtained in this manner can be selected using a selection medium appropriate for the selection markers carried by myelomas used for cell fusion. For example, cells that have HGPRT and TK deficiencies can be selected by culturing them in a HAT medium (a medium containing hypoxanthine, aminopterin, and thymidine). More specifically, when HAT-sensitive myeloma cells are used for cell fusion, cells that successfully fuse with normal cells can be selectively grown in the HAT medium. Culturing using the above-mentioned HAT medium is continued for a sufficient period of time to kill the cells other than the hybridoma of interest (non-fused cells). More specifically, the hybridoma of interest can be selected, typically by culturing for several days to several weeks. Subsequently, hybridomas that produce the antibody of interest can be screened and monocloned by carrying out a standard limiting dilution method. Alternatively, an EREG- and/or TGFα-recognizing antibody can be prepared using the method described in International Patent Publication No. WO 03/104453.

An antibody of interest can be suitably screened and singly cloned by a screening method based on known antigen-antibody reaction. For example, the antigen is bound to a carrier such as polystyrene beads or the like, or a commercially available 96-well microtiter plate, followed by reaction with the culture supernatant of the hybridomas. Then, after the carrier is washed, it is reacted with an enzyme-labeled secondary antibody or the like. If the antibody of interest that reacts with the sensitizing antigen is contained in the culture supernatant, the secondary antibody will bind to the carrier via the antibody. Ultimately, the presence of the antibody of interest in the culture supernatant can be determined by detecting secondary antibodies bound to the carrier. Hybridomas producing desired antibodies that can bind to the antigen can be cloned by the limiting dilution method or the like. Antigens used for immunization as well as an operably equivalent EREG protein and/or TGFα can be suitably used in this case.

In addition to the above-mentioned method where hybridomas are obtained by immunizing non-human animals with an antigen, an antibody of interest can be obtained by antigen sensitization of human lymphocytes. More specifically, first, human lymphocytes are sensitized with the EREG protein or TGFα protein in vitro. Then, immunosensitized lymphocytes are fused with a suitable fusion partner. For example, human-derived myeloma cells that have infinite division potential can be used as a fusion partner (see Japanese Patent Publication Kokoku Publication No. (JP-B) H01-59878 (examined, approved Japanese patent application published for opposition)). Antibodies obtained by this method are human antibodies that have binding activity to the protein of interest.

Alternatively, antibodies of interest can also be obtained by administering an EREG protein or TGFα protein that serves as an antigen to a transgenic animal having a complete human antibody gene repertoire. Antibody-producing cells of the immunized animal can be immortalized by cell fusion with a suitable fusion partner, or by treatment such as Epstein-Barr virus infection. Human antibodies against the protein of interest can be isolated from the immortalized cells obtained in this manner (see International Patent Publication Nos. WO 94/25585, WO 93/12227, WO 92/03918, and WO 94/02602). Furthermore, cells that produce an antibody having the reaction specificity of interest can be cloned by cloning the immortalized cells. When a transgenic animal is used as the animal to be immunized, the immune system of this animal recognizes human EREG or human TGFα as a foreign substance. Therefore, human antibodies of interest can be readily obtained.

The monoclonal antibody-producing hybridomas produced in this manner can be passaged and cultured in a standard medium. Alternatively, the hybridomas can be stored for a long period in liquid nitrogen.

The hybridomas can be cultured according to a standard method, and the monoclonal antibody of interest can be obtained from the culture supernatants. Alternatively, the hybridomas can be grown by administering them to a compatible mammal, and monoclonal antibodies can be obtained as its ascites. The former method is suitable for obtaining highly purified antibodies.

In the present invention, an antibody encoded by an antibody gene cloned from antibody-producing cells can be used. The cloned antibody gene can be incorporated into a suitable vector and then introduced into a host to express the antibody. Methods for isolating an antibody gene, introducing the gene into a vector, and transforming host cells have been established (see for example, Vandamme, A. M. et al., Eur. J. Biochem. (1990) 192, 767-775).

For example, a cDNA encoding the variable region (V region) of an antibody of interest can be obtained from hybridoma cells producing the antibody of interest. Usually, in order to accomplish this, first, total RNA is extracted from the hybridoma. For example, the following methods can be used as methods for extracting mRNA from cells:
the guanidine ultracentrifugation method (Chirgwin, J. M. et al., Biochemistry (1979) 18, 5294-5299); and
the AGPC method (Chomczynski, P. et al., Anal. Biochem. (1987) 162, 156-159).

The extracted mRNA can be purified using an mRNA purification kit (GE Healthcare Bio-Sciences) or the like. Alternatively, kits for directly extracting mRNAs from cells, such as the QuickPrep mRNA Purification Kit (GE Healthcare Bio-Sciences), are also commercially available. Total RNA can be obtained from the hybridoma by using such kits. A cDNA encoding the antibody V region can be synthesized from the obtained mRNA using reverse transcriptase. cDNA can be synthesized using the AMV Reverse Transcriptase First-strand cDNA Synthesis Kit (SEIKA-GAKU CORPORATION) or the like. To synthesize and amplify cDNA, the SMART RACE cDNA Amplification Kit (Clontech) and the 5'-RACE method using PCR (Frohman, M. A. et al., Proc. Natl. Acad. Sci. USA (1988) 85, 8998-9002; Belyaysky, A. et al., Nucleic Acids Res. (1989) 17, 2919-2932) can be used. Furthermore, in the process of such cDNA synthesis, appropriate restriction enzyme sites, which will be described later, can be introduced into both ends of the cDNA.

The cDNA fragment of interest is purified from the obtained PCR product, and then ligated to a vector DNA. The recombinant vector is prepared in this manner and introduced into *Escherichia coli* or the like, and after colonies are selected, the desired recombinant vector can be prepared from the *E. coli* that formed the colonies. Whether or not the recombinant vector has the cDNA nucleotide sequence of interest can be confirmed by a known method, such as the dideoxynucleotide chain termination method.

In order to obtain genes encoding the variable regions, the 5'-RACE method which uses primers for amplifying the variable region genes is most conveniently utilized. First, a 5'-RACE cDNA library is obtained by synthesizing cDNAs using the RNAs extracted from hybridoma cells as template. It is convenient to use a commercially available kit such as the SMART RACE cDNA amplification kit for the synthesis of 5'-RACE cDNA library.

The antibody genes are amplified by the PCR method using the obtained 5'-RACE cDNA library as a template. Primers for amplifying mouse antibody genes can be designed based on known antibody gene sequences. The nucleotide sequences of these primers vary depending on the subclass of immunoglobulin. Therefore, the subclass is desirably determined in advance using a commercially available kit such as the Iso Strip mouse monoclonal antibody isotyping kit (Roche Diagnostics).

More specifically, when the objective is to obtain genes encoding mouse IgG, one may use primers that can amplify genes encoding γ1, γ2a, γ2b, and γ3 for the heavy chain, and genes encoding the κ chain and λ chain for the light chain. To amplify the IgG variable region genes, generally, a primer that anneals to a portion corresponding to the constant region close to the variable region is used as the 3'-end primer. Meanwhile, a primer contained in the 5'-RACE cDNA library production kit can be used as the 5'-end primer.

Using the PCR products amplified in this manner, immunoglobulins comprising a combination of heavy and light chains can be reconstituted. An antibody of interest can be screened by evaluating the binding activity of the reconstituted immunoglobulins towards EREG and/or TGFα

For example, when the objective is to obtain antibodies against EREG, it is more preferable that the binding of the antibodies to EREG is specific. For instance, it is possible to screen for EREG-binding antibodies as described below:
(1) contacting EREG with an antibody comprising the V region encoded by a cDNA obtained from a hybridoma;
(2) detecting the binding between EREG and the antibody; and
(3) selecting an antibody that binds to EREG.

Methods for detecting the binding between an antibody and EREG are known. Specifically, a test antibody is reacted with EREG immobilized onto a carrier, and then this is reacted with a labeled antibody that recognizes the test antibody. If the labeled antibody on the carrier is detected after washing, this proves that the test antibody binds to EREG. For labeling, enzymatically active proteins such as peroxidase and β-galactosidase, or fluorescent substances such as FITC can be used. To evaluate the binding activity of an antibody, specimens of immobilized EREG-expressing cells can be used.

When the objective is to obtain antibodies against TGFα, it is more preferable that the binding of the antibodies to TGFα is specific. For example, a method similar to the above method for EREG can be carried out for the TGFα-binding antibodies.

Furthermore, when the objective is to obtain antibodies that bind to EREG and TGFα, the binding of the antibodies to EREG and TGFα may be specific to these two proteins. Alternatively, the antibodies may bind to proteins other than these two such as other EGFR ligands. Antibodies that bind to EREG and TGFα can be obtained, for example, by combining the above methods for EREG and TGFα.

Alternatively, for an antibody screening method that evaluates the binding activity, a phage vector-based panning method may be used. When the antibody genes are obtained as libraries of the heavy-chain and light-chain subclasses from polyclonal antibody-expressing cells, phage vector-based screening methods are advantageous. Genes encoding variable regions of the heavy and light chains can be made into a single-chain Fv (scFv) gene by linking the genes via suitable linker sequences. Phages expressing an scFv on their surface can be obtained by inserting a gene encoding the scFv into a phage vector. A DNA encoding an scFv having the binding activity of interest can be collected by contacting the phage with an antigen of interest, and then collecting antigen-bound phage. An scFv having the binding activity of interest can be concentrated by repeating this operation as necessary.

An antibody-encoding polynucleotide of the present invention may encode a full-length antibody or a portion of the antibody. "A portion of an antibody" refers to any portion of an antibody molecule. Hereinafter, the term "antibody fragment" may be used to refer to a portion of an antibody. A preferred antibody fragment of the present invention comprises the complementarity determination region (CDR) of an antibody. More preferably, an antibody fragment of the present invention comprises all of the three CDRs that constitute a variable region.

Once a cDNA encoding the V region of an anti-EREG antibody of interest is obtained, this cDNA is digested with restriction enzymes that recognize the restriction enzyme sites inserted to both ends of the cDNA. A preferred restriction enzyme recognizes and digests a nucleotide sequence that is less likely to appear in the nucleotide sequence constituting the antibody gene. Furthermore, to insert a single copy of the digested fragment into a vector in the correct direction, a restriction enzyme that provides sticky ends is preferred. A cDNA encoding the anti-EREG antibody V region, which has been digested as described above, is inserted into a suitable expression vector to obtain the antibody expression vector. In this step, a chimeric antibody can be obtained by fusing a gene encoding the antibody constant region (C region) with the above-mentioned gene encoding the V region in frame. Herein, "chimeric antibody" refers to an antibody whose constant and variable regions are derived from different origins. Therefore, in addition to interspecies chimeric antibodies such as mouse-human chimeric antibodies, human-human intraspecies chimeric antibodies are also included in the chimeric antibodies of the present invention. A chimeric antibody expression vector can also be constructed by inserting the aforementioned V-region gene into an expression vector into which a constant region gene has been introduced.

More specifically, for example, the restriction enzyme recognition sequence for a restriction enzyme that digests the aforementioned V-region gene can be placed at the 5' end of an expression vector carrying a DNA encoding a desired antibody constant region (C region). The chimeric antibody expression vector is constructed by digesting the two genes using the same combination of restriction enzymes, and fusing them in frame.

To produce an anti-EREG antibody for use in the present invention, the antibody gene can be incorporated into an expression vector so that it is expressed under the regulation of an expression control region. The expression regulatory region for antibody expression includes, for example, an enhancer or a promoter. Then, by transforming suitable host cells with this expression vector, recombinant cells that express the antibody of interest can be obtained.

To express an antibody gene, a DNA encoding the antibody heavy chain (H chain) and a DNA encoding the antibody light chain (L chain) can be incorporated separately into expression vectors. An antibody molecule comprising the H chain and L chain can be expressed by simultaneously transfecting (co-transfecting) the H-chain and L-chain-incorporated vectors into the same host cell. Alternatively, DNAs encoding the H chain and L chain can be incorporated into a single expression vector to transform a host cell with the vector (see International Patent Publication No. WO 94/11523).

Many combinations of hosts and expression vectors for isolating an antibody gene and then introducing the gene into an appropriate host to produce the antibody are known. Any of these expression systems can be applied to the present invention. When using eukaryotic cells as a host, animal cells, plant cells, and fungal cells can be used. More specifically, animal cells that may be used in the present invention are, for example, the following cells:
(1) mammalian cells such as CHO, COS, myeloma, baby hamster kidney (BHK), HeLa, and Vero cells;
(2) amphibian cells such as *Xenopus* oocytes; and
(3) insect cells such as sf9, sf21, Tn5.

In addition, as a plant cell system, an antibody gene expression system using cells derived from the *Nicotiana* genus such as *Nicotiana tabacum* is known. Callus-cultured cells can be used to transform plant cells.

Furthermore, the following cells can be used as fungal cells; yeasts: the *Saccharomyces* genus, for example, *Saccharomyces cerevisiae*, and the *Pichia* genus, for example, *Pichia pastoris*; and filamentous fungi: the *Aspergillus* genus, for example, *Aspergillus niger*.

Antibody gene expression systems that utilize prokaryotic cells are also known. For example, when using bacterial cells, *E. coli* cells, *Bacillus subtilis* cells, and such may be used in the present invention.

Expression vectors comprising the antibody genes of interest are introduced into these cells by transformation. By culturing the transformed cells in vitro, the desired antibodies can be obtained from the transformed cell culture.

In addition to the above host cells, transgenic animals can also be used to produce a recombinant antibody. That is, the antibody can be obtained from an animal into which the gene encoding the antibody of interest is introduced. For example, the antibody gene can be inserted in frame into a gene that encodes a protein produced inherently in milk to construct a fused gene. Goat β-casein or such can be used, for example, as the protein secreted in milk. A DNA fragment containing the fused gene inserted with the antibody gene is injected into a goat embryo, and then this embryo is introduced into a female goat. Desired antibodies can be obtained as a protein fused with the milk protein from milk produced by the transgenic goat born from the goat that received the embryo (or progeny thereof). To increase the volume of milk containing the desired antibody produced by the transgenic goat, hormones can be used on the transgenic goat as necessary (Ebert, K. M. et al., Bio/Technology (1994) 12, 699-702).

Animal-derived antibody C regions can be used for the C regions of a recombinant antibody of the present invention. For example, Cγ1, Cγ2a, Cγ2b, Cγ3, Cμ, Cδ, Cα1, Cα2, and Cε can be used for the mouse antibody H-chain C region, and Cκ and Cλ can be used for the L-chain C region. In addition to mouse antibodies, antibodies of animals such as rats, rabbits, goat, sheep, camels, and monkeys can be used as animal antibodies. Their sequences are known. Furthermore, the C region can be modified to improve the stability of the antibodies or their production.

In the present invention, when administering antibodies to humans, genetically recombinant antibodies that have been artificially modified for the purpose of reducing xenoantigenicity against humans, or the like can be used. Examples of the genetically recombinant antibodies include chimeric antibodies and humanized antibodies. These modified antibodies can be produced using known methods.

A chimeric antibody is an antibody whose variable regions and constant regions are of different origins. For example, an antibody comprising the heavy-chain and light-chain variable regions of a mouse antibody and the heavy-chain and light-chain constant regions of a human antibody is a mouse/human interspecies chimeric antibody. A recombinant vector expressing a chimeric antibody can be produced by ligating a DNA encoding a mouse antibody variable region to a DNA encoding a human antibody constant region, and then inserting it into an expression vector. The recombinant cells that have been transformed with the vector are cultured, and the incorporated DNA is expressed to obtain the chimeric antibody produced in the culture. Human C regions are used for the C regions of chimeric antibodies and humanized antibodies.

For example, Cγ1, Cγ2, Cγ3, Cγ4, Cμ, Cδ, Cα1, Cα2, and Cε can be used as an H-chain C region. Cκ and Cλ can be used as an L-chain C region. The amino acid sequences of these C regions and the nucleotide sequences encoding them are known. Furthermore, the human antibody C region can be modified to improve the stability of an antibody or its production.

Generally, a chimeric antibody consists of the V region of an antibody derived from a non-human animal, and a C region derived from a human antibody. On the other hand, a humanized antibody consists of the complementarity determining region (CDR) of an antibody derived from a non-human animal, and the framework region (FR) and C region derived from a human antibody. Since the antigenicity of a humanized antibody in human body is reduced, a humanized antibody is useful as an active ingredient for therapeutic agents of the present invention.

The antibody variable region generally comprises three complementarity-determining regions (CDRs) separated by four framework regions (FRs). CDR is a region that substantially determines the binding specificity of an antibody. The amino acid sequences of CDRs are highly diverse. On the other hand, the FR-constituting amino acid sequences are often highly homologous even among antibodies with different binding specificities. Therefore, generally, the binding specificity of a certain antibody can be transferred to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known.

Specifically, for example, overlap extension PCR is known as a method for grafting a mouse antibody CDR to a human FR. In overlap extension PCR, a nucleotide sequence encoding a mouse antibody CDR to be grafted is added to the primers for synthesizing a human antibody FR. Primers are prepared for each of the four FRs. It is generally considered that when grafting a mouse CDR to a human FR, selecting a human FR that is highly homologous to a mouse FR is advantageous for maintaining the CDR function. That is, it is generally preferable to use a human FR comprising an amino acid sequence highly homologous to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, overlapping CDR regions of the products synthesized using a human antibody gene as the template are annealed for complementary strand synthesis reaction. By this reaction, human FRs are ligated through the mouse CDR sequences.

The full length of the V-region gene, in which three CDRs and four FRs are ultimately ligated, is amplified using primers that anneal to its 5' and 3' ends and which have suitable restriction enzyme recognition sequences. A vector for human antibody expression can be produced by inserting the DNA obtained as described above and a DNA that encodes a human antibody C region into an expression vector so that they will ligate in frame. After inserting this integration vector into a host to establish recombinant cells, the recombinant cells are cultured, and the DNA encoding the humanized antibody is expressed to produce the humanized antibody in the cell culture (see, European Patent Publication No. EP 239,400, and International Patent Publication No. WO 96/02576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. As necessary, amino acid residues in an FR may be substituted so that the CDRs of a reshaped human antibody form an appropriate antigen-binding site. For example, amino acid sequence mutations can be introduced into FRs by applying the PCR method used for fusing a mouse CDR with a human FR. More specifically, partial nucleotide sequence mutations can be introduced into primers that anneal to the FR sequence. Nucleotide sequence mutations are introduced into the FRs synthesized using such primers. Mutant FR sequences having the desired characteristics can be selected by measuring and evaluating the activity of the amino acid-substituted mutant antibody to bind to the antigen by the above-mentioned method (Sato, K. et al., Cancer Res. 1993, 53, 851-856).

As mentioned above, methods for obtaining human antibodies are also known. For example, human lymphocytes are sensitized in vitro with a desired antigen or cells expressing a desired antigen. Then, by fusing the sensitized lymphocytes with human myeloma cells, desired human antibodies having the antigen-binding activity can be obtained (see JP-B H01-59878). U266 or such can be used as the fusion partner human myeloma cell.

Alternatively, a desired human antibody can be obtained by using a desired antigen to immunize a transgenic animal that comprises the entire repertoire of human antibody genes (see International Patent Publication Nos. WO 93/12227, WO 92/03918, WO 94/02602, WO 94/25585, WO 96/34096, and WO 96/33735). Furthermore, techniques to obtain human antibodies by panning a human antibody library are also known. For example, the V region of a human antibody is expressed as a single chain antibody (scFv) on the phage surface using a phage display method, and phages that bind to the antigen can be selected. By analyzing the genes of selected phages, the DNA sequences encoding the V regions of human antibodies that bind to the antigen can be determined. After determining the DNA sequences of scFvs that bind to the antigen, the V region sequence is fused in frame with the desired human antibody C region sequence, and this is inserted into a suitable expression vector to produce an expression vector. This expression vector can be introduced into suitable expression cells such as those described above, and the human antibody-encoding gene can be expressed to obtain the human antibodies. Such methods are well known (International Patent Publication Nos. WO 92/01047, WO 92/20791, WO 93/06213, WO 93/11236, WO 93/19172, WO 95/01438, and WO 95/15388).

The antibody used in the present invention is not limited to bivalent antibodies represented by IgG, but includes monovalent antibodies and multivalent antibodies represented by IgM, as long as it binds to the protein of interest. The multivalent antibody of the present invention includes a multivalent antibody that has the same antigen binding sites, and a multivalent antibody that has partially or completely different antigen binding sites. The antibody used in the present invention is not limited to the whole antibody molecule, but includes minibodies and modified products thereof, as long as they bind to the protein of interest.

A minibody (low-molecular-weight antibody) contains an antibody fragment lacking a portion of a whole antibody (for example, whole IgG). As long as it has the ability to bind the antigen of interest, partial deletions of an antibody molecule are permissible. Antibody fragments of the present invention preferably contain a heavy-chain variable region (VH) and/or a light-chain variable region (VL). The amino acid sequence of VH or VL may have substitutions, deletions, additions, and/or insertions. Furthermore, as long as it has the ability to bind the antigen of interest, VH and/or VL can be partially deleted. The variable region may be chimerized or humanized. Specific examples of the antibody fragments include Fab, Fab', F(ab')2, and Fv. Specific examples of minibodies include Fab, Fab', F(ab')2, Fv, scFv (single chain Fv), diabody, and sc(Fv)2 (single chain (Fv)2). Multimers of these antibodies (for example, dimers, trimers, tetramers, and polymers) are also included in the minibodies of the present invention.

Fragments of antibodies can be obtained by treating an antibody with an enzyme to produce antibody fragments. Known enzymes that produce antibody fragments are, for example, papain, pepsin, and plasmin. Alternatively, genes encoding these antibody fragments can be constructed, introduced into expression vectors, and then expressed in appropriate host cells (see, for example, Co, M. S. et al., J. Immunol. (1994) 152, 2968-2976; Better, M. and Horwitz, A. H., Methods in Enzymology (1989) 178, 476-496; Plueckthun, A. and Skerra, A., Methods in Enzymology (1989) 178, 476-496; Lamoyi, E., Methods in Enzymology (1989) 121, 652-663; Rousseaux, J. et al., Methods in Enzymology (1989) 121, 663-669; and Bird, R. E. et al., TIBTECH (1991) 9, 132-137).

Digestive enzymes cleave specific sites of an antibody, and yield antibody fragments with the following specific structures.

Papain digestion: F(ab)2 or Fab
Pepsin digestion: F(ab')2 or Fab'
Plasmin digestion: Facb In contrast to the above enzymatically obtained antibody fragments, any portion of an antibody can be deleted when methods that utilize genetic engineering techniques are used.

Therefore, minibodies of the present invention may be antibody fragments from which any region has been deleted, as long as they have binding affinity towards the protein of interest.

Furthermore, in the present invention, the antibodies may retain their effector activity, especially in the treatment of cell proliferative diseases such as cancer. More specifically, the minibodies of the present invention may be antibodies that have both binding affinity towards the protein of interest and effector function. The antibody effector function includes ADCC activity and CDC activity. Therapeutic antibodies of the present invention may have ADCC activity and/or CDC activity for the effector function.

"Diabody" refers to a bivalent minibody constructed by gene fusion (Hollinger P. et al., Proc. Natl. Acad. Sci. USA 90: 6444-6448 (1993); EP 404,097; WO 93/11161; and such). A diabody is a dimer composed of two polypeptide chains. Generally, in each polypeptide chain constituting the dimer, VL and VH are linked by a linker within the same chain. The linker that connects the polypeptide chains in a diabody is generally short enough to prevent binding between VL and VH. Specifically, the amino acid residues constituting the linker are preferably two to twelve residues, more preferably three to ten residues, and particularly preferably five residues or so. Therefore, VL and VH that are encoded by the same polypeptide chain cannot form a single-chain variable region fragment, but form a dimer with another single-chain variable region fragment. As a result, diabodies have two antigen binding sites.

scFv can be obtained by ligating the H-chain V region and L-chain V region of an antibody. In scFv, the H-chain V region and L-chain V region are ligated via a linker, preferably a peptide linker (Huston, J. S. et al., Proc. Natl. Acad. Sci. U.S.A., 1988, 85, 5879-5883). The H-chain V region and L-chain V region of scFv may be derived from any of the antibodies described herein. There is no particular limitation on the peptide linker for ligating the V regions. For example, any single-chain peptide consisting of 3 to 25 residues or so can be used as the linker. More specifically, for example, peptide linkers described below or such can be used.

PCR methods such as those described above can be used for ligating the V regions. For ligation of the V regions by PCR methods, first, a whole DNA or a DNA encoding a desired partial amino acid sequence selected from the following DNAs can be used as a template:
a DNA sequence encoding the H chain or the H-chain V region of the above-mentioned antibody; and
a DNA sequence encoding the L chain or the L-chain V region of the above-mentioned antibody.

DNAs encoding the H-chain and L-chain V regions are individually amplified by PCR methods using a pair of primers that have sequences corresponding to the sequences of both ends of the DNA to be amplified. Then, a DNA encoding the peptide linker portion is prepared. The DNA encoding the peptide linker can also be synthesized using PCR. To the 5' end of the primers used, nucleotide sequences that can be ligated to each of the individually synthesized V-region amplification products are added. Then, PCR reaction is carried out using the "H-chain V region DNA", "peptide linker DNA", and "L-chain V region DNA", and the primers for assembly PCR.

The primers for assembly PCR consist of the combination of a primer that anneals to the 5' end of the "H-chain V region DNA" and a primer that anneals to the 3' end of the "L-chain V region DNA". That is, the primers for assembly PCR are a primer set that can amplify a DNA encoding the full-length sequence of scFv to be synthesized. On the other hand, nucleotide sequences that can be ligated to each V-region DNA are added to the "peptide linker DNA". Thus, these DNAs are ligated, and the full-length scFv is ultimately produced as an amplification product using the primers for assembly PCR. Once the scFv-encoding DNA is constructed, expression vectors containing the DNA, and recombinant cells transformed by these expression vectors can be obtained according to conventional methods. Furthermore, the scFv can be obtained by culturing the resulting recombinant cells and expressing the scFv-encoding DNA.

sc(Fv)2 is a minibody prepared by ligating two VHs and two VLs with linkers or such to form a single chain (Hudson et al., J. Immunol. Methods 1999; 231: 177-189). sc(Fv)2 can be produced, for example, by joining scFvs with a linker.

Moreover, antibodies in which two VHs and two VLs are arranged in the order of VH, VL, VH, and VL ([VH]-linker-[VL]-linker-[VH]-linker-[VL]), starting from the N-terminal side of a single chain polypeptide, are preferred.

The order of the two VHs and the two VLs is not particularly limited to the above-mentioned arrangement, and they may be placed in any order. Examples include the following arrangements:
[VL]-linker-[VH]-linker-[VH]-linker-[VL]
[VH]-linker-[VL]-linker-[VL]-linker-[VH]
[VH]-linker-[VL]-linker-[VH]-linker-[VL]
[VL]-linker-[VL]-linker-[VH]-linker-[VH]
[VL]-linker-[VH]-linker-[VL]-linker-[VH]

Any arbitrary peptide linker can be introduced by genetic engineering, and synthetic linkers (see, for example, those disclosed in Protein Engineering, 9(3), 299-305, 1996) or such can be used as linkers for linking the antibody variable regions. In the present invention, peptide linkers are preferable. There is no particular limitation on the length of the peptide linkers, and it can be suitably selected by those skilled in the art according to the purpose. The length of amino acid residues composing a peptide linker is generally 1 to 100 amino acids, preferably 3 to 50 amino acids, more preferably 5 to 30 amino acids, and particularly preferably 12 to 18 amino acids (for example, 15 amino acids).

Any amino acid sequences composing peptide linkers can be used, as long as they do not inhibit the binding activity of scFv. Examples of the amino acid sequences used in peptide linkers include:

```
Ser

Gly-Ser

Gly-Gly-Ser

Ser-Gly-Gly (SEQ ID NO: 27)
Gly-Gly-Gly-Ser (SEQ ID NO: 28)
Ser-Gly-Gly-Gly (SEQ ID NO: 29)
Gly-Gly-Gly-Gly-Ser (SEQ ID NO: 30)
Ser-Gly-Gly-Gly-Gly (SEQ ID NO: 31)
Gly-Gly-Gly-Gly-Gly-Ser (SEQ ID NO: 32)
Ser-Gly-Gly-Gly-Gly-Gly (SEQ ID NO: 33)
Gly-Gly-Gly-Gly-Gly-Gly-Ser (SEQ ID NO: 34)
Ser-Gly-Gly-Gly-Gly-Gly-Gly (Gly-Gly-Gly-Gly-Ser (SEQ ID NO: 29))n (Ser-Gly-Gly-Gly-Gly (SEQ ID NO: 30))n
``` in which n is an integer of 1 or larger. The amino acid sequences of the peptide linkers can be selected appropriately by those skilled in the art according to the purpose. For example, n, which determines the length of the peptide linkers, is generally 1 to 5, preferably 1 to 3, more preferably 1 or 2.

Therefore, a particularly preferred embodiment of sc(Fv)2 in the present invention is, for example, the following sc(Fv)2:
[VH]-peptide linker (15 amino acids)-[VL]-peptide linker (15 amino acids)-[VH]-peptide linker (15 amino acids)-[VL]

Alternatively, synthetic chemical linkers (chemical crosslinking agents) can be used to link the V regions. Crosslinking agents routinely used to crosslink peptide compounds and such can be used in the present invention. For example, the following chemical crosslinking agents are known. These crosslinking agents are commercially available:
N-hydroxy succinimide (NHS);
disuccinimidyl suberate (DSS);

bis(sulfosuccinimidyl) suberate (BS3);
dithiobis(succinimidyl propionate) (DSP);
dithiobis(sulfosuccinimidyl propionate) (DTSSP);
ethylene glycol bis(succinimidyl succinate) (EGS);
ethylene glycol bis(sulfosuccinimidyl succinate) (sulfo-EGS);
disuccinimidyl tartrate (DST);
disulfosuccinimidyl tartrate (sulfo-DST);
bis[2-(succinimidoxycarbonyloxy)ethyl]sulfone (BSOCOES); and
bis[2-(sulfosuccinimidoxycarbonyloxy)ethyl]sulfone (sulfo-BSOCOES).

Usually, three linkers are required to link four antibody variable regions. The multiple linkers to be used may all be of the same type or different types. In the present invention, a preferred minibody is a diabody or an sc(Fv)2. Such minibody can be obtained by treating an antibody with an enzyme, such as papain or pepsin, to generate antibody fragments, or by constructing DNAs that encode these antibody fragments, introducing them into expression vectors, and then expressing them in appropriate host cells (see, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

Antibodies bound to various types of molecules such as polyethylene glycol (PEG) can also be used as modified antibodies. Moreover, chemotherapeutic agents, toxic peptides, or radioactive chemical substances can be bound to the antibodies. Such modified antibodies (hereinafter referred to as antibody conjugates) can be obtained by subjecting the obtained antibodies to chemical modification. Methods for modifying antibodies are already established in this field. Furthermore, as described below, such antibodies can also be obtained in the molecular form of a bispecific antibody designed using genetic engineering techniques to recognize not only the protein of interest, but also chemotherapeutic agents, toxic peptides, radioactive chemical compounds, or such. These antibodies are included in the "antibodies" of the present invention.

Chemotherapeutic agents that bind to an antibody of the present invention to drive the cytotoxic activity include the following:
azaribine, anastrozole, azacytidine, bleomycin, bortezomib, bryostatin-1, busulfan, camptothecin, 10-hydroxycamptothecin, carmustine, celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine streptozocin, tamoxifen, taxanes, taxol, testosterone propionate, thalidomide, thioguanine, thiotepa, teniposide, topotecan, uracil mustard, vinblastine, vinorelbine, and vincristine.

In the present invention, preferred chemotherapeutic agents are low-molecular-weight chemotherapeutic agents. Low-molecular-weight chemotherapeutic agents are unlikely to interfere with antibody function even after binding to antibodies. In the present invention, low-molecular-weight chemotherapeutic agents usually have a molecular weight of 100 to 2000, preferably 200 to 1000. Examples of the chemotherapeutic agents demonstrated herein are all low-molecular-weight chemotherapeutic agents. The chemotherapeutic agents of the present invention include prodrugs that are converted to active chemotherapeutic agents in vivo. Prodrug activation may be enzymatic conversion or non-enzymatic conversion.

Furthermore, the antibodies can be modified using toxic peptides such as ricin, abrin, ribonuclease, onconase, DNase I, Staphylococcal enterotoxin-A, pokeweed antiviral protein, gelonin, diphtheria toxin, *Pseudomonas* exotoxin, *Pseudomonas* endotoxin, L-asparaginase, and PEG L-Asparaginase. In another embodiment, one or two or more of the low-molecular-weight chemotherapeutic agents and toxic peptides can be combined and used for antibody modification. The bonding between an anti-EREG antibody and the above-mentioned low-molecular weight chemotherapeutic agent may be covalent bonding or non-covalent bonding. Methods for producing antibodies bound to these chemotherapeutic agents are known.

Furthermore, proteinaceous pharmaceutical agents or toxins can be bound to antibodies by gene recombination techniques. Specifically, for example, it is possible to construct a recombinant vector by fusing a DNA encoding the above-mentioned toxic peptide with a DNA encoding an anti-EREG antibody in frame, and inserting this into an expression vector. This vector is introduced into suitable host cells, the obtained transformed cells are cultured, and the incorporated DNA is expressed. Thus, an anti-EREG antibody bound to the toxic peptide can be obtained as a fusion protein. When obtaining an antibody as a fusion protein, the proteinaceous pharmaceutical agent or toxin is generally positioned at the C terminus of the antibody. A peptide linker can be positioned between the antibody and the proteinaceous pharmaceutical agent or toxin.

Furthermore, the antibody used in the present invention may be a bispecific antibody. A bispecific antibody refers to an antibody that carries variable regions that recognize different epitopes within the same antibody molecule.

Preferred examples of bispecific antibodies of the present invention include a bispecific antibody in which one antigen-binding site recognizes EREG, and the other antigen-binding site recognizes TGFα.

Methods for producing bispecific antibodies are known. For example, two types of antibodies recognizing different antigens may be linked to prepare a bispecific antibody. The antibodies to be linked may be half molecules each having an H chain and an L chain, or may be quarter molecules consisting of only an H chain. Alternatively, bispecific antibody-producing fused cells can be prepared by fusing hybridomas producing different monoclonal antibodies. Bispecific antibodies can also be prepared by genetic engineering techniques.

Antibodies of the present invention can be produced by methods known to those skilled in the art as described below.

For example, in the case of mammalian cells, expression can be carried out by operably linking a commonly used effective promoter and an antibody gene to be expressed with a polyA signal on the downstream 3' side thereof. An example of the promoter/enhancer is human cytomegalovirus immediate early promoter/enhancer.

Other promoters/enhancers that can be used for antibody expression include viral promoters/enhancers, or mammalian cell-derived promoters/enhancers such as human elongation factor 1α (HEF1α). Specific examples of viruses whose promoters/enhancers may be used include retrovirus, polyoma virus, adenovirus, and simian virus 40 (SV40).

When an SV40 promoter/enhancer is used, the method of Mulligan et al. (Nature (1979) 277, 108) may be utilized. An HEF1α promoter/enhancer can be readily used for expressing a gene of interest by the method of Mizushima et al. (Nucleic Acids Res. (1990) 18, 5322).

In the case of E. coli, the antibody gene to be expressed is operably linked to an effective commonly used promoter and a signal sequence for antibody secretion to express the gene. Examples of the promoter include the lacZ promoter and araB promoter. When the lacZ promoter is used, the method of Ward et al., (Nature (1989) 341, 544-546; FASEB J. (1992) 6, 2422-2427) may be used. Alternatively, the araB promoter can be used for expressing a gene of interest by the method of Better et al. (Science (1988) 240, 1041-1043).

With regard to the signal sequence for antibody secretion, the pelB signal sequence (Lei, S. P. et al., J. Bacteriol. (1987) 169, 4379) may be used for production in the periplasm of E. coli. As necessary, the antibody structure is refolded by using a protein denaturant like guanidine hydrochloride or urea so that the antibody will have the desired binding activity.

The replication origin inserted into the expression vector includes, for example, those derived from SV40, polyoma virus, adenovirus, or bovine papilloma virus (BPV). In order to amplify the gene copy number in the host cell system, a selection marker can be inserted into the expression vector. Specifically, the following selection markers can be used:
the aminoglycoside transferase (APH) gene;
the thymidine kinase (TK) gene;
the E. coli xanthine guanine phosphoribosyltransferase (Ecogpt) gene;
the dihydrofolate reductase (dhfr) gene, etc.

Any expression system, for example, a eukaryotic cell system or a prokaryotic cell system can be used to produce antibodies used in the present invention. Examples of eukaryotic cells include animal cells such as established mammalian cell system, insect cell system, and filamentous fungus cells and yeast cells. Examples of prokaryotic cells include bacterial cells such as E. coli cells. Antibodies used in the present invention are preferably expressed in mammalian cells. For example, mammalian cells such as CHO, COS, myeloma, BHK, Vero, or HeLa cells can be used.

Then, the transformed host cell is then cultured in vitro or in vivo to induce production of an antibody of interest. The host cells are cultured according to known methods. For example, DMEM, MEM, RPMI 1640, or IMDM can be used as the culture medium. A serum supplement solution such as fetal calf serum (FCS) can also be used in combination.

Antibodies expressed and produced as described above can be purified by using a single known method or a suitable combination of known methods generally used for purifying proteins. Antibodies can be separated and purified by, for example, appropriately selecting and combining affinity columns such as protein A column, chromatography columns such as ion and gel filtration chromatography columns, filtration, ultrafiltration, salt precipitation, dialysis, and such (Antibodies A Laboratory Manual. Ed Harlow, David Lane, Cold Spring Harbor Laboratory, 1988).

Known means can be used to measure the antigen-binding activity of the antibodies (Antibodies A Laboratory Manual. Ed Harlow, David Lane, Cold Spring Harbor Laboratory, 1988). For example, an enzyme linked immunosorbent assay (ELISA), an enzyme immunoassay (EIA), a radioimmunoassay (RIA), or a fluoroimmunoassay can be used.

The antibodies used in the present invention may be antibodies with a modified sugar chain. It is known that the cytotoxic activity of an antibody can be increased by modifying its sugar chain. Known antibodies having modified sugar chains include the following:
antibodies with modified glycosylation (for example, WO 99/54342);
antibodies deficient in fucose attached to sugar chains (for example, WO 00/61739 and WO 02/31140);
antibodies having a sugar chain with bisecting GlcNAc (for example, WO 02/79255), etc.

The antibodies used in the present invention may have cytotoxic activity.

In the present invention, the cytotoxic activity includes, for example, antibody-dependent cell-mediated cytotoxicity (ADCC) activity and complement-dependent cytotoxicity (CDC) activity. In the present invention, CDC activity refers to complement system-mediated cytotoxic activity. ADCC activity refers to the activity of injuring a target cell when a specific antibody attaches to its cell surface antigen. An Fcγ receptor-carrying cell (immune cell, or such) binds to the Fc portion of the antigen via the Fcγ receptor and the target cell is damaged.

An anti-EREG antibody can be tested to see whether it has ADCC activity or CDC activity using known methods (for example, Current Protocols in Immunology, Chapter 7. Immunologic studies in humans, Editor, John E. Coligan et al., John Wiley & Sons, Inc., (1993) and the like).

First, specifically, effector cells, complement solution, and target cells are prepared.

(1) Preparation of Effector Cells

Spleen is removed from a CBA/N mouse or the like, and spleen cells are isolated in RPMI1640 medium (manufactured by Invitrogen). After washing in the same medium containing 10% fetal bovine serum (FBS, manufactured by HyClone), the cell concentration is adjusted to $5 \times 10^6$/mL to prepare the effector cells.

(2) Preparation of Complement Solution

Baby Rabbit Complement (manufactured by CEDARLANE) is diluted 10-fold in a culture medium (manufactured by Invitrogen) containing 10% FBS to prepare a complement solution.

(3) Preparation of Target Cells

The target cells can be radioactively labeled by incubating cells expressing the protein of interest with 0.2 mCi of sodium chromate-$^{51}$Cr (manufactured by GE Healthcare Japan) in a DMEM medium containing 10% FBS for one hour at 37° C. For cells expressing the protein of interest, one may use cells transformed with a gene encoding the protein of interest, primary colon cancer, metastatic colon cancer, lung adenocarcinoma, pancreatic cancer, stomach cancer, kidney cancer cells, colon cancer cells, esophageal cancer cells, stomach cancer cells, pancreatic cancer cells, or such. After radioactive labeling, cells are washed three times in RPMI1640 medium containing 10% FBS, and the target cells can be prepared by adjusting the cell concentration to $2 \times 10^5$/mL.

ADCC activity or CDC activity can be measured by the method described below. In the case of ADCC activity measurement, the target cell and anti-EREG antibody (50 µL each) are added to a 96-well U-bottom plate (manufactured by Becton Dickinson), and reacted for 15 minutes on ice. Thereafter, 100 µL of effector cells are added and incubated in a carbon dioxide incubator for four hours. The final concentration of the antibody is adjusted to 0 or 10 µg/mL. After culturing, 100 µL of the supernatant is collected, and the radioactivity is measured with a gamma counter (COBRAII AUTO-GAMMA, MODEL D5005, manufactured by Packard Instrument Company). The cytotoxic activity (%) can be calculated using the obtained values according to the equation: $(A-C)/(B-C) \times 100$, wherein A represents the radioactivity (cpm) in each sample, B represents the radioactivity (cpm) in a sample where 1% NP-40 (manufactured by Nacalai Tesque) has been added, and C represents the radioactivity (cpm) of a sample containing the target cells only.

Meanwhile, in the case of CDC activity measurement, 50 µL of target cell and 50 µL of an antibody against the protein of interest are added to a 96-well flat-bottomed plate (manufactured by Becton Dickinson), and reacted for 15 minutes on ice. Thereafter, 100 µL of the complement solution is added, and incubated in a carbon dioxide incubator for four hours. The final concentration of the antibody is adjusted to 0 or 3 µg/mL. After incubation, 100 µL of supernatant is collected, and the radioactivity is measured with a gamma counter. The cytotoxic activity can be calculated in the same way as in the ADCC activity determination.

On the other hand, in the case of measuring the cytotoxic activity of an antibody conjugate, 50 µL of target cell and 50 µL of an antibody conjugate against the protein of interest are added to a 96-well flat-bottomed plate (manufactured by Becton Dickinson), and reacted for 15 minutes on ice. This is then incubated in a carbon dioxide incubator for one to four hours. The final concentration of the antibody is adjusted to 0 or 3 µg/mL. After culturing, 100 µL of supernatant is collected, and the radioactivity is measured with a gamma counter. The cytotoxic activity can be calculated in the same way as in the ADCC activity determination.

In the present invention, antagonistic activity against EREG and/or antagonistic activity against TGFα can be measured by methods known to those skilled in the art.

In the present invention, ligand binding of the EGF receptor, which is considered to be the main receptor of EREG or TGFα, results in dimerization of the receptor, and activation of the intracellular tyrosine kinase domain of the receptor. The activated tyrosine kinase forms phosphorylated tyrosine-containing peptides by autophosphorylation, and the peptides associate with various signal transduction accessory molecules. They are mainly PLCγ (phospholipase Cγ), Shc, Grb2, and such. Of these accessory molecules, the former two are further phosphorylated by the EGF receptor tyrosine kinase. The main signal transduction pathway from the EGF receptor is the pathway in which phosphorylation is transduced in the order of Shc, Grb2, Sos, Ras, Raf/MAPK kinase/MAP kinase. Furthermore, an alternative pathway which is from PLCγ to PKC is considered to exist.

Since such intracellular signal cascades vary depending on the cell type, suitable molecules can be targeted in the target cell of interest, and the target molecules are not limited to the above-mentioned factors. Commercially available kits for measuring in vivo signal activation can be suitably used (for example, the protein kinase C activity assay system (GE Healthcare Japan)).

Furthermore, in vivo signaling activation can be detected using as an index, the transcription-inducing effect on a target gene present downstream of the in vivo signaling cascade. Changes in the transcriptional activity can be detected based on the principle of reporter assay. More specifically, a reporter gene such as green fluorescence protein (GFP) or luciferase is positioned downstream of the transcriptional factor or promoter region of the target gene, and the reporter activity is measured. The change in transcriptional activity can be measured based on the reporter activity.

Furthermore, since the EGF receptor usually functions to promote cell proliferation, in vivo signaling activation can be evaluated by measuring the proliferation activity of target cells. In the present invention, the antagonistic activity of a test substance is evaluated by assessing the cell proliferation activity. However, the present invention is not limited to this method, and the activity can be assessed by suitably applying the aforementioned methods to selected target cells.

Specifically, for example, by measuring the below-mentioned cell proliferation activity, the antagonistic activity of a test substance can be evaluated or measured. For example, a method that measures the incorporation of $[^{3}H]$-labeled thymidine added to the medium by living cells as an index of DNA replication ability is used.

As a more convenient method, a dye exclusion method that measures under a microscope the ability of a cell to release a dye such as trypan blue to the outside of the cell, or the MTT method is used. The latter makes use of the ability of living cells to convert 3-(4,5-dimethylthiazol-2-yl)-2,5-diphenyl tetrazolium bromide (MTT), which is a tetrazolium salt, to a blue formazan product. More specifically, a test antibody is added to the culture solution of a test cell, and after a certain period of time, the MTT solution is added to the culture solution, and this is left to stand for a certain time for MTT to be incorporated into the cell. As a result, MTT which is a yellow compound is converted to a blue compound by the action of succinate dehydrogenase in the mitochondria of the cell. After dissolving this blue product for coloration, absorbance is measured and used as an indicator for the number of viable cells.

Besides MTT, reagents such as MTS, XTT, WST-1, and WST-8 are commercially available (Nacalai Tesque, and such) and can be suitably used. Furthermore, methods that evaluate cell proliferation activity using cellular ATP or impedance of cell culture as an indicator are known. In activity measurements, for example, when the test substance is an antibody, an antibody that has the same isotype as the antibody of interest but does not have antagonist activity (for example, an antibody that does not bind to cells expressing an antigen of interest, an antibody that does not bind to an antigen of interest, or such) can be used as a control antibody in the same manner as the antibody of interest. If the antibody of interest has a stronger antagonist activity than the control antibody, it can be determined that the activity is present.

There is no particular limitation on the cells whose proliferation is suppressed by the antagonist, as long as they express an EREG protein, TGFα protein, and/or EGFR. Preferred cells are, for example, cancer cells. Specifically, cells derived from colon cancer, lung adenocarcinoma, pancreatic cancer, stomach cancer, or kidney cancer are suitable cells for the present invention. According to the present invention, an effective cell proliferation-suppressing effect can be obtained for both primary and metastatic foci of these cancers. More preferable cancer cells are cells from primary colon cancer, metastatic colon cancer, lung adenocarcinoma, pancreatic cancer, stomach cancer, and kidney cancer. Therefore, the antibodies of the present invention can be used for the purpose of treating or preventing cell proliferation-induced diseases such as colon cancer, lung adenocarcinoma, pancreatic cancer, stomach cancer, and kidney cancer. These cancers may be targets for the treatment or prevention regardless of whether they are primary foci or metastatic foci. More preferably, antibodies of the present invention can be used for the purpose of treating and/or preventing primary colon cancer, metastatic colon cancer, or pancreatic cancer. Furthermore, of these cancers, cancers that proliferate in an EREG- and/or TGFα-dependent manner are preferred targets for the treatment and/or prevention of the present invention.

The present invention also provides polynucleotides encoding the antibodies of the present invention, and polynucleotides that hybridize under stringent conditions to these polynucleotides and encode antibodies having an activity equivalent to that of the antibodies of the present invention. The present invention also provides vectors containing these polynucleotides and transformants (including transformed cells) containing such vectors.

The polynucleotides of the present invention are polymers comprising multiple nucleotides or base pairs of deoxyribonucleic acids (DNA) or ribonucleic acids (RNA). There is no particular limitation on the polynucleotides as long as they encode the antibodies of the present invention. The polynucleotides of the present invention may also contain non-natural nucleotides.

The polynucleotides of the present invention can be used to express antibodies using genetic engineering techniques. Furthermore, they can be used as probes in the screening of antibodies that are functionally equivalent to the antibodies of the present invention. Specifically, a DNA that hybridizes under stringent conditions to the polynucleotide encoding an antibody of the present invention, and encodes an antibody having an activity equivalent to that of the antibody of the present invention, can be obtained by techniques such as hybridization and gene amplification techniques (for example, PCR), using the polynucleotide encoding an antibody of the present invention, or a portion thereof, as a probe. Such DNAs are included in the polynucleotides of the present invention. Hybridization techniques are well known to those skilled in the art (Sambrook, J. et al., Molecular Cloning 2nd ed., 9.47-9.58, Cold Spring Harbor Lab. press, 1989).

Conditions for hybridization include, for example, low stringency washing conditions. Examples of low stringency conditions include post-hybridization washing under conditions of 2×SSC and 0.1% SDS at room temperature, and preferably under conditions of 0.1×SSC and 0.1% SDS at 42° C. More preferable hybridization conditions include high stringency washing conditions. High stringency conditions include, for example, conditions of 0.5×SSC and 0.1% SDS at 65° C. Under these conditions, higher temperature can be expected to efficiently yield polynucleotides with high homology. However, several factors such as temperature and salt concentration can influence hybridization stringency, and those skilled in the art can suitably select these factors to achieve similar stringencies.

A functionally equivalent antibody encoded by a polynucleotide obtained by these hybridization and gene amplification techniques in the present invention usually has a high homology to the amino acid sequences of the antibodies of the present invention. The antibodies of the present invention also include antibodies that are functionally equivalent to and have high amino acid sequence homology to the antibodies of the present invention. The term "high homology" generally refers to amino acid identity of at least 50% or higher, preferably 75% or higher, more preferably 85% or higher, still more preferably 95% or higher. Polypeptide homology can be determined by the algorithm described in literature (Wilbur, W. J. and Lipman, D. J. Proc. Natl. Acad. Sci. USA (1983) 80, 726-730).

Substances that decrease the expression level of EREG or TGFα can be obtained by methods known to those skilled in the art.

siRNA is a double-stranded RNA in which an RNA complementary to a transcription product of a target gene is bound with an RNA complementary to this RNA. There is no particular limitation on the length of siRNA, but it is preferably a short chain that does not show toxicity in cells. The length of siRNA is usually 15 to 50 base pairs, and preferably 15 to 30 base pairs. The double stranded portions of siRNA are not limited to those that completely match, but they include unpaired portions due to mismatches (corresponding bases are not complementary), bulges (corresponding bases are absent from one of the strands), and such. The end structure of an siRNA may be either a blunt end or a sticky (protruding) end.

Antisense oligonucleotides include antisense RNAs and antisense DNAs. An antisense oligonucleotide is an RNA or DNA that is complementary to a transcription product of a target gene, and is usually single-stranded. There is no particular limitation on the length of an antisense oligonucleotide, but it is usually five to 50 nucleotides, and preferably nine to 30 nucleotides. An antisense oligonucleotide does not have to be completely complementary to a transcription product of a target gene, and may include unpaired portions due to mismatches, bulges, or such. In an embodiment, the antisense RNA includes microRNA (miR). microRNA is a single-stranded RNA that is complementary to a transcription product of a target gene. Generally, microRNA is a small non-coding RNA and acts on an mRNA to induce gene silencing. There is no particular limitation on the length of microRNA, but it is usually ten to 30 nucleotides and preferably 14 to 21 nucleotides.

Pharmaceutical Compositions

In another aspect, the present invention provides pharmaceutical compositions comprising an antibody of the present invention as an active ingredient. In addition, the present invention relates to cell proliferation inhibitors, in particular anticancer agents, comprising an antibody of the present invention as an active ingredient.

In another aspect, the present invention provides pharmaceutical compositions comprising an EREG antagonist and a TGFα antagonist as active ingredients. In addition, the present invention relates to cell proliferation inhibitors, in particular anticancer agents, comprising an EREG antagonist and a TGFα antagonist as active ingredients.

The cell proliferation inhibitors and anticancer agents of the present invention are preferably administered to a subject affected by cancer, or a subject who is likely to be affected by cancer. There is no particular limitation on the type of cancer targeted by the anticancer agents of the present invention. For example, the anticancer agents of the present invention can be used for cancers such as colon cancer, lung adenocarcinoma, pancreatic cancer, stomach cancer, and kidney cancer. The anticancer agents of the present invention can be used against both primary and metastatic foci.

In the present invention, "comprising a certain substance as an active ingredient" means comprising the substance as a major active ingredient, and does not limit the content percentage of the substance.

The pharmaceutical compositions of the present invention can be administered orally or parenterally to a patient. Preferably, the administration is parenteral administration. Specifically, the method of administration is, for example, administration by injection, transnasal administration, transpulmonary administration, or transdermal administration. Examples of administration by injection include systemic and local administrations of a pharmaceutical composition of the present invention by intravenous injection, intramuscular injection, intraperitoneal injection, subcutaneous injection, or such. A suitable administration method may be selected according to the age of the patient and symptoms. The dosage may be selected, for example, within the range of 0.0001 mg to 1000 mg per kg body weight in each administration. Alternatively, for example, the dosage for each patient may be selected within the range of 0.001 to 100,000 mg/body. However, the pharmaceutical composition of the present invention is not limited to these dosages.

The present invention also includes methods for suppressing cell proliferation or methods for treating cancer, which comprise the step of administering a pharmaceutical composition of the present invention to a subject (for example, mammals such as humans).

An EREG antagonist and a TGFα antagonist may be administered simultaneously or at different timings. An EREG antagonist and a TGFα antagonist may be made into a single formulation or different formulations.

The pharmaceutical compositions of the present invention can be formulated according to conventional methods (for example, Remington's Pharmaceutical Science, latest edition, Mark Publishing Company, Easton, U.S.A), and may also contain pharmaceutically acceptable carriers and additives. Examples include, but are not limited to, surfactants, excipients, coloring agents, perfumes, preservatives, stabilizers, buffers, suspending agents, isotonization agents, binders, disintegrants, lubricants, fluidity promoting agents, and flavoring agents; and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methyl cellulose, polyvinylacetal diethylaminoacetate, polyvinylpyrrolidone, gelatin, medium chain fatty acid triglyceride, polyoxyethylene hardened castor oil 60, saccharose, carboxymethyl cellulose, corn starch, inorganic salt, and such.

Screening Methods

The present invention provides methods of screening candidate compounds for cancer therapeutic agents, which comprise the following steps:
(1) measuring the EREG antagonist activity of a test substance;
(2) measuring the TGFα antagonist activity of the test substance; and
(3) selecting a substance that has EREG antagonist activity and TGFα antagonist activity.

The EREG antagonist activity and TGFα antagonist activity can be measured by methods known to those skilled in the art as described above.

Candidate compounds selected by the screening methods of the present invention are useful as candidate anticancer therapeutic agents whose mechanism of action is the suppression of EREG action and TGFα action.

As necessary, candidate compounds selected by the screening methods of the present invention are further evaluated for their effect on other cancer cell lines or primary culture cells, and also for their effect such as toxicity against normal cells. Compounds that are useful as cancer therapeutic agents can be selected through such evaluation. A series of evaluation methods for cancer therapeutic agents are already established.

In the screening methods of the present invention, various naturally-occurring and artificially-synthesized compounds can be used as test compounds. For example, protein libraries and antibody libraries are preferred as the test compound libraries of the present invention. Alternatively, phage libraries presenting proteins or antibodies may be used as the test compounds. Furthermore, libraries of artificially-synthesized compounds such as combinatorial libraries may be used as the test compounds.

The EREG antagonist activity and TGFα antagonist activity can be measured by methods known to those skilled in the art such as the above-mentioned methods, methods of the Examples described herein, or such.

Furthermore, the present invention provides methods for producing cancer therapeutic agents, which comprise the steps of:
(1) selecting a substance having EREG antagonist activity;
(2) selecting a substance having TGFα antagonist activity; and
(3) preparing an anticancer agent by combining the substance selected in (1) and the substance selected in (2).

There is no particular limitation on the substances having EREG antagonist activity. Known substances already known to have EREG antagonist activity may be used, or they may be substances newly obtained using the above-mentioned measurement of antagonist activity measurement or such as an indicator.

There is no particular limitation on the substances having TGFα antagonist activity. Known substances already known to have TGFα antagonist activity may be used, or they may be substances newly obtained using the above-mentioned measurement of antagonistic activity or such as an indicator.

When an anticancer agent is prepared by combining a substance having EREG antagonist activity and a substance having TGFα antagonist activity, there is no limitation on its embodiment as long as the substance having EREG antagonist activity and the substance having TGFα antagonist activity are administered to the same subject. For example, a substance having EREG antagonist activity and a substance having TGFα antagonist activity can be administered as a single pharmaceutical agent or separate pharmaceutical agents. When administered as separate pharmaceutical agents, the substance having EREG antagonist activity and the substance having TGFα antagonist activity may be administered simultaneously or at different timings.

All prior art documents cited herein are incorporated by reference into this description.

EXAMPLES

Herein below, the present invention will be more specifically described with reference to the Examples; however it is not to be construed as being limited thereto.

[Example 1] The Ba/F3 Cell Line Expressing the EGFR/GCSFR Chimeric Receptor Shows Epiregulin-Dependent Proliferation cDNAs of human EGFR (GenBank: NM 005228) and mouse GCSFR (GenBank: NM_007782) were isolated by PCR amplification. A chimeric receptor gene comprising the extracellular domain of EGFR and the intracellular domain of GCSFR was produced. The nucleotide sequence and amino acid sequence of the chimeric receptor are shown in SEQ ID NOs: 1 and 2, respectively. A mammalian expression vector for the chimeric receptor was constructed. In the expression vector, the chimeric receptor gene is designed to be transcribed under the control of a human EF1α promoter. The chimeric receptor expression vector has a Geneticin-resistance gene.

Ba/F3 cells were transformed using a linearized chimeric receptor expression vector. Cells into which the vector was introduced were selected in the presence of Geneticin. The selected cells were maintained in a medium supplemented with EGF instead of IL3. The objective was to retain the characteristics of the cells to proliferate in a manner dependent on chimeric receptor signals.

A luciferase expression vector was introduced into the chimeric receptor-expressing cells. The objective was to allow detection of cell proliferation based on luciferase activity. A luciferase gene (pGL3-Control Vector, Promega) was incorporated into a mammalian cell expression vector carrying a Zeocin-resistance marker. In the expression vector, luciferase is designed to be transcribed under the control of a mouse CMV promoter. Cells were transformed using a linearized luciferase expression vector. After selection of cells in the presence of Zeocin and Geneticin, cells having high luciferase activity were selected. Hereinafter, Ba/F3 cells expressing the chimeric receptor and luciferase will be referred to as "EGF(R)". EGF(R) was maintained in RPMI 1640 medium containing 10% fetal calf serum, EGF, Geneticin, and Zeocin.

EGF(R) was observed to undergo cell proliferation depending on addition of human Epiregulin (EREG). EGF(R) was centrifuged and resuspended in RPMI 1640 medium containing 10% FBS. The cells were seeded into a 96-well plate at $1\times10^4$ cells/well. Human EREG (R&D Systems) was added to the culture solution at a final concentration of interest, and this was incubated at 37° C. under 5% $CO_2$ for four days. The cell number was determined after incubation based on the following two enzyme activities. Cell Count Reagent SF (Nacalai Tesque), a WST-8 reagent, was used to measure dehydrogenase activity. The method was carried out according to the protocol indicated by the manufacturer. The absorbance was measured using the plate reader, Benchmark Plus (BIO-RAD). Luciferase activity was measured using the Steady-Glo Luciferase Assay System (Promega). The method was performed according to the protocol indicated by the manufacturer. Chemiluminescence was measured using the multilabel counter, Wallac 1420 Arvo SX (Perkin-Elmer). FIG. 1 shows that similar growth curves were obtained by measurements using WST-8 and luciferase activity. EGF(R) proliferated remarkably as the EREG concentration increases. The above-mentioned results were consistent with the cell count observed under a microscope.

[Example 2] EREG-Expressing Cells Activate EGFR Chimeric Receptors on the Cell Surface EREG cDNA (NM_001432) shown in SEQ ID NO: 3 was cloned into the mammalian expression vector pMCN. pMCN is capable of expressing a foreign gene under the control of a mouse CMV promoter (GenBank: U68299). The pMCN vector carries a Geneticin-resistance gene. The CHO DG44 cell line (Invitrogen) was transformed with the EREG expression vector. Drug-resistant cells were selected in the presence of Geneticin. The EREG/DG cell line stably expressing the EREG protein was isolated.

Whether EREG-expressing cells can activate EGF(R) proliferation was tested. EREG/DG and EGF(R) were cocultured, and the EGF(R) cell count was determined based on luciferase activity. Whether the activation of EGF(R) proliferation was induced by EREG was also tested. When coculturing EREG/DG and EGF(R), an anti-EREG neutralizing antibody (EP20 or EP27; WO2008047723) or the anti-EGFR neutralizing antibody cetuximab (Merck KGaA) was added thereto.

EREG/DG cells were suspended in αMEM medium containing 10% FBS (Invitrogen), and the cells were spread onto a 96-well plate at $1\times10^4$ cells/well. The cells were incubated at 37° C. overnight under 5% $CO_2$, and they adhered onto the plate. After removing the culture solution, $1\times10^4$ EGF(R) cells suspended in RPMI 1640 containing 10% FBS were added thereto together with the antibody. Incubation was carried out for three days.

Figure 2:
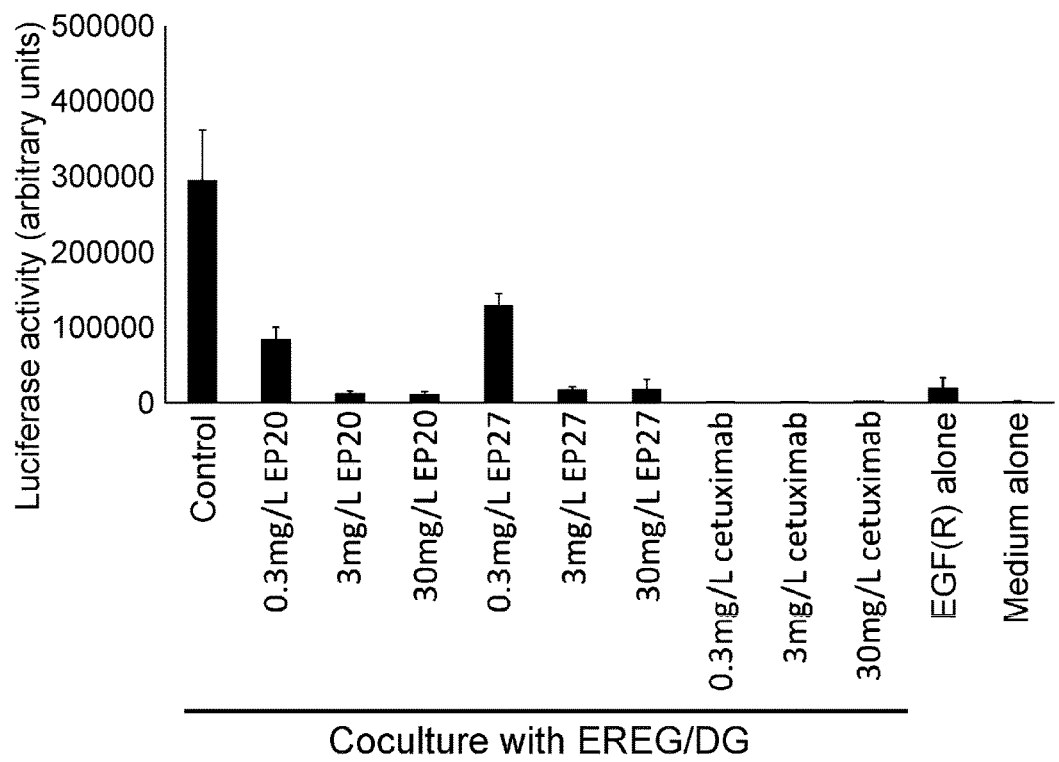
FIG. 2 shows that EGF(R) proliferation was promoted by coculture with EREG/DG. The promoted proliferation was abolished by addition of an anti-EREG antibody or anti-EGFR antibody.

FIG. 2 shows the luciferase activity, i.e., the EGF(R) cell count, under the respective conditions. This shows that EGF(R) proliferation is promoted by coculture with EREG/DG, and this promotion is cancelled out by antibody addition. Compared to the culture condition without EREG/DG44 cells (EGF(R) alone), coexistence with EREG/DG44 cells (control) allowed remarkable promotion of EGF(R) cell proliferation. The cell proliferation promoted by the coexistence with EREG/DG44 cells was suppressed by addition of an anti-EREG or anti-EGFR antibody. The above-mentioned results show that EREG-expressing cells induce signal activation of nearby EGFR-expressing cells. Cancellation by the anti-EREG antibodies shows that EREG is involved in signal activation.

[Example 3] EGF(R) Proliferation is Promoted by Coexistence with the Colon Cancer DLD-1 Cell Line. This Promotion of Proliferation is Cancelled Out by Addition of an Anti-EREG Neutralizing Antibody and Anti-TGF-α Neutralizing Antibody.

Multiple EGF ligands may be involved in EGFR activation in cancer cells. If multiple ligands are involved in receptor activation, suppression of only one ligand is not sufficient for complete suppression of receptor activation. In DLD-1, expression of mRNAs of AREG and TGFα in addition to EREG is enhanced. Analysis was carried out to determine which molecule of the EGF ligands expressed in DLD-1 is involved in EGFR receptor activation. EGF(R) and DLD-1 were cocultured in the presence of a neutralizing antibody. Ligands involved in EGF(R) activation were identified by monitoring the proliferation of EGF(R).

DLD-1 cells were suspended in RPMI 1640 medium containing 10% FBS, and spread onto a 96-well plate at $2\times10^3$ cells/well. The cells were incubated at 37° C. overnight under 5% $CO_2$, and then the culture supernatant was removed. $1\times10^4$ EGF(R) cells suspended in RPMI 1640 containing 10% FBS were added thereto together with the antibodies having neutralizing activity. After three days of incubation, the cell count was quantified by measuring luciferase activity.

Figure 3:
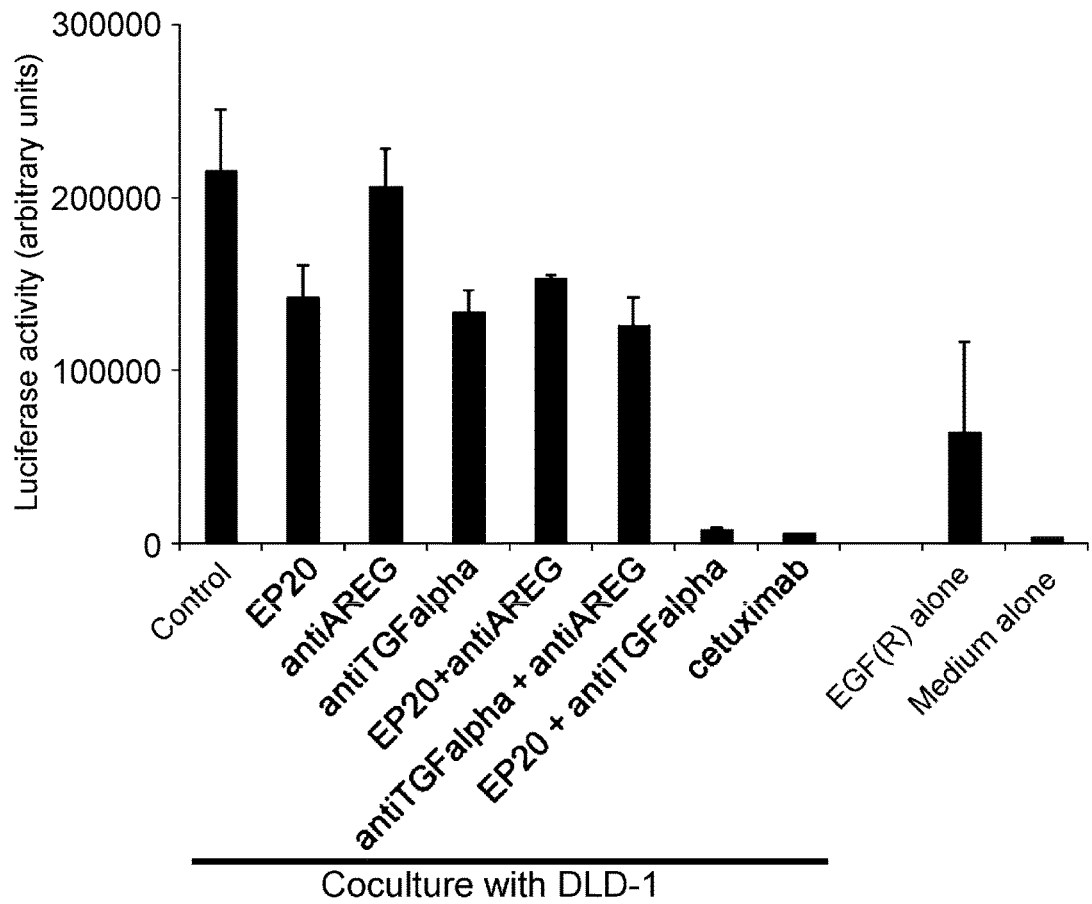
FIG. 3 shows that EGF(R) proliferation was promoted by coculture with DLD-1. The promoted proliferation was abolished by addition of both an anti-EREG antibody and an anti-TGFα antibody, or addition of an anti-EGFR antibody.

EGF(R) proliferation was promoted by coculture with DLD-1 cells (FIG. 3; "Control" versus "EGF(R) alone"). Addition of the anti-EGFR antibody cetuximab almost completely abolished the promotion of EGF(R) proliferation by DLD-1. It was proven that the promotion of EGF(R) proliferation by DLD-1 cells is mediated by an EGFR stimulus.

The anti-TGFα antibody (R&D Systems, AB-239-NA) partially suppressed EGF(R) proliferation promoted by coculture with DLD-1. The anti-EREG antibody EP20 partially suppressed proliferation of the cells. The anti-AREG antibody (R&D Systems, MAB262) did not suppress the proliferation at all.

The effect obtained by simultaneous addition of the anti-EREG antibody and anti-AREG antibody was equivalent to the effect produced by the anti-EREG antibody alone. When the anti-TGFα antibody and anti-AREG antibody were added simultaneously, the suppression of EGF(R) proliferation was not stronger than the suppression by the anti-TGFα antibody alone.

On the other hand, simultaneous addition of the anti-EREG antibody and anti-TGFα antibody almost completely abolished the promotion of EGF(R) proliferation by DLD-1. This suppression effect by the two antibodies was equivalent to the effect by the anti-EGFR antibody.

The above results showed that of the EGF ligands expressed in DLD-1, the molecules contributing to EGFR activation are EREG and TGFα.

Figure 8:
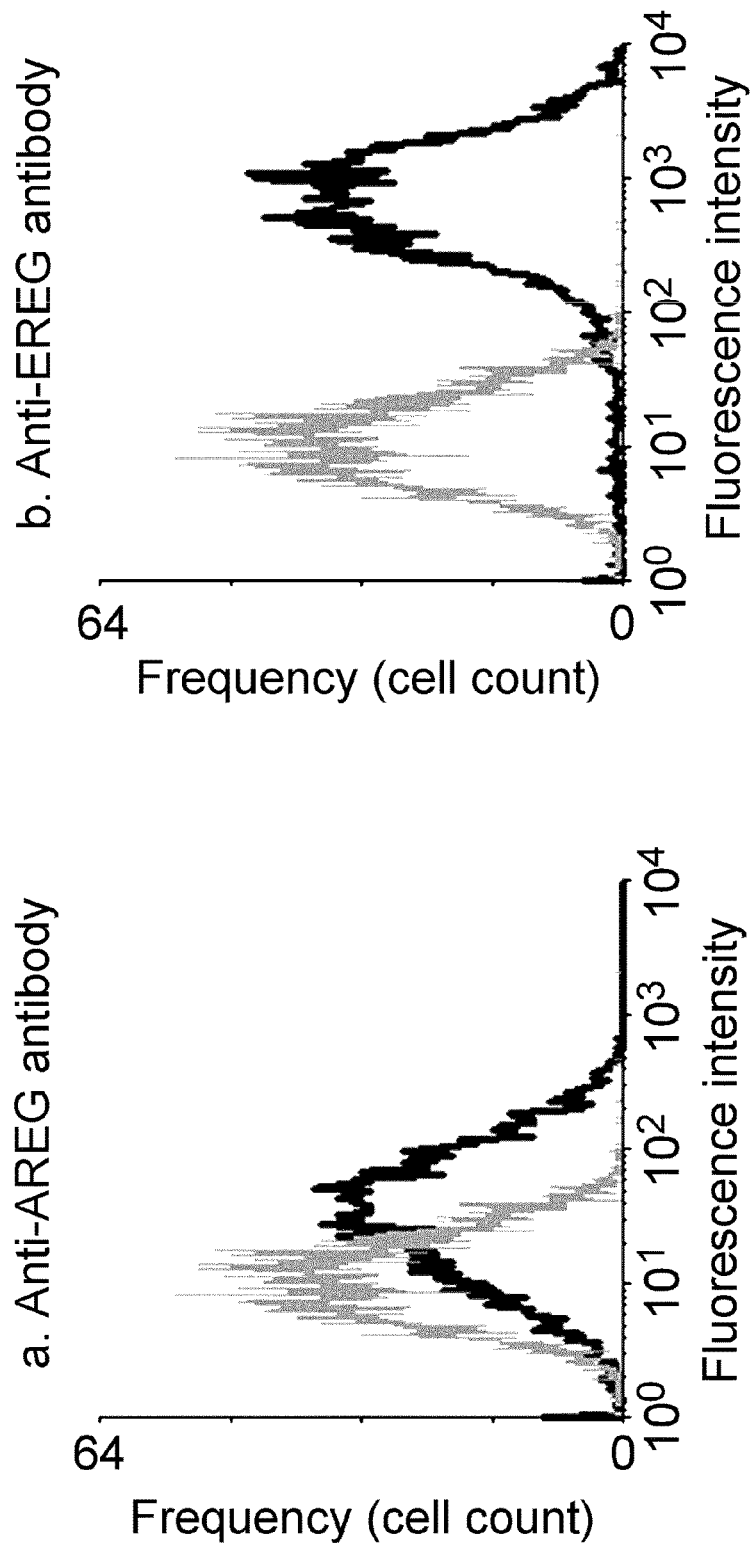
FIG. 8 shows detection of the AREG protein and EREG protein on the surface of DLD-1 cells by the flow cytometry method.

FIG. 8 shows the flow cytometry analysis of the AREG protein and EREG protein on DLD-1 cells. DLD-1 was detached from culture dishes by treatment with PBS/1 mM EDTA. The cells were centrifuged, and the cell pellet was resuspended in PBS containing 1% FBS. The anti-EREG antibody (EP20) and anti-AREG antibody were respectively added to the cell resuspension solution at a final concentration of 4 µg/mL. Incubation was carried out on ice for 30 minutes. After incubation, unreacted antibodies were removed by centrifugation and resuspension. The FITC-labeled anti-mouse IgG antibody (Beckman Coulter, IM0819) was added to the cell suspension solution obtained after washing, and this was incubated on ice for 30 minutes. After centrifugation and resuspension, the cells were analyzed on the flow cytometer FACS Calibur. The results showed that the AREG protein and EREG protein are expressed on DLD-1.

[Example 4] The Anti-EGREG Antibody and Anti-TGFα Antibody Suppress the Proliferation of DLD-1

Whether the proliferation of DLD-1 is suppressed by blocking EGFR signals was analyzed. DLD-1 was suspended in RPMI 1640 containing 10% FBS, and the cells were seeded onto 96-well plates at 2×10³ cells/well. To weaken the scaffold-dependent proliferation ability, low adherence Costar® 3595 plates were used. After addition of each type of neutralizing antibody (10 µg/mL) and Campto (Yakult) which is a topoisomerase inhibitor, the cells were incubated at 37° C. under 5% $CO_2$. The antitumor effect of Cetuximab has been reported to be enhanced when used in combination with a topoisomerase inhibitor (Ciardiello et al. Clin Cancer Res 5:909-916, 1999). After incubation for three days, cell proliferation was quantified by the WST-8 assay method.

Figure 4:
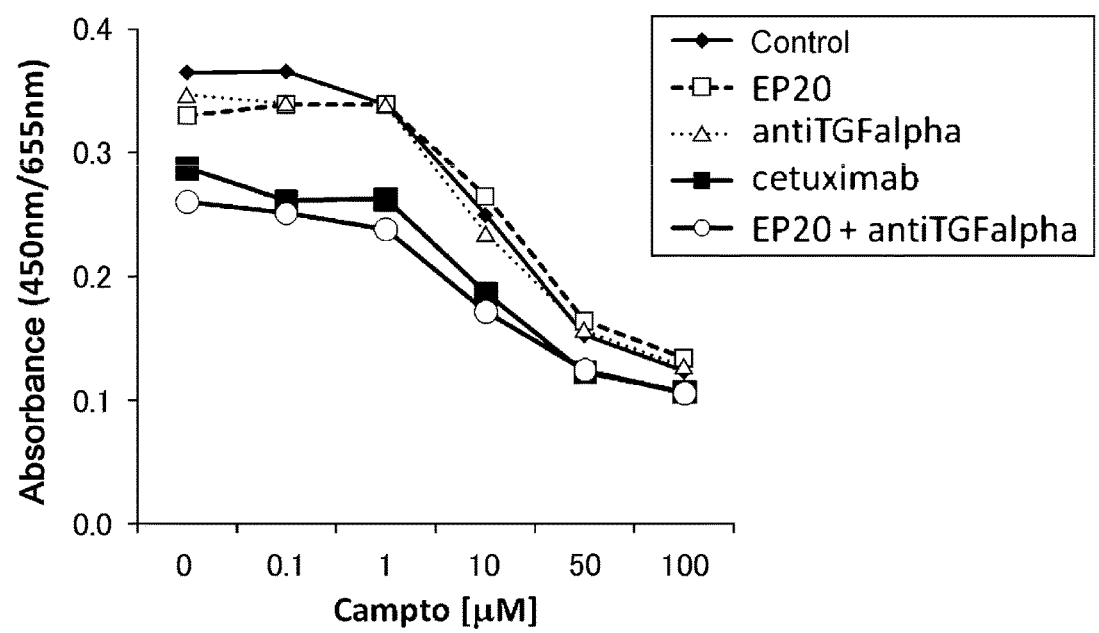
FIG. 4 shows that DLD-1 proliferation was suppressed by addition of both an anti-EREG antibody and an anti-TGFα antibody, or addition of an anti-EGFR antibody. The horizontal axis shows the concentration of the topoisomerase inhibitor Campto added to the culture medium.

Without Campto or in the presence of Campto at a low concentration, cetuximab suppressed the proliferation of DLD-1 cells compared to the control (FIG. 4). EP20 or the anti-TGFα antibody did not suppress the proliferation when it was used alone. Simultaneous addition of the two antibodies suppressed the proliferation of DLD-1 to the same extent as cetuximab. It was found that the proliferation of colon cancer cells is suppressed by simultaneous neutralization of endogenously expressed EREG and TGFα by antibody addition.

It is not necessary to specify the ligand involved in a pharmaceutical agent which inhibits EGFR receptor function. This is because EGFR inhibitors block all ligand stimuli. The drawbacks of the inhibitors are side effects. EGFR is expressed throughout the body. It is reported that EGFR inhibitors currently used in the clinic frequently cause side effects severe enough to necessitate interruption of treatment, such as skin disorders. Rather than cutting off all possibilities of EGFR activation by a receptor inhibitor, the approach of suppressing only ligands involved in EGFR activation in cancer should lead to reduction of side effects while maintaining the maximum antitumor effect from signal blocking.

[Example 5] The EP19 Monoclonal Antibody Binds to Both EREG and TGFα

Figure 5:
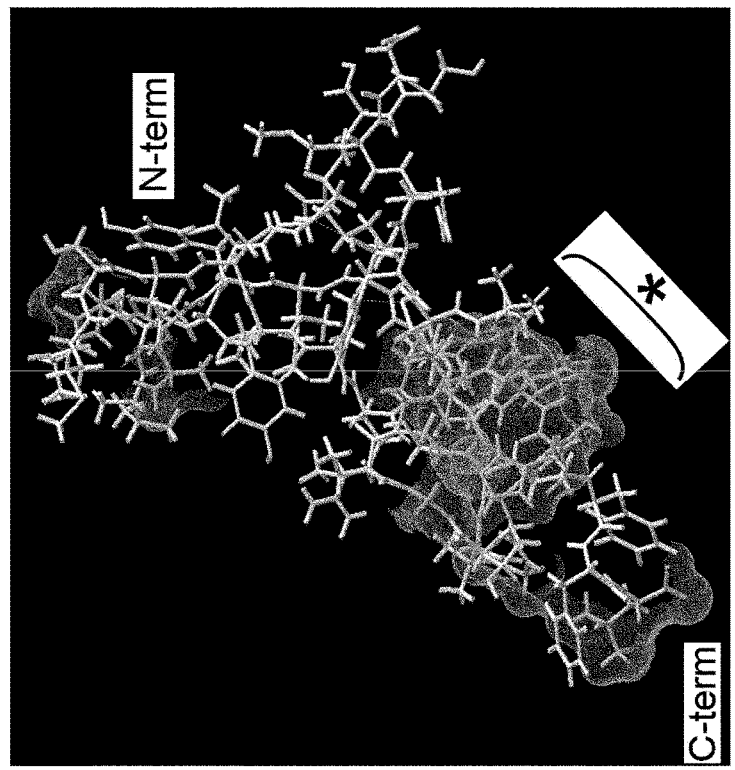
FIG. 5 shows an alignment of the EGF domain sequences of human EREG and human TGFα (SEQ ID NOs: 35 and 36, respectively) in the upper panel. The lower panel shows mapping of the amino acid residues conserved in EREG and TGFα on the conformation of EREG (PDB: 1K37). The symbol "*" in the conformation diagram indicates the region where the amino acids conserved between EREG and TGFα are clustered.

EREG and TGFα are members of the EGF ligand family. As shown in FIG. 5, there are few amino acid residues conserved between EREG and TGFα except for Cys which forms a disulfide bond. Due to the small number of amino acids conserved between the two proteins, it is generally thought that an antibody that specifically binds to both EREG and TGFα does not exist. Based on the conformational analysis of EREG, the present inventors discovered that common three-dimensional structural epitopes are formed by the few amino acid residues conserved between EREG and TGFα (FIG. 5). A very small portion of the antibodies that bind to EREG were considered to also bind to TGFα. The present inventors showed that multiple anti-EREG antibodies were obtained in the application WO 2008/047723. Whether the antibodies obtained in the Examples of the application WO 2008/047723 bind to TGFα was analyzed. The binding was assessed by adding the anti-EREG antibodies to Nunc immunoplates onto which TGFα (R&D Systems, 239-A) was immobilized. Only one of the 37 monoclonal antibodies analyzed—the EP19 antibody bound to TGFα.

Figure 6:
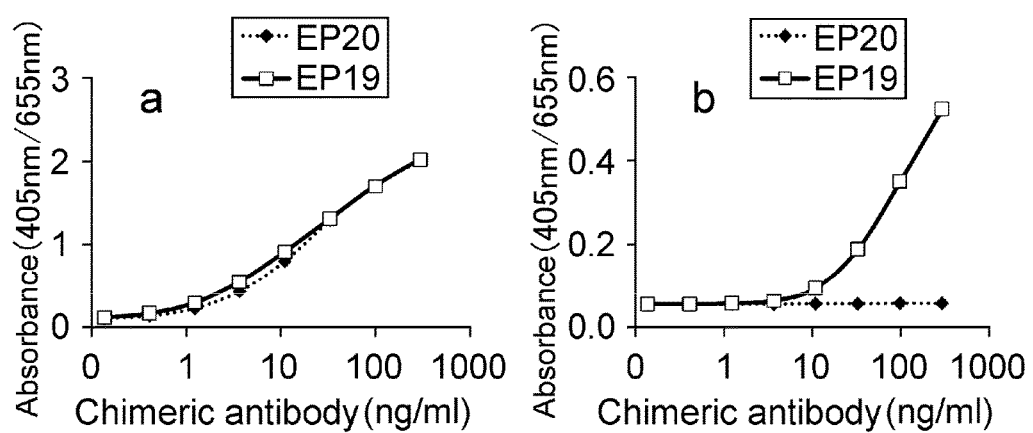
FIG. 6 shows that the anti-EREG chimeric antibody EP19 bound to EREG and TGFα.

A SMART 5'-RACE cDNA library was prepared from the total RNA of an EP19-antibody-producing hybridoma. The total RNA was prepared using an RNeasy Mini column. The cDNA library was prepared according to the manufacturer's instructions. Primers complementary to the antibody constant region sequences were used to amplify the antibody variable region sequences (VH and VL) by PCR. The PCR-amplified fragments were cloned into pCR2.1TOPO, and the nucleotide sequences were determined. The nucleotide sequence of the H-chain variable region is shown in SEQ ID NO: 5, and its translated sequence (amino acid sequence) is shown in SEQ ID NO: 6. The nucleotide sequence of the L-chain variable region is shown in SEQ ID NO: 7, and its translated sequence (amino acid sequence) is shown in SEQ ID NO: 8. An expression vector of a chimeric antibody that comprises these VH and VL sequences and the human IgG1 constant region sequence was constructed. The nucleotide sequence of the chimeric antibody heavy chain is shown in SEQ ID NO: 21, and its amino acid sequence is shown in SEQ ID NO: 22. The nucleotide sequence of the chimeric antibody light chain is shown in SEQ ID NO: 23, and its amino acid sequence is shown in SEQ ID NO: 24. The expression vector was introduced into COS-7, and the chimeric antibody was transiently expressed. The chimeric antibody in the COS7 culture supernatant was confirmed to bind to EREG and TGFα by the following method. The concentration of the chimeric antibody in the culture supernatant was calculated by the sandwich ELISA method. A purified chimeric antibody comprising a different mouse variable region sequence was used as a standard. EREG or TGFα was immobilized onto a Nunc immunoplate, and binding of the chimeric antibodies to the immobilized protein was analyzed. The EP19 recombinant chimeric antibody bound to EREG and TGFα in a dose-dependent manner (FIG. 6). The EP20 recombinant chimeric antibody bound to EREG but not to TGFα at all. Very interestingly, the commercially available anti-TGFα polyclonal antibody (R&D System, AB-2390-NA: lot T06) did not bind to the EREG protein.

[Example 6] EREG Expression is Induced by EGFR Activation

Figure 7:
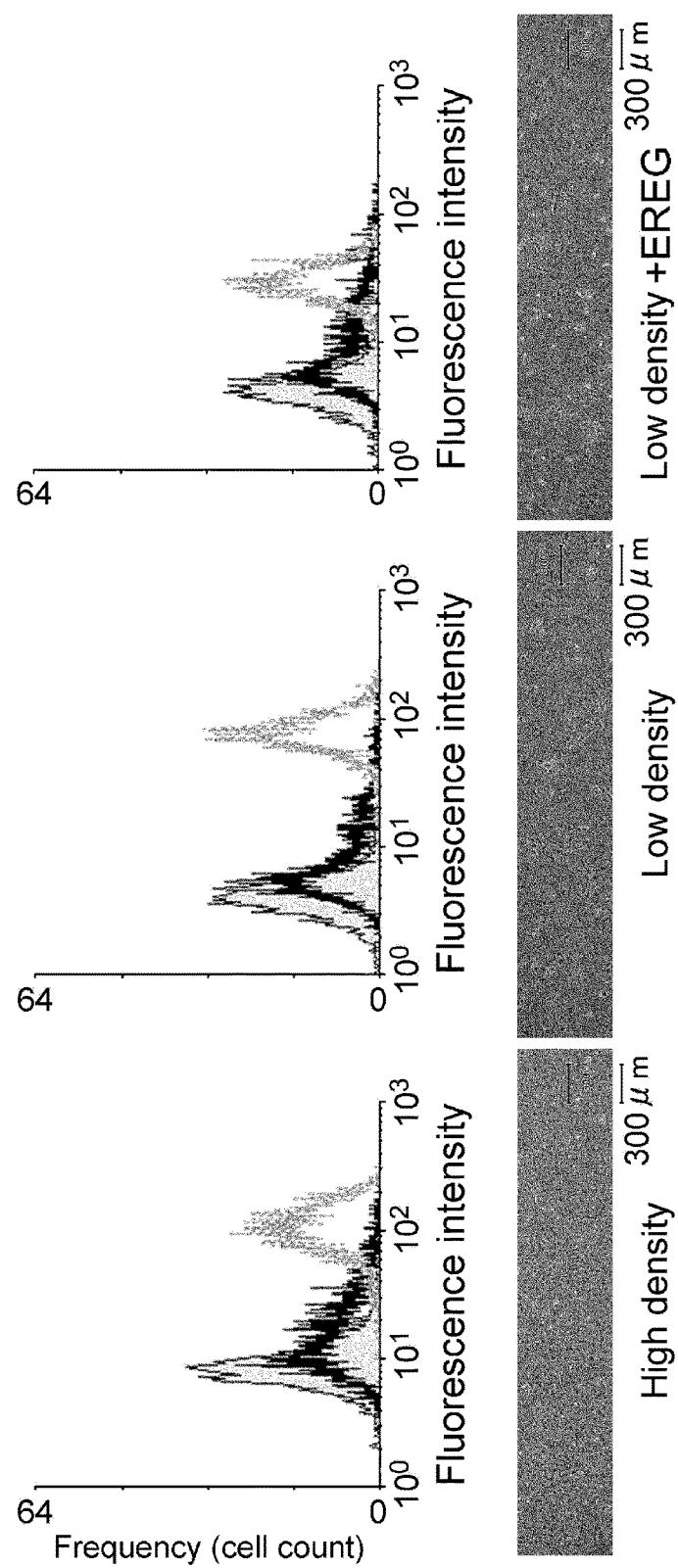
FIG. 7 shows that cell-surface EREG increased in Caki1 as the cell density increased. EREG expression was also induced by addition of soluble EREG at low density. The upper panel shows the results of flow cytometry analysis on the cell-membrane EREG protein (thick lines) and EGFR protein (dashed lines). The lower panel contains photographs showing cell confluency.

The regulation of EREG expression in the kidney cancer cell line Caki1 was analyzed. The number of EREG proteins on the surface of Caki1 cells was coincidentally found to change depending on the cell culture conditions. Caki1 was maintained in MEM (Invitrogen) medium containing 10% FBS. Cells were seeded at $0.3 \times 10^4$ to $1.5 \times 10^4$ cells/cm$^2$, and incubated for two to three days. After incubation, the cells were detached using PBS/EDTA. The cells were centrifuged, and the cell pellet was resuspended in PBS containing 1% FBS. The anti-EREG antibody (EP20) or anti-EGFR antibody (cetuximab) was added to the cell resuspension solution at a final concentration of 4 µg/mL. This was incubated on ice for 30 minutes. After incubation, unreacted antibodies were removed by centrifugation and resuspension. An FITC-labeled secondary antibody was added to the cell suspension solution after washing, and this was incubated on ice for 30 minutes. The cells were subjected to centrifugation and resuspension, and then the expressions of EREG and EGFR proteins were analyzed using the flow cytometer FACS Calibur (FIG. 7).

When the cell density was increased to the extent that there is contact between adjacent cells, the number of EREG protein on the cell membrane was increased. When soluble EREG was added under low cell density conditions, the number of EREG protein on the cell membrane was increased. The number of EREG protein on the cell membrane also increased when EGF was added. The above-mentioned results show that EREG expression was induced via EGFR signal activation, which suggests the presence of a positive feedback mechanism of EGFR signal activation. When EGFR activation was induced by addition of a soluble ligand, the number of EGFR molecules on the cell membrane was decreased. On the other hand, under conditions in which the increase in EREG expression is observed when the cell density is increased, decrease in the number of EGFR molecules was not observed. Addition of a soluble ligand has been reported to cause EGFR activation, and simultaneously incorporation of EGFR into cells. EGFR signals are also activated by stimulation with membrane-associated ligands; however, activated EGFR bound to a membrane-associated ligand may not be incorporated into cells. Most cancer cells express both EGFR and EGF ligands. It was speculated that the membrane-associated ligand EREG is involved in the mechanism of maintaining constitutive EGFR signal activation in cancer cells that stuck mutually.

[Example 7] Preparation of a Recombinant TGFα Protein

A human TGFα cDNA was amplified by PCR from a cDNA library of the human colon cancer cell line DLD-1, and then isolated. A DNA (SEQ ID NO: 38) encoding the chimeric protein human TGFα-Fc (SEQ ID NO: 37), which comprises sequences of the human TGFα extracellular region and a mouse IgG2a antibody constant region, was prepared, and this was cloned into the mammalian expression vector pMCN. pMCN is a vector that allows expression of a foreign gene under the control of a mouse CMV promoter (GenBank: U68299). The pMCN vector has a Geneticin-resistance gene. DG44 cells were transformed with a linearized expression vector by the electroporation method. Cells into which the vector was introduced were selected in the presence of Geneticin. Cells that produce the recombinant protein at a high level were selected by determining the quantity of Fc protein in the culture supernatant.

The protein of interest was purified from a culture supernatant of an Fc fusion protein-producing cell line using Protein G affinity column chromatography and gel filtration chromatography. The concentration of the purified protein was determined by DC protein assay (Bio-Rad) using IgG of known concentrations as the standard.

An *Escherichia coli* expression vector for the thioredoxin/mature human TGFα fusion protein (SEQ ID NO: 39, the polynucleotide sequence is shown in SEQ ID NO: 40) was constructed by inserting the TGFα DNA fragment into pET32a (Novagen). Hereinafter, the thioredoxin/mature human TGFα fusion protein will be abbreviated as "TrxT-GFA". BL21(DE) was transformed with the expression vector. Expression of the fusion protein was induced by IPTG addition. The fusion protein was purified from the soluble fraction of this *E. coli* using Q Sepharose FF and the HisTrap column (GE Healthcare). The expected molecular weight of the purified protein was confirmed using SDS-PAGE. The protein concentration was determined by DC protein assay.

[Example 8] Isolation of an Anti-TGFα Antibody that has Neutralizing Ability

Balb/c mice (Charles river Japan) were immunized with TGFα-Fc. More specifically, at the time of initial immunization, an antigen emulsion was produced using Freund's complete adjuvant (Beckton Dickinson), and the antigen protein was administered subcutaneously at 0.1 mg human TGFα-Fc/head. Two weeks after the immunization, an antigen emulsion produced using Freund's incomplete adjuvant was administered subcutaneously at a dose of 0.05 mg/head once a week for a total of seven times. 0.05 mg of the antigenic protein was administered intravenously to mice in which an increased serum antibody titer was observed. After three days, their spleen cells were obtained, and mixed with mouse myeloma P3-X63Ag8U1 cells (ATCC) at a cell number ratio of approximately 3:1. Then, cell fusion was performed by the polyethylene glycol (PEG) method. After removing PEG by centrifugation, the cells were suspended in RPMI 1640 medium containing 1×HAT media supplement (Sigma), 0.5×BM-Condimed H1 Hybridoma Cloning Supplement (Roche Diagnostics), and 10% fetal calf serum, and the cell concentration was adjusted. Next, the cells were seeded onto a 96-well plate. After hybridoma colony formation was confirmed, the presence of an anti-TGFα antibody in the culture supernatant was analyzed by ELISA using a human TGFα-Fc-coated plate. Hybridoma cells contained in the positive wells were cloned by the limiting dilution method, and anti-TGFα antibody-producing hybridoma lines were isolated. The isotypes of the monoclonal antibodies were determined using IsoStrip (Roche Diagnostics). IgG monoclonal antibodies were purified from the culture supernatants of the established hybridomas by Protein G affinity chromatography and desalting treatment. The concentrations of the purified antibodies were determined by DC protein assay.

Figure 9:
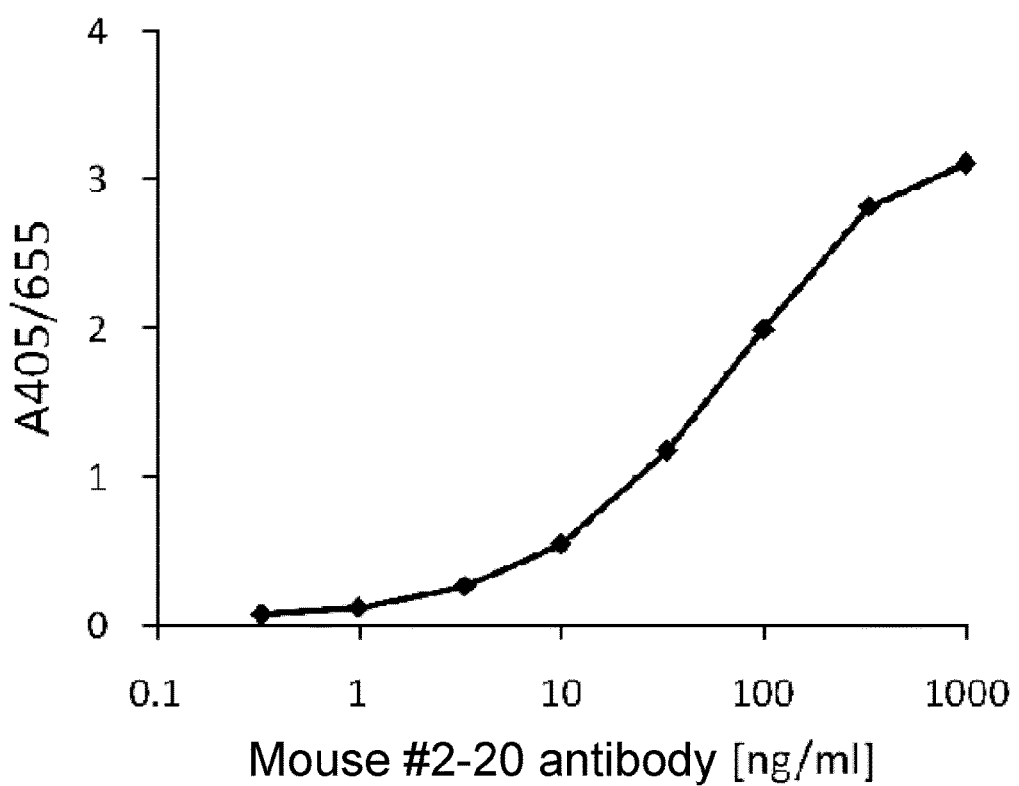
FIG. 9 shows that the mouse #2-20 antibody bound to TGFα.

One of the multiple anti-TGFα antibodies isolated—the #2-20 antibody bound to mature TGFα and had neutralizing activity. Mature TGFα (R&D Systems, 239-A) was immobilized onto a Nunc immunoplate. Binding of the #2-20 antibody to TGFα immobilized onto the plate was analyzed by the ELISA method. FIG. 9 shows that the mouse hybridoma antibody #2-20 binds to mature TGFα in a dose-dependent manner.

Figure 10:
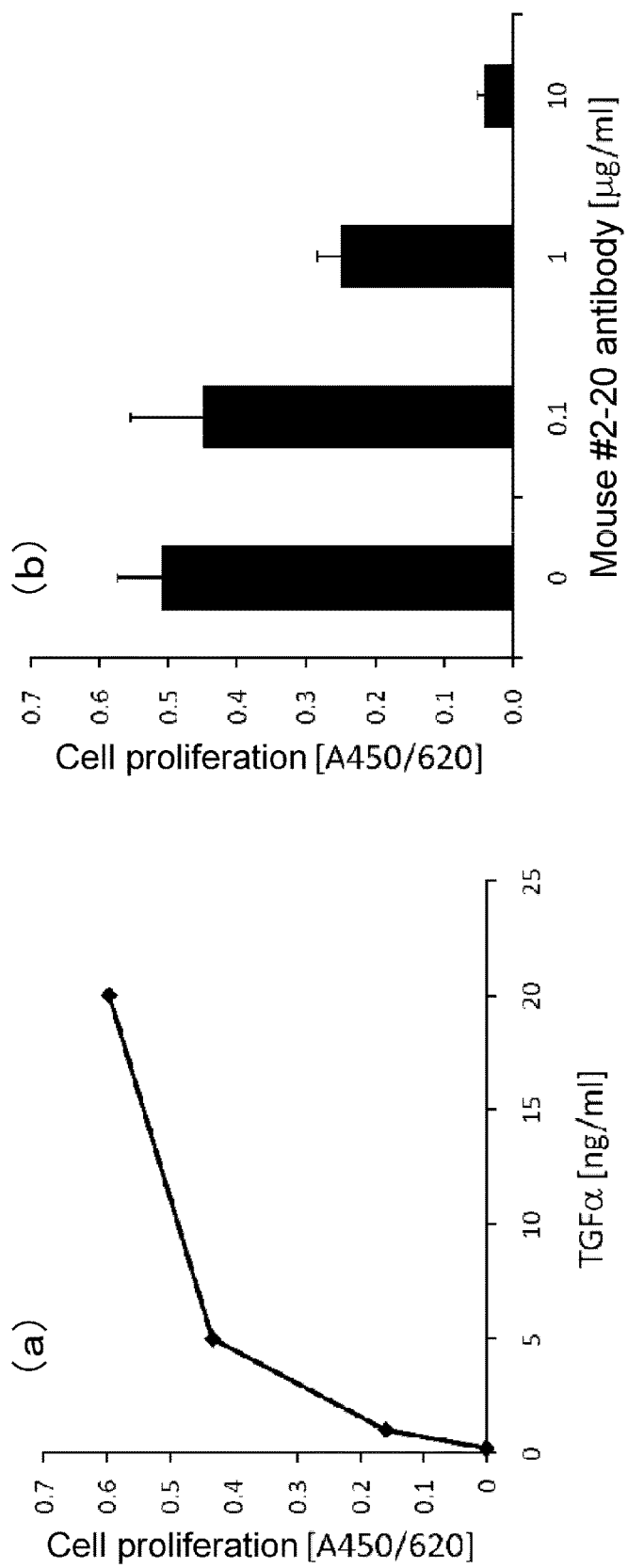
FIG. 10 shows that EGF(R) cells proliferated by addition of TGFα (a); and EGF(R) cell proliferation by TGFα was neutralized by addition of the mouse #2-20 antibody (b).

EGF(R), which are Ba/F3 cells that express the EGFR/GCSFR chimeric receptor, proliferated depending on the concentration of mature TGFα added (FIG. 10, left). EGF(R) cells suspended in RPMI 1640 containing 10% FBS were seeded onto a 96-well culture plate at $5\times10^3$ cells/well. After adding TGFα thereto at an appropriate final concentration, the plate was incubated at 37° C. under 5% $CO_2$ for three days. Cell proliferation was quantified using Cell Count Reagent SF (Nacalai Tesque).

Proliferation of EGF(R) cells by TGFα was neutralized by addition of the #2-20 antibody. EGF(R) cells suspended in RPMI 1640 containing 10% FBS were seeded onto a culture plate at $5\times10^3$ cells/well. First, the #2-20 antibody was added to the cell suspension solution at a final concentration of 0, 0.1, 1, or 10 μg/mL, and then TGFα was added to each well of the culture plate at a final concentration of 5 ng/mL. After incubating the culture plate at 37° C. under 5% $CO_2$ for three days, cell proliferation was quantified. Addition of the #2-20 antibody abolished the TGFα-mediated cell proliferation (FIG. 10, right).

Figure 11:
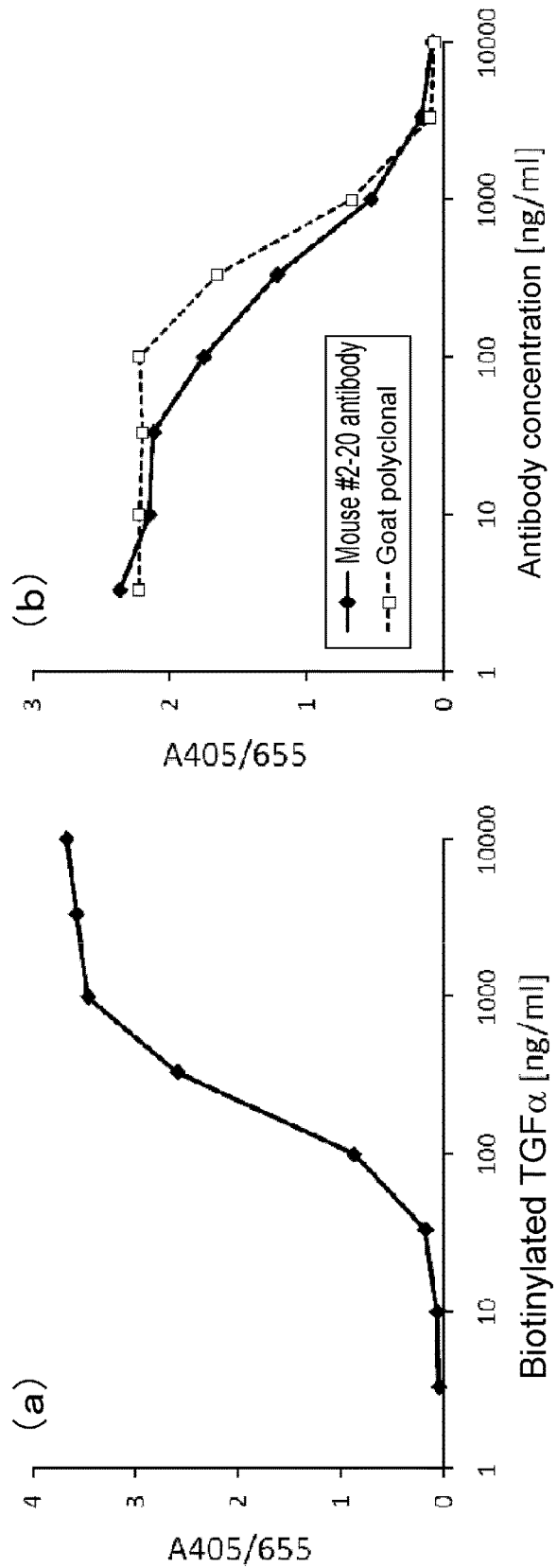
FIG. 11 shows that biotinylated TGFα bound to the soluble EGFR protein (a); and the binding of biotinylated TGFα to the soluble EGFR protein was inhibited by the mouse #2-20 antibody and a goat polyclonal anti-TGFα antibody (b).

Whether the mouse hybridoma #2-20 antibody inhibits the binding of TGFα to EGFR was analyzed. The soluble EGFR-Fc protein (SEQ ID NO: 41, the polynucleotide sequence is shown in SEQ ID NO: 42) was prepared by the method described in International Publication WO 2008/047914. TrxTGFA was biotinylated using the Biotin Protein Labeling Kit (Roche Diagnostics). The EGFR-Fc protein was added at a concentration of 1 μg/mL to a Nunc immunoplate coated with an anti-human antibody, and the protein was captured on the plate. After washing the plate, biotinylated TrxTGFA was added to each well of the plate at an appropriate concentration, and this plate was incubated for one hour. The quantity of TGFα bound to the EGFR protein was quantified by adding an alkaline phosphatase-labeled streptavidin (Zymed) and the alkaline phosphatase substrate Sigma 104. Biotinylated TrxTGFA bound to the EGFR protein in a dose-dependent manner (FIG. 11, left). The activity of the #2-20 antibody to inhibit binding between TGFα and EGFR was tested. The #2-20 antibody or an anti-TGFα goat polyclonal antibody (R&D Systems, AB-239-NA) was added at an appropriate final concentration to a plate onto which the EGFR protein was captured. Subsequently, biotinylated TrxTGFA was added at a final concentration of 50 ng/mL. After incubation for one hour, the quantity of TGFα bound to EGFR was determined. The binding of TGFα to the EGFR protein was inhibited by addition of the mouse #2-20 antibody and the goat polyclonal anti-TGFα antibody (FIG. 11, right).

A Smart 5'-RACE cDNA library (Clontech) was produced from the total RNA of a hybridoma that produces the anti-TGFα antibody #2-20. The total RNA was prepared using the RNAeasy Mini column (Qiagen). The cDNA library was produced according to the manufacturer's instructions. Primers complementary to the antibody constant region sequences were used to amplify the antibody variable region sequences (VH and VL) by PCR. The PCR-amplified fragments were cloned into pCR2.1TOPO, and its nucleotide sequence was determined. The H-chain variable region nucleotide sequence is shown in SEQ ID NO: 43, and its translated sequence (amino acid sequence) is shown in SEQ ID NO: 44. The L-chain variable region nucleotide sequence is shown in SEQ ID NO: 45, and its translated sequence (amino acid sequence) is shown in SEQ ID NO: 46. The antibody heavy-chain CDR1, CDR2, and CDR3 sequences are shown in SEQ ID NOs: 47, 48, and 49, respectively. The antibody light-chain CDR1, CDR2, and CDR3 sequences are shown in SEQ ID NOs: 50, 51, and 52, respectively.

An expression vector of a chimeric antibody comprising the above VH and VL sequences and a human IgG1 constant region sequence was constructed. The polynucleotide sequence and amino acid sequence of the chimeric antibody heavy chain are shown in SEQ ID NO: 53 and SEQ ID NO: 54, respectively. The polynucleotide sequence and amino acid sequence of the chimeric antibody light chain are shown in SEQ ID NO: 55 and SEQ ID NO: 56, respectively. An expression vector of mouse chimeric IgG2a recombinant antibody, which comprises the VH and VL sequences and a mouse IgG2a constant region sequence, was constructed. The polynucleotide sequence and amino acid sequence of the mouse recombinant antibody heavy chain are shown in SEQ ID NO: 57 and SEQ ID NO: 58, respectively. The polynucleotide sequence and amino acid sequence of the mouse recombinant antibody light chain are shown in SEQ ID NO: 59 and SEQ ID NO: 60, respectively. The light-chain and heavy-chain DNAs were both incorporated into a single mammalian cell expression vector, and they are transcribed under the control of mouse CMV promoters. The chimeric antibody expression vector was introduced into COS-7 cells using the FuGENE6 transfection reagent (Roche Diagnostics), and the recombinant antibody was transiently expressed. The concentration of the chimeric antibody in the COS-7 culture supernatant was calculated by the sandwich ELISA method. Herein, a human chimeric antibody and mouse IgG2a of known concentrations were used as standards for the calculation of concentrations.

Figure 12:
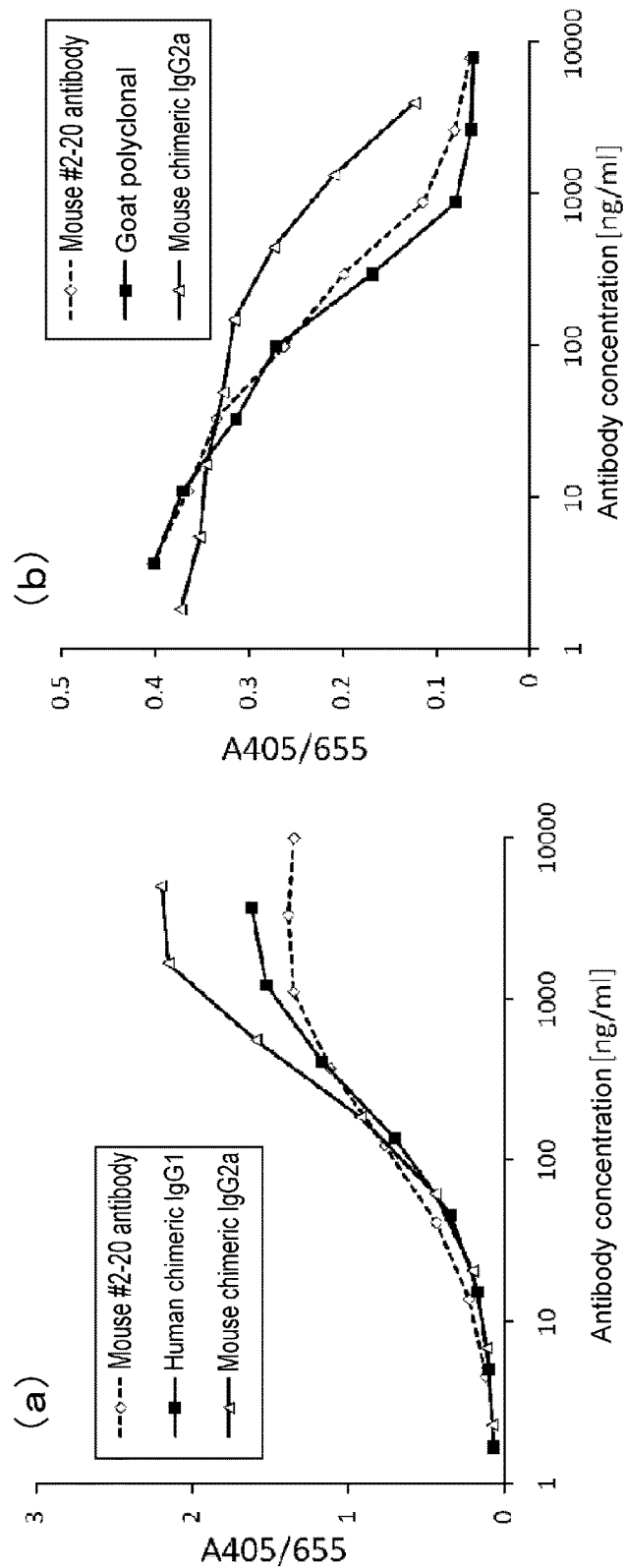
FIG. 12 shows that the recombinant antibodies bound to TGFα (a); and the recombinant antibodies inhibited the binding of biotinylated TGFα to the EGFR protein (b).

The ability of the recombinant antibodies to bind TGFα and their activity to inhibit the binding between TGFα and EGFR were evaluated by the above-described methods. The recombinant human chimeric antibody and the mouse IgG2a antibody bound to mature TGFα (FIG. 12, left). The recombinant mouse chimeric IgG2a antibody inhibited the binding of biotinylated TrxTGFA to the EGFR protein (FIG. 12, right).

INDUSTRIAL APPLICABILITY

The present invention enables cancer therapy that maintains maximal drug efficacy while reducing side effects compared to blocking receptors.

The invention claimed is:

1. A method for treating a disease originated from receptor activation by epiregulin (EREG) and transforming growth factor α (TGFα), comprising administering to a patient a therapeutically effective amount of an antibody that binds to EREG and TGFα, wherein the antibody recognizes the region from Gln at position 56 to Leu at position 102 of SEQ ID NO:4 (human EREG) and the region from Val at position 41 to Leu at position 87 of SEQ ID NO:26 (human TGFα), wherein the disease is cancer.

2. The method of claim 1, wherein the antibody comprises a heavy chain comprising a CDR1 having the amino acid sequence of SEQ ID NO: 10, a CDR2 having the amino acid sequence of SEQ ID NO: 12, and a CDR3 having the amino acid sequence of SEQ ID NO: 14, and a light chain comprising a CDR1 having the amino acid sequence of SEQ ID NO: 16, a CDR2 having the amino acid sequence of SEQ ID NO: 18, and a CDR3 having the amino acid sequence of SEQ ID NO: 20.

3. The method of claim 1, wherein proliferation of a cell expressing EREG and TGFα is suppressed.

* * * * *

SEQUENCE LISTING

<160> NUMBER OF SEQ ID NOS: 108

<210> SEQ ID NO 1
<211> LENGTH: 2580
<212> TYPE: DNA
<213> ORGANISM: Artificial

<220> FEATURE:
<223> OTHER INFORMATION: an artificially synthesized sequence
<220> FEATURE:
<221> NAME/KEY: CDS
<222> LOCATION: (1)..(2580)

<400> SEQUENCE: 1

```
atg cga ccc tcc ggg acg gcc ggg gca gcg ctc ctg gcg ctg ctg gct      48
Met Arg Pro Ser Gly Thr Ala Gly Ala Ala Leu Leu Ala Leu Leu Ala
1               5                   10                  15 gcg ctc tgc ccg gcg agt cgg gct ctg gag gaa aag aaa gtt tgc caa      96
Ala Leu Cys Pro Ala Ser Arg Ala Leu Glu Glu Lys Lys Val Cys Gln
            20                  25                  30 ggc acg agt aac aag ctc acg cag ttg ggc act ttt gaa gat cat ttt     144
Gly Thr Ser Asn Lys Leu Thr Gln Leu Gly Thr Phe Glu Asp His Phe
        35                  40                  45 ctc agc ctc cag agg atg ttc aat aac tgt gag gtg gtc ctt ggg aat     192
Leu Ser Leu Gln Arg Met Phe Asn Asn Cys Glu Val Val Leu Gly Asn
    50                  55                  60 ttg gaa att acc tat gtg cag agg aat tat gat ctt tcc ttc tta aag     240
Leu Glu Ile Thr Tyr Val Gln Arg Asn Tyr Asp Leu Ser Phe Leu Lys
65                  70                  75                  80 acc atc cag gag gtg gct ggt tat gtc ctc att gcc ctc aac aca gtg     288
Thr Ile Gln Glu Val Ala Gly Tyr Val Leu Ile Ala Leu Asn Thr Val
                85                  90                  95 gag cga att cct ttg gaa aac ctg cag atc atc aga gga aat atg tac     336
Glu Arg Ile Pro Leu Glu Asn Leu Gln Ile Ile Arg Gly Asn Met Tyr
            100                 105                 110 tac gaa aat tcc tat gcc tta gca gtc tta tct aac tat gat gca aat     384
Tyr Glu Asn Ser Tyr Ala Leu Ala Val Leu Ser Asn Tyr Asp Ala Asn
        115                 120                 125 aaa acc gga ctg aag gag ctg ccc atg aga aat tta cag gaa atc ctg     432
Lys Thr Gly Leu Lys Glu Leu Pro Met Arg Asn Leu Gln Glu Ile Leu
    130                 135                 140 cat ggc gcc gtg cgg ttc agc aac aac cct gcc ctg tgc aat gtg gag     480
His Gly Ala Val Arg Phe Ser Asn Asn Pro Ala Leu Cys Asn Val Glu
145                 150                 155                 160 agc atc cag tgg cgg gac ata gtc agc agt gac ttt ctc agc aac atg     528
Ser Ile Gln Trp Arg Asp Ile Val Ser Ser Asp Phe Leu Ser Asn Met
                165                 170                 175 tcg atg gac ttc cag aac cac ctg ggc agc tgc caa aag tgt gat cca     576
Ser Met Asp Phe Gln Asn His Leu Gly Ser Cys Gln Lys Cys Asp Pro
            180                 185                 190 agc tgt ccc aat ggg agc tgc tgg ggt gca gga gag gag aac tgc cag     624
Ser Cys Pro Asn Gly Ser Cys Trp Gly Ala Gly Glu Glu Asn Cys Gln
        195                 200                 205 aaa ctg acc aaa atc atc tgt gcc cag cag tgc tcc ggg cgc tgc cgt     672
Lys Leu Thr Lys Ile Ile Cys Ala Gln Gln Cys Ser Gly Arg Cys Arg
    210                 215                 220 ggc aag tcc ccc agt gac tgc tgc cac aac cag tgt gct gca ggc tgc     720
Gly Lys Ser Pro Ser Asp Cys Cys His Asn Gln Cys Ala Ala Gly Cys
225                 230                 235                 240 aca ggc ccc cgg gag agc gac tgc ctg gtc tgc cgc aaa ttc cga gac     768
Thr Gly Pro Arg Glu Ser Asp Cys Leu Val Cys Arg Lys Phe Arg Asp
                245                 250                 255 gaa gcc acg tgc aag gac acc tgc ccc cca ctc atg ctc tac aac ccc     816
Glu Ala Thr Cys Lys Asp Thr Cys Pro Pro Leu Met Leu Tyr Asn Pro
            260                 265                 270 acc acg tac cag atg gat gtg aac ccc gag ggc aaa tac agc ttt ggt     864
Thr Thr Tyr Gln Met Asp Val Asn Pro Glu Gly Lys Tyr Ser Phe Gly
        275                 280                 285
```

```
gcc acc tgc gtg aag aag tgt ccc cgt aat tat gtg gta aca gat cac       912
Ala Thr Cys Val Lys Lys Cys Pro Arg Asn Tyr Val Val Thr Asp His
290                 295                 300 ggc tcg tgc gtc cga gcc tgt ggg gcc gac agc tat gag atg gag gaa       960
Gly Ser Cys Val Arg Ala Cys Gly Ala Asp Ser Tyr Glu Met Glu Glu
305                 310                 315                 320 gac ggc gtc cgc aag tgt aag aag tgc gaa ggg cct tgc cgc aaa gtg      1008
Asp Gly Val Arg Lys Cys Lys Lys Cys Glu Gly Pro Cys Arg Lys Val
                325                 330                 335 tgt aac gga ata ggt att ggt gaa ttt aaa gac tca ctc tcc ata aat      1056
Cys Asn Gly Ile Gly Ile Gly Glu Phe Lys Asp Ser Leu Ser Ile Asn
            340                 345                 350 gct acg aat att aaa cac ttc aaa aac tgc acc tcc atc agt ggc gat      1104
Ala Thr Asn Ile Lys His Phe Lys Asn Cys Thr Ser Ile Ser Gly Asp
        355                 360                 365 ctc cac atc ctg ccg gtg gca ttt agg ggt gac tcc ttc aca cat act      1152
Leu His Ile Leu Pro Val Ala Phe Arg Gly Asp Ser Phe Thr His Thr
    370                 375                 380 cct cct ctg gat cca cag gaa ctg gat att ctg aaa acc gta aag gaa      1200
Pro Pro Leu Asp Pro Gln Glu Leu Asp Ile Leu Lys Thr Val Lys Glu
385                 390                 395                 400 atc aca ggg ttt ttg ctg att cag gct tgg cct gaa aac agg acg gac      1248
Ile Thr Gly Phe Leu Leu Ile Gln Ala Trp Pro Glu Asn Arg Thr Asp
                405                 410                 415 ctc cat gcc ttt gag aac cta gaa atc ata cgc ggc agg acc aag caa      1296
Leu His Ala Phe Glu Asn Leu Glu Ile Ile Arg Gly Arg Thr Lys Gln
                420                 425                 430 cat ggt cag ttt tct ctt gca gtc gtc agc ctg aac ata aca tcc ttg      1344
His Gly Gln Phe Ser Leu Ala Val Val Ser Leu Asn Ile Thr Ser Leu
            435                 440                 445 gga tta cgc tcc ctc aag gag ata agt gat gga gat gtg ata att tca      1392
Gly Leu Arg Ser Leu Lys Glu Ile Ser Asp Gly Asp Val Ile Ile Ser
        450                 455                 460 gga aac aaa aat ttg tgc tat gca aat aca ata aac tgg aaa aaa ctg      1440
Gly Asn Lys Asn Leu Cys Tyr Ala Asn Thr Ile Asn Trp Lys Lys Leu
465                 470                 475                 480 ttt ggg acc tcc ggt cag aaa acc aaa att ata agc aac aga ggt gaa      1488
Phe Gly Thr Ser Gly Gln Lys Thr Lys Ile Ile Ser Asn Arg Gly Glu
                485                 490                 495 aac agc tgc aag gcc aca ggc cag gtc tgc cat gcc ttg tgc tcc ccc      1536
Asn Ser Cys Lys Ala Thr Gly Gln Val Cys His Ala Leu Cys Ser Pro
                500                 505                 510 gag ggc tgc tgg ggc ccg gag ccc agg gac tgc gtc tct tgc cgg aat      1584
Glu Gly Cys Trp Gly Pro Glu Pro Arg Asp Cys Val Ser Cys Arg Asn
            515                 520                 525 gtc agc cga ggc agg gaa tgc gtg gac aag tgc aac ctt ctg gag ggt      1632
Val Ser Arg Gly Arg Glu Cys Val Asp Lys Cys Asn Leu Leu Glu Gly
        530                 535                 540 gag cca agg gag ttt gtg gag aac tct gag tgc ata cag tgc cac cca      1680
Glu Pro Arg Glu Phe Val Glu Asn Ser Glu Cys Ile Gln Cys His Pro
545                 550                 555                 560 gag tgc ctg cct cag gcc atg aac atc acc tgc aca gga cgg gga cca      1728
Glu Cys Leu Pro Gln Ala Met Asn Ile Thr Cys Thr Gly Arg Gly Pro
                565                 570                 575 gac aac tgt atc cag tgt gcc cac tac att gac ggc ccc cac tgc gtc      1776
Asp Asn Cys Ile Gln Cys Ala His Tyr Ile Asp Gly Pro His Cys Val
                580                 585                 590 aag acc tgc ccg gca gga gtc atg gga gaa aac aac acc ctg gtc tgg      1824
Lys Thr Cys Pro Ala Gly Val Met Gly Glu Asn Asn Thr Leu Val Trp
            595                 600                 605
```

```
aag tac gca gac gcc ggc cat gtg tgc cac ctg tgc cat cca aac tgc      1872
Lys Tyr Ala Asp Ala Gly His Val Cys His Leu Cys His Pro Asn Cys
610             615                 620 acc tac gga tgc act ggg cca ggt ctt gaa ggc tgt cca acg aat ggg      1920
Thr Tyr Gly Cys Thr Gly Pro Gly Leu Glu Gly Cys Pro Thr Asn Gly
625             630                 635                 640 cct aag atc ccg tcc gat cca tct gac tta aac att ttc ctg gag atc      1968
Pro Lys Ile Pro Ser Asp Pro Ser Asp Leu Asn Ile Phe Leu Glu Ile
                645                 650                 655 ctt tgc tta gta ctc ttg tcc act acc tgt gta gtg acc tgg ctc tgc      2016
Leu Cys Leu Val Leu Leu Ser Thr Thr Cys Val Val Thr Trp Leu Cys
            660                 665                 670 tgc aaa cgc aga gga aag act tcc ttc tgg tca gat gtg cca gac cca      2064
Cys Lys Arg Arg Gly Lys Thr Ser Phe Trp Ser Asp Val Pro Asp Pro
        675                 680                 685 gcc cac agt agc ctg agc tcc tgg ttg ccc acc atc atg aca gag gaa      2112
Ala His Ser Ser Leu Ser Ser Trp Leu Pro Thr Ile Met Thr Glu Glu
    690                 695                 700 acc ttc cag tta ccc agc ttc tgg gac tcc agc gtg cca tca atc acc      2160
Thr Phe Gln Leu Pro Ser Phe Trp Asp Ser Ser Val Pro Ser Ile Thr
705             710                 715                 720 aag atc act gaa ctg gag gaa gac aag aaa ccg acc cac tgg gat tcc      2208
Lys Ile Thr Glu Leu Glu Glu Asp Lys Lys Pro Thr His Trp Asp Ser
                725                 730                 735 gaa agc tct ggg aat ggt agc ctt cca gcc ctg gtt cag gcc tat gtg      2256
Glu Ser Ser Gly Asn Gly Ser Leu Pro Ala Leu Val Gln Ala Tyr Val
            740                 745                 750 ctc caa gga gat cca aga gaa att tcc aac cag tcc cag cct ccc tct      2304
Leu Gln Gly Asp Pro Arg Glu Ile Ser Asn Gln Ser Gln Pro Pro Ser
        755                 760                 765 cgc act ggt gac cag gtc ctc tat ggt cag gtg ctt gag agc ccc acc      2352
Arg Thr Gly Asp Gln Val Leu Tyr Gly Gln Val Leu Glu Ser Pro Thr
    770                 775                 780 agc cca gga gta atg cag tac att cgc tct gac tcc act cag ccc ctg      2400
Ser Pro Gly Val Met Gln Tyr Ile Arg Ser Asp Ser Thr Gln Pro Leu
785             790                 795                 800 ttg ggg ggc ccc acc cct agc cct aaa tct tat gaa aac atc tgg ttc      2448
Leu Gly Gly Pro Thr Pro Ser Pro Lys Ser Tyr Glu Asn Ile Trp Phe
                805                 810                 815 cat tca aga ccc cag gag acc ttt gtg ccc caa cct cca aac cag gaa      2496
His Ser Arg Pro Gln Glu Thr Phe Val Pro Gln Pro Pro Asn Gln Glu
            820                 825                 830 gat gac tgt gtc ttt ggg cct cca ttt gat ttt ccc ctc ttt cag ggg      2544
Asp Asp Cys Val Phe Gly Pro Pro Phe Asp Phe Pro Leu Phe Gln Gly
        835                 840                 845 ctc cag gtc cat gga gtt gaa gaa caa ggg ggt ttc                      2580
Leu Gln Val His Gly Val Glu Glu Gln Gly Gly Phe
    850                 855                 860

<210> SEQ ID NO 2
<211> LENGTH: 860
<212> TYPE: PRT
<213> ORGANISM: Artificial
<220> FEATURE:
<223> OTHER INFORMATION: Synthetic Construct

<400> SEQUENCE: 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30
```

```
Gly Thr Ser Asn Lys Leu Thr Gln Leu Gly Thr Phe Glu Asp His Phe
             35                   40                  45

Leu Ser Leu Gln Arg Met Phe Asn Asn Cys Glu Val Val Leu Gly Asn
 50                   55                  60

Leu Glu Ile Thr Tyr Val Gln Arg Asn Tyr Asp Leu Ser Phe Leu Lys
 65               70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
             100                 105                 110

Tyr Glu Asn Ser Tyr Ala Leu Ala Val Leu Ser Asn Tyr Asp Ala Asn
             115                 120                 125

Lys Thr Gly Leu Lys Glu Leu Pro Met Arg Asn Leu Gln Glu Ile Leu
 130                 135                 140

His Gly Ala Val Arg Phe Ser Asn Asn Pro Ala Leu Cys Asn Val Glu
 145                 150                 155                 160

Ser Ile Gln Trp Arg Asp Ile Val Ser Ser Asp Phe Leu Ser Asn Met
             165                 170                 175

Ser Met Asp Phe Gln Asn His Leu Gly Ser Cys Gln Lys Cys Asp Pro
             180                 185                 190

Ser Cys Pro Asn Gly Ser Cys Trp Gly Ala Gly Glu Glu Asn Cys Gln
             195                 200                 205

Lys Leu Thr Lys Ile Ile Cys Ala Gln Gln Cys Ser Gly Arg Cys Arg
 210                 215                 220

Gly Lys Ser Pro Ser Asp Cys Cys His Asn Gln Cys Ala Ala Gly Cys
 225                 230                 235                 240

Thr Gly Pro Arg Glu Ser Asp Cys Leu Val Cys Arg Lys Phe Arg Asp
             245                 250                 255

Glu Ala Thr Cys Lys Asp Thr Cys Pro Pro Leu Met Leu Tyr Asn Pro
             260                 265                 270

Thr Thr Tyr Gln Met Asp Val Asn Pro Glu Gly Lys Tyr Ser Phe Gly
         275                 280                 285

Ala Thr Cys Val Lys Lys Cys Pro Arg Asn Tyr Val Val Thr Asp His
 290                 295                 300

Gly Ser Cys Val Arg Ala Cys Gly Ala Asp Ser Tyr Glu Met Glu Glu
 305                 310                 315                 320

Asp Gly Val Arg Lys Cys Lys Lys Cys Glu Gly Pro Cys Arg Lys Val
             325                 330                 335

Cys Asn Gly Ile Gly Ile Gly Glu Phe Lys Asp Ser Leu Ser Ile Asn
             340                 345                 350

Ala Thr Asn Ile Lys His Phe Lys Asn Cys Thr Ser Ile Ser Gly Asp
             355                 360                 365

Leu His Ile Leu Pro Val Ala Phe Arg Gly Asp Ser Phe Thr His Thr
             370                 375                 380

Pro Pro Leu Asp Pro Gln Glu Leu Asp Ile Leu Lys Thr Val Lys Glu
 385                 390                 395                 400

Ile Thr Gly Phe Leu Leu Ile Gln Ala Trp Pro Glu Asn Arg Thr Asp
             405                 410                 415

Leu His Ala Phe Glu Asn Leu Glu Ile Ile Arg Gly Arg Thr Lys Gln
             420                 425                 430

His Gly Gln Phe Ser Leu Ala Val Val Ser Leu Asn Ile Thr Ser Leu
             435                 440                 445
```

-continued

```
Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Asp Pro Ser Asp Leu Asn Ile Phe Leu Glu Ile
                645                 650                 655

Leu Cys Leu Val Leu Leu Ser Thr Thr Cys Val Val Thr Trp Leu Cys
            660                 665                 670

Cys Lys Arg Arg Gly Lys Thr Ser Phe Trp Ser Asp Val Pro Asp Pro
        675                 680                 685

Ala His Ser Ser Leu Ser Ser Trp Leu Pro Thr Ile Met Thr Glu Glu
    690                 695                 700

Thr Phe Gln Leu Pro Ser Phe Trp Asp Ser Ser Val Pro Ser Ile Thr
705                 710                 715                 720

Lys Ile Thr Glu Leu Glu Glu Asp Lys Lys Pro Thr His Trp Asp Ser
                725                 730                 735

Glu Ser Ser Gly Asn Gly Ser Leu Pro Ala Leu Val Gln Ala Tyr Val
            740                 745                 750

Leu Gln Gly Asp Pro Arg Glu Ile Ser Asn Gln Ser Gln Pro Pro Ser
        755                 760                 765

Arg Thr Gly Asp Gln Val Leu Tyr Gly Gln Val Leu Glu Ser Pro Thr
    770                 775                 780

Ser Pro Gly Val Met Gln Tyr Ile Arg Ser Asp Ser Thr Gln Pro Leu
785                 790                 795                 800

Leu Gly Gly Pro Thr Pro Ser Pro Lys Ser Tyr Glu Asn Ile Trp Phe
                805                 810                 815

His Ser Arg Pro Gln Glu Thr Phe Val Pro Gln Pro Asn Gln Glu
            820                 825                 830

Asp Asp Cys Val Phe Gly Pro Pro Phe Asp Phe Pro Leu Phe Gln Gly
        835                 840                 845

Leu Gln Val His Gly Val Glu Glu Gln Gly Gly Phe
    850                 855                 860
```

```
<210> SEQ ID NO 3
<211> LENGTH: 489
<212> TYPE: DNA
<213> ORGANISM: Homo sapiens
<220> FEATURE:
<221> NAME/KEY: CDS
<222> LOCATION: (1)..(489)

<400> SEQUENCE: 3 atg gag atg ctc tgt gcc ggc agg gtc cct gcg ctg ctg ctc tgc ctg      48
Met Glu Met Leu Cys Ala Gly Arg Val Pro Ala Leu Leu Leu Cys Leu
1               5                   10                  15 ggt ttc cat ctt cta cag gca gtc ctc agt aca act gtg att cca tca      96
Gly Phe His Leu Leu Gln Ala Val Leu Ser Thr Thr Val Ile Pro Ser
            20                  25                  30 tgt atc cca gga gag tcc agt gat aac tgc aca gct tta gtt cag aca     144
Cys Ile Pro Gly Glu Ser Ser Asp Asn Cys Thr Ala Leu Val Gln Thr
        35                  40                  45 gaa gac aat cca cgt gtg gct caa gtg tca ata aca aag tgt agc tct     192
Glu Asp Asn Pro Arg Val Ala Gln Val Ser Ile Thr Lys Cys Ser Ser
    50                  55                  60 gac atg aat ggc tat tgt ttg cat gga cag tgc atc tat ctg gtg gac     240
Asp Met Asn Gly Tyr Cys Leu His Gly Gln Cys Ile Tyr Leu Val Asp
65                  70                  75                  80 atg agt caa aac tac tgc agg tgt gaa gtg ggt tat act ggt gtc cga     288
Met Ser Gln Asn Tyr Cys Arg Cys Glu Val Gly Tyr Thr Gly Val Arg
                85                  90                  95 tgt gaa cac ttc ttt tta acc gtc cac caa cct tta agc aaa gag tat     336
Cys Glu His Phe Phe Leu Thr Val His Gln Pro Leu Ser Lys Glu Tyr
            100                 105                 110 gtg gct ttg acc gtg att ctt att att ttg ttt ctt atc aca gtc gtc     384
Val Ala Leu Thr Val Ile Leu Ile Ile Leu Phe Leu Ile Thr Val Val
        115                 120                 125 ggt tcc aca tat tat ttc tgc aga tgg tac aga aat cga aaa agt aaa     432
Gly Ser Thr Tyr Tyr Phe Cys Arg Trp Tyr Arg Asn Arg Lys Ser Lys
    130                 135                 140 gaa cca aag aag gaa tat gag aga gtt acc tca ggg gat cca gag ttg     480
Glu Pro Lys Lys Glu Tyr Glu Arg Val Thr Ser Gly Asp Pro Glu Leu
145                 150                 155                 160 ccg caa gtc                                                          489
Pro Gln Val <210> SEQ ID NO 4
<211> LENGTH: 163
<212> TYPE: PRT
<213> ORGANISM: Homo sapiens

<400> SEQUENCE: 4

Met Glu Met Leu Cys Ala Gly Arg Val Pro Ala Leu Leu Leu Cys Leu
1               5                   10                  15

Gly Phe His Leu Leu Gln Ala Val Leu Ser Thr Thr Val Ile Pro Ser
            20                  25                  30

Cys Ile Pro Gly Glu Ser Ser Asp Asn Cys Thr Ala Leu Val Gln Thr
        35                  40                  45

Glu Asp Asn Pro Arg Val Ala Gln Val Ser Ile Thr Lys Cys Ser Ser
    50                  55                  60

Asp Met Asn Gly Tyr Cys Leu His Gly Gln Cys Ile Tyr Leu Val Asp
65                  70                  75                  80

Met Ser Gln Asn Tyr Cys Arg Cys Glu Val Gly Tyr Thr Gly Val Arg
                85                  90                  95
```

```
Cys Glu His Phe Phe Leu Thr Val His Gln Pro Leu Ser Lys Glu Tyr
                100                 105                 110

Val Ala Leu Thr Val Ile Leu Ile Ile Leu Phe Leu Ile Thr Val Val
            115                 120                 125

Gly Ser Thr Tyr Tyr Phe Cys Arg Trp Tyr Arg Asn Arg Lys Ser Lys
        130                 135                 140

Glu Pro Lys Lys Glu Tyr Glu Arg Val Thr Ser Gly Asp Pro Glu Leu
145                 150                 155                 160

Pro Gln Val
```

<210> SEQ ID NO 5
<211> LENGTH: 357
<212> TYPE: DNA
<213> ORGANISM: Mus musculus
<220> FEATURE:
<221> NAME/KEY: CDS
<222> LOCATION: (1)..(357)

<400> SEQUENCE: 5

```
gag gtc cag ctg cag cag tct gga cct gag ctg gag aag cct ggc gct    48
Glu Val Gln Leu Gln Gln Ser Gly Pro Glu Leu Glu Lys Pro Gly Ala
1               5                   10                  15 tca gtg aag ata tcc tgc aag gct tct ggt tac tca ttc act ggc tac    96
Ser Val Lys Ile Ser Cys Lys Ala Ser Gly Tyr Ser Phe Thr Gly Tyr
            20                  25                  30 aac atg aac tgg gtg aag cag agc aat gga aag agc ctt gag tgg att   144
Asn Met Asn Trp Val Lys Gln Ser Asn Gly Lys Ser Leu Glu Trp Ile
        35                  40                  45 gga aat att gat cct tac tat ggt gct gct agc tac aac cag aag ttc   192
Gly Asn Ile Asp Pro Tyr Tyr Gly Ala Ala Ser Tyr Asn Gln Lys Phe
    50                  55                  60 aag ggc aag gcc aca ttg act gta gac aaa tcc tcc agc aca gcc tac   240
Lys Gly Lys Ala Thr Leu Thr Val Asp Lys Ser Ser Ser Thr Ala Tyr
65                  70                  75                  80 atg cag ctc aag agc ctg aca tct gag gac tct gca gtc tat tac tgt   288
Met Gln Leu Lys Ser Leu Thr Ser Glu Asp Ser Ala Val Tyr Tyr Cys
                85                  90                  95 gca aga tcc caa ctg cct tac tgg tac ttc gat gtc tgg ggc gca ggg   336
Ala Arg Ser Gln Leu Pro Tyr Trp Tyr Phe Asp Val Trp Gly Ala Gly
            100                 105                 110 acc acg gtc acc gtc tcc tca                                       357
Thr Thr Val Thr Val Ser Ser
        115
```

<210> SEQ ID NO 6
<211> LENGTH: 119
<212> TYPE: PRT
<213> ORGANISM: Mus musculus

<400> SEQUENCE: 6

```
Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Ala Ala Ser Tyr Asn Gln Lys Phe
    50                  55                  60

Lys Gly Lys Ala Thr Leu Thr Val Asp Lys Ser Ser Ser Thr Ala Tyr
65                  70                  75                  80
```

Met Gln Leu Lys Ser Leu Thr Ser Glu Asp Ser Ala Val Tyr Tyr Cys
                85                  90                  95

Ala Arg Ser Gln Leu Pro Tyr Trp Tyr Phe Asp Val Trp Gly Ala Gly
            100                 105                 110

Thr Thr Val Thr Val Ser Ser
        115

<210> SEQ ID NO 7
<211> LENGTH: 339
<212> TYPE: DNA
<213> ORGANISM: Mus musculus
<220> FEATURE:
<221> NAME/KEY: CDS
<222> LOCATION: (1)..(339)

<400> SEQUENCE: 7 gac att gtg atg aca cag tct cca tcc tcc ctg act gtg aca gca gga      48
Asp Ile Val Met Thr Gln Ser Pro Ser Ser Leu Thr Val Thr Ala Gly
1               5                   10                  15 gag aag gtc act atg agc tgc aag tcc agt cag agt ctg tta aac agt      96
Glu Lys Val Thr Met Ser Cys Lys Ser Ser Gln Ser Leu Leu Asn Ser
            20                  25                  30 gga aat caa aag aac tac ttg acc tgg tac cag cag aaa cca ggg cag     144
Gly Asn Gln Lys Asn Tyr Leu Thr Trp Tyr Gln Gln Lys Pro Gly Gln
        35                  40                  45 cct cct aaa ctg ttg atc tac tgg gca tcc act agg gaa tct ggg gtc     192
Pro Pro Lys Leu Leu Ile Tyr Trp Ala Ser Thr Arg Glu Ser Gly Val
    50                  55                  60 cct gat cgc ttc aca ggc agt gga tct gga aca gat ttc act ctc acc     240
Pro Asp Arg Phe Thr Gly Ser Gly Ser Gly Thr Asp Phe Thr Leu Thr
65                  70                  75                  80 atc agc agt gtg cag gct gaa gac ctg gca gtt tat tac tgt cag aat     288
Ile Ser Ser Val Gln Ala Glu Asp Leu Ala Val Tyr Tyr Cys Gln Asn
                85                  90                  95 gat tat agt tat ccg tac acg ttc gga ggg ggg acc aag ctg gaa ata     336
Asp Tyr Ser Tyr Pro Tyr Thr Phe Gly Gly Gly Thr Lys Leu Glu Ile
            100                 105                 110 aaa                                                                   339
Lys

<210> SEQ ID NO 8
<211> LENGTH: 113
<212> TYPE: PRT
<213> ORGANISM: Mus musculus

<400> SEQUENCE: 8

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Ile

<210> SEQ ID NO 9
<211> LENGTH: 15
<212> TYPE: DNA
<213> ORGANISM: Mus musculus
<220> FEATURE:
<221> NAME/KEY: CDS
<222> LOCATION: (1)..(15)

<400> SEQUENCE: 9

```
ggc tac aac atg aac                                          15
Gly Tyr Asn Met Asn
1               5
```

<210> SEQ ID NO 10
<211> LENGTH: 5
<212> TYPE: PRT
<213> ORGANISM: Mus musculus

<400> SEQUENCE: 10

```
Gly Tyr Asn Met Asn
1               5
```

<210> SEQ ID NO 11
<211> LENGTH: 51
<212> TYPE: DNA
<213> ORGANISM: Mus musculus
<220> FEATURE:
<221> NAME/KEY: CDS
<222> LOCATION: (1)..(51)

<400> SEQUENCE: 11

```
aat att gat cct tac tat ggt gct gct agc tac aac cag aag ttc aag    48
Asn Ile Asp Pro Tyr Tyr Gly Ala Ala Ser Tyr Asn Gln Lys Phe Lys
1               5                   10                  15 ggc                                                                51
Gly
```

<210> SEQ ID NO 12
<211> LENGTH: 17
<212> TYPE: PRT
<213> ORGANISM: Mus musculus

<400> SEQUENCE: 12

```
Asn Ile Asp Pro Tyr Tyr Gly Ala Ala Ser Tyr Asn Gln Lys Phe Lys
1               5                   10                  15

Gly
```

<210> SEQ ID NO 13
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 13

```
tcc caa ctg cct tac tgg tac ttc gat gtc                      30
Ser Gln Leu Pro Tyr Trp Tyr Phe Asp Val
1               5                   10
```

<210> SEQ ID NO 14
<211> LENGTH: 10

```
<212> TYPE: PRT
<213> ORGANISM: Mus musculus

<400> SEQUENCE: 14

Ser Gln Leu Pro Tyr Trp Tyr Phe Asp Val
1               5                   10

<210> SEQ ID NO 15
<211> LENGTH: 51
<212> TYPE: DNA
<213> ORGANISM: Mus musculus
<220> FEATURE:
<221> NAME/KEY: CDS
<222> LOCATION: (1)..(51)

<400> SEQUENCE: 15 aag tcc agt cag agt ctg tta aac agt gga aat caa aag aac tac ttg    48
Lys Ser Ser Gln Ser Leu Leu Asn Ser Gly Asn Gln Lys Asn Tyr Leu
1               5                   10                  15 acc                                                                 51
Thr

<210> SEQ ID NO 16
<211> LENGTH: 17
<212> TYPE: PRT
<213> ORGANISM: Mus musculus

<400> SEQUENCE: 16

Lys Ser Ser Gln Ser Leu Leu Asn Ser Gly Asn Gln Lys Asn Tyr Leu
1               5                   10                  15

Thr

<210> SEQ ID NO 17
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 17 tgg gca tcc act agg gaa tct                                         21
Trp Ala Ser Thr Arg Glu Ser
1               5

<210> SEQ ID NO 18
<211> LENGTH: 7
<212> TYPE: PRT
<213> ORGANISM: Mus musculus

<400> SEQUENCE: 18

Trp Ala Ser Thr Arg Glu Ser
1               5

<210> SEQ ID NO 19
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 19 cag aat gat tat agt tat ccg tac acg                                 27
Gln Asn Asp Tyr Ser Tyr Pro Tyr Thr
1               5
```

<210> SEQ ID NO 20
<211> LENGTH: 9
<212> TYPE: PRT
<213> ORGANISM: Mus musculus

<400> SEQUENCE: 20

Gln Asn Asp Tyr Ser Tyr Pro Tyr Thr
1               5

<210> SEQ ID NO 21
<211> LENGTH: 1449
<212> TYPE: DNA
<213> ORGANISM: Artificial
<220> FEATURE:
<223> OTHER INFORMATION: an artificially synthesized sequence
<220> FEATURE:
<221> NAME/KEY: CDS
<222> LOCATION: (1)..(1449)

<400> SEQUENCE: 21

```
atg gga tgg acc tgg atc ttt att tta atc ctg tca gta act aca ggt      48
Met Gly Trp Thr Trp Ile Phe Ile Leu Ile Leu Ser Val Thr Thr Gly
1               5                   10                  15 gtc cac tct gag gtc cag ctg cag cag tct gga cct gag ctg gag aag      96
Val His Ser Glu Val Gln Leu Gln Gln Ser Gly Pro Glu Leu Glu Lys
            20                  25                  30 cct ggc gct tca gtg aag ata tcc tgc aag gct tct ggt tac tca ttc     144
Pro Gly Ala Ser Val Lys Ile Ser Cys Lys Ala Ser Gly Tyr Ser Phe
        35                  40                  45 act ggc tac aac atg aac tgg gtg aag cag agc aat gga aag agc ctt     192
Thr Gly Tyr Asn Met Asn Trp Val Lys Gln Ser Asn Gly Lys Ser Leu
    50                  55                  60 gag tgg att gga aat att gat cct tac tat ggt gct gcc agc tac aac     240
Glu Trp Ile Gly Asn Ile Asp Pro Tyr Tyr Gly Ala Ala Ser Tyr Asn
65                  70                  75                  80 cag aag ttc aag ggc aag gcc aca ttg act gta gac aaa tcc tcc agc     288
Gln Lys Phe Lys Gly Lys Ala Thr Leu Thr Val Asp Lys Ser Ser Ser
                85                  90                  95 aca gcc tac atg cag ctc aag agc ctg aca tct gag gac tct gca gtc     336
Thr Ala Tyr Met Gln Leu Lys Ser Leu Thr Ser Glu Asp Ser Ala Val
            100                 105                 110 tat tac tgt gca aga tcc caa ctg cct tac tgg tac ttc gat gtc tgg     384
Tyr Tyr Cys Ala Arg Ser Gln Leu Pro Tyr Trp Tyr Phe Asp Val Trp
        115                 120                 125 ggc gca ggg acc acg gtc acc gtc tcc tca gct agc acc aag ggc cca     432
Gly Ala Gly Thr Thr Val Thr Val Ser Ser Ala Ser Thr Lys Gly Pro
    130                 135                 140 tcg gtc ttc ccc ctg gca ccc tcc tcc gct agc acc aag ggc cca tcg     480
Ser Val Phe Pro Leu Ala Pro Ser Ser Ala Ser Thr Lys Gly Pro Ser
145                 150                 155                 160 gtc ttc ccc ctg gca ccc tcc tcc aag agc acc tct ggg ggc aca gcg     528
Val Phe Pro Leu Ala Pro Ser Ser Lys Ser Thr Ser Gly Gly Thr Ala
                165                 170                 175 gcc ctg ggc tgc ctg gtc aag gac tac ttc ccc gaa ccg gtg acg gtg     576
Ala Leu Gly Cys Leu Val Lys Asp Tyr Phe Pro Glu Pro Val Thr Val
            180                 185                 190 tcg tgg aac tca ggc gcc ctg acc agc ggc gtg cac acc ttc ccg gct     624
Ser Trp Asn Ser Gly Ala Leu Thr Ser Gly Val His Thr Phe Pro Ala
        195                 200                 205 gtc cta cag tcc tca gga ctc tac tcc ctc agc agc gtg gtg acc gtg     672
Val Leu Gln Ser Ser Gly Leu Tyr Ser Leu Ser Ser Val Val Thr Val
```

```
ccc tcc agc agc ttg ggc acc cag acc tac atc tgc aac gtg aat cac      720
Pro Ser Ser Ser Leu Gly Thr Gln Thr Tyr Ile Cys Asn Val Asn His
225                 230                 235                 240 aag ccc agc aac acc aag gtg gac aag aaa gtt gag ccc aaa tct tgt      768
Lys Pro Ser Asn Thr Lys Val Asp Lys Lys Val Glu Pro Lys Ser Cys
                245                 250                 255 gac aaa act cac aca tgc cca ccg tgc cca gca cct gaa ctc ctg ggg      816
Asp Lys Thr His Thr Cys Pro Pro Cys Pro Ala Pro Glu Leu Leu Gly
            260                 265                 270 gga ccg tca gtc ttc ctc ttc ccc cca aaa ccc aag gac acc ctc atg      864
Gly Pro Ser Val Phe Leu Phe Pro Pro Lys Pro Lys Asp Thr Leu Met
        275                 280                 285 atc tcc cgg acc cct gag gtc aca tgc gtg gtg gtg gac gtg agc cac      912
Ile Ser Arg Thr Pro Glu Val Thr Cys Val Val Val Asp Val Ser His
    290                 295                 300 gaa gac cct gag gtc aag ttc aac tgg tac gtg gac ggc gtg gag gtg      960
Glu Asp Pro Glu Val Lys Phe Asn Trp Tyr Val Asp Gly Val Glu Val
305                 310                 315                 320 cat aat gcc aag aca aag ccg cgg gag gag cag tac aac agc acg tac     1008
His Asn Ala Lys Thr Lys Pro Arg Glu Glu Gln Tyr Asn Ser Thr Tyr
                325                 330                 335 cgt gtg gtc agc gtc ctc acc gtc ctg cac cag gac tgg ctg aat ggc     1056
Arg Val Val Ser Val Leu Thr Val Leu His Gln Asp Trp Leu Asn Gly
            340                 345                 350 aag gag tac aag tgc aag gtc tcc aac aaa gcc ctc cca gcc ccc atc     1104
Lys Glu Tyr Lys Cys Lys Val Ser Asn Lys Ala Leu Pro Ala Pro Ile
        355                 360                 365 gag aaa acc atc tcc aaa gcc aaa ggg cag ccc cga gaa cca cag gtg     1152
Glu Lys Thr Ile Ser Lys Ala Lys Gly Gln Pro Arg Glu Pro Gln Val
    370                 375                 380 tac acc ctg ccc cca tcc cgg gat gag ctg acc aag aac cag gtc agc     1200
Tyr Thr Leu Pro Pro Ser Arg Asp Glu Leu Thr Lys Asn Gln Val Ser
385                 390                 395                 400 ctg acc tgc ctg gtc aaa ggc ttc tat ccc agc gac atc gcc gtg gag     1248
Leu Thr Cys Leu Val Lys Gly Phe Tyr Pro Ser Asp Ile Ala Val Glu
                405                 410                 415 tgg gag agc aat ggg cag ccg gag aac aac tac aag acc acg cct ccc     1296
Trp Glu Ser Asn Gly Gln Pro Glu Asn Asn Tyr Lys Thr Thr Pro Pro
            420                 425                 430 gtg ctg gac tcc gac ggc tcc ttc ttc ctc tac agc aag ctc acc gtg     1344
Val Leu Asp Ser Asp Gly Ser Phe Phe Leu Tyr Ser Lys Leu Thr Val
        435                 440                 445 gac aag agc agg tgg cag cag ggg aac gtc ttc tca tgc tcc gtg atg     1392
Asp Lys Ser Arg Trp Gln Gln Gly Asn Val Phe Ser Cys Ser Val Met
    450                 455                 460 cat gag gct ctg cac aac cac tac acg cag aag agc ctc tcc ctg tct     1440
His Glu Ala Leu His Asn His Tyr Thr Gln Lys Ser Leu Ser Leu Ser
465                 470                 475                 480 ccg ggt aaa                                                          1449
Pro Gly Lys
```

<210> SEQ ID NO 22
<211> LENGTH: 483
<212> TYPE: PRT
<213> ORGANISM: Artificial
<220> FEATURE:
<223> OTHER INFORMATION: Synthetic Construct

<400> SEQUENCE: 22

```
Met Gly Trp Thr Trp Ile Phe Ile Leu Ile Leu Ser Val Thr Thr Gly
 1               5                  10                  15

Val His Ser Glu Val Gln Leu Gln Gln Ser Gly Pro Glu Leu Glu Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Ser Asn Gly Lys Ser Leu
    50                  55                  60

Glu Trp Ile Gly Asn Ile Asp Pro Tyr Tyr Gly Ala Ala Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Ala Arg Ser Gln Leu Pro Tyr Trp Tyr Phe Asp Val Trp
        115                 120                 125

Gly Ala Gly Thr Thr Val Thr Val Ser Ser Ala Ser Thr Lys Gly Pro
    130                 135                 140

Ser Val Phe Pro Leu Ala Pro Ser Ser Ala Ser Thr Lys Gly Pro Ser
145                 150                 155                 160

Val Phe Pro Leu Ala Pro Ser Ser Lys Ser Thr Ser Gly Gly Thr Ala
                165                 170                 175

Ala Leu Gly Cys Leu Val Lys Asp Tyr Phe Pro Glu Pro Val Thr Val
            180                 185                 190

Ser Trp Asn Ser Gly Ala Leu Thr Ser Gly Val His Thr Phe Pro Ala
        195                 200                 205

Val Leu Gln Ser Ser Gly Leu Tyr Ser Leu Ser Ser Val Val Thr Val
    210                 215                 220

Pro Ser Ser Ser Leu Gly Thr Gln Thr Tyr Ile Cys Asn Val Asn His
225                 230                 235                 240

Lys Pro Ser Asn Thr Lys Val Asp Lys Lys Val Glu Pro Lys Ser Cys
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
```

```
                    420             425             430
Val Leu Asp Ser Asp Gly Ser Phe Phe Leu Tyr Ser Lys Leu Thr Val
                435             440             445

Asp Lys Ser Arg Trp Gln Gln Gly Asn Val Phe Ser Cys Ser Val Met
            450             455             460

His Glu Ala Leu His Asn His Tyr Thr Gln Lys Ser Leu Ser Leu Ser
465             470             475             480

Pro Gly Lys

<210> SEQ ID NO 23
<211> LENGTH: 720
<212> TYPE: DNA
<213> ORGANISM: Artificial
<220> FEATURE:
<223> OTHER INFORMATION: an artificially synthesized sequence
<220> FEATURE:
<221> NAME/KEY: CDS
<222> LOCATION: (1)..(720)

<400> SEQUENCE: 23 atg gaa tca cag act cag gtc ctc atg tcc ctg ctg ttc tgg gta tct        48
Met Glu Ser Gln Thr Gln Val Leu Met Ser Leu Leu Phe Trp Val Ser
1               5                   10                  15 ggt acc tgt ggg gac att gtg atg aca cag tct cca tcc tcc ctg act        96
Gly Thr Cys Gly Asp Ile Val Met Thr Gln Ser Pro Ser Ser Leu Thr
                20                  25                  30 gtg aca gca gga gag aag gtc act atg agc tgc aag tcc agt cag agt       144
Val Thr Ala Gly Glu Lys Val Thr Met Ser Cys Lys Ser Ser Gln Ser
            35                  40                  45 ctg tta aac agt gga aat caa aag aac tac ttg acc tgg tac cag cag       192
Leu Leu Asn Ser Gly Asn Gln Lys Asn Tyr Leu Thr Trp Tyr Gln Gln
        50                  55                  60 aaa cca ggg cag cct cct aaa ctg ttg atc tac tgg gca tcc act agg       240
Lys Pro Gly Gln Pro Pro Lys Leu Leu Ile Tyr Trp Ala Ser Thr Arg
65                  70                  75                  80 gaa tct ggg gtc cct gat cgc ttc aca ggc agt gga tct gga aca gat       288
Glu Ser Gly Val Pro Asp Arg Phe Thr Gly Ser Gly Ser Gly Thr Asp
                85                  90                  95 ttc act ctc acc atc agc agt gtg cag gct gaa gac ctg gca gtt tat       336
Phe Thr Leu Thr Ile Ser Ser Val Gln Ala Glu Asp Leu Ala Val Tyr
                100                 105                 110 tac tgt cag aat gat tat agt tat ccg tac acg ttc gga ggg ggg acc       384
Tyr Cys Gln Asn Asp Tyr Ser Tyr Pro Tyr Thr Phe Gly Gly Gly Thr
            115                 120                 125 aag ctg gaa ata aaa cgt acg gtg gct gca cca tct gtc ttc atc ttc       432
Lys Leu Glu Ile Lys Arg Thr Val Ala Ala Pro Ser Val Phe Ile Phe
        130                 135                 140 ccg cca tct gat gag cag ttg aaa tct gga act gcc tct gtt gtg tgc       480
Pro Pro Ser Asp Glu Gln Leu Lys Ser Gly Thr Ala Ser Val Val Cys
145                 150                 155                 160 ctg ctg aat aac ttc tat ccc aga gag gcc aaa gta cag tgg aag gtg       528
Leu Leu Asn Asn Phe Tyr Pro Arg Glu Ala Lys Val Gln Trp Lys Val
                165                 170                 175 gat aac gcc ctc caa tcg ggt aac tcc cag gag agt gtc aca gag cag       576
Asp Asn Ala Leu Gln Ser Gly Asn Ser Gln Glu Ser Val Thr Glu Gln
                180                 185                 190 gac agc aag gac agc acc tac agc ctc agc agc acc ctg acg ctg agc       624
Asp Ser Lys Asp Ser Thr Tyr Ser Leu Ser Ser Thr Leu Thr Leu Ser
            195                 200                 205 aaa gca gac tac gag aaa cac aaa gtc tac gcc tgc gaa gtc acc cat       672
```

```
Lys Ala Asp Tyr Glu Lys His Lys Val Tyr Ala Cys Glu Val Thr His
            210                 215                 220 cag ggc ctg agc tcg ccc gtc aca aag agc ttc aac agg gga gag tgt      720
Gln Gly Leu Ser Ser Pro Val Thr Lys Ser Phe Asn Arg Gly Glu Cys
225                 230                 235                 240
```

<210> SEQ ID NO 24
<211> LENGTH: 240
<212> TYPE: PRT
<213> ORGANISM: Artificial
<220> FEATURE:
<223> OTHER INFORMATION: Synthetic Construct

<400> SEQUENCE: 24

```
Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Lys Ser Ser Gln Ser
        35                  40                  45

Leu Leu Asn Ser Gly Asn Gln Lys Asn Tyr Leu Thr Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro Tyr Thr Phe Gly Gly Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 25
<211> LENGTH: 4264
<212> TYPE: DNA
<213> ORGANISM: Homo sapiens
<220> FEATURE:
<221> NAME/KEY: CDS
<222> LOCATION: (207)..(689)

<400> SEQUENCE: 25

```
agccgccttc ctatttccgc cggcgggca gcgctgcggg gcgagtgcca gcagagaggc      60
gctcggtcct ccctccgccc tcccgcgccg ggggcaggcc ctgcctagtc tgcgtctttt     120
tcccccgcac cgcggcgccg ctccgccact cgggcaccgc aggtagggca ggaggctgga    180
```

```
gagcctgctg cccgcccgcc cgtaaa atg gtc ccc tcg gct gga cag ctc gcc        233
                             Met Val Pro Ser Ala Gly Gln Leu Ala
                              1               5 ctg ttc gct ctg ggt att gtg ttg gct gcg tgc cag gcc ttg gag aac        281
Leu Phe Ala Leu Gly Ile Val Leu Ala Ala Cys Gln Ala Leu Glu Asn
 10              15                  20                  25 agc acg tcc ccg ctg agt gca gac ccg ccc gtg gct gca gca gtg gtg        329
Ser Thr Ser Pro Leu Ser Ala Asp Pro Pro Val Ala Ala Ala Val Val
                 30                  35                  40 tcc cat ttt aat gac tgc cca gat tcc cac act cag ttc tgc ttc cat        377
Ser His Phe Asn Asp Cys Pro Asp Ser His Thr Gln Phe Cys Phe His
             45                  50                  55 gga acc tgc agg ttt ttg gtg cag gag gac aag cca gca tgt gtc tgc        425
Gly Thr Cys Arg Phe Leu Val Gln Glu Asp Lys Pro Ala Cys Val Cys
         60                  65                  70 cat tct ggg tac gtt ggt gca cgc tgt gag cat gcg gac ctc ctg gcc        473
His Ser Gly Tyr Val Gly Ala Arg Cys Glu His Ala Asp Leu Leu Ala
     75                  80                  85 gtg gtg gct gcc agc cag aag aag cag gcc atc acc gcc ttg gtg gtg        521
Val Val Ala Ala Ser Gln Lys Lys Gln Ala Ile Thr Ala Leu Val Val
 90                  95                 100                 105 gtc tcc atc gtg gcc ctg gct gtc ctt atc atc aca tgt gtg ctg ata        569
Val Ser Ile Val Ala Leu Ala Val Leu Ile Ile Thr Cys Val Leu Ile
                110                 115                 120 cac tgc tgc cag gtc cga aaa cac tgt gag tgg tgc cgg gcc ctc atc        617
His Cys Cys Gln Val Arg Lys His Cys Glu Trp Cys Arg Ala Leu Ile
             125                 130                 135 tgc cgg cac gag aag ccc agc gcc ctc ctg aag gga aga acc gct tgc        665
Cys Arg His Glu Lys Pro Ser Ala Leu Leu Lys Gly Arg Thr Ala Cys
         140                 145                 150 tgc cac tca gaa aca gtg gtc tga agagcccaga ggaggagttt ggccaggtgg       719
Cys His Ser Glu Thr Val Val
     155                 160 actgtggcag atcaataaag aaaggcttct tcaggacagc actgccagag atgcctgggt      779
gtgccacaga ccttcctact tggcctgtaa tcacctgtgc agcttttgt gggccttcaa       839 aactctgtca agaactccgt ctgcttgggg ttattcagtg tgacctagag aagaaatcag      899
cggaccacga tttcaagact tgttaaaaaa gaactgcaaa gagacggact cctgttcacc      959
taggtgaggt gtgtgcagca gttggtgtct gagtccacat gtgtgcagtt gtcttctgcc     1019
agccatggat tccaggctat atatttcttt ttaatgggcc acctccccac aacagaattc     1079
tgcccaacac aggagatttc tatagttatt gttttctgtc atttgcctac tggggaagaa     1139
agtgaaggag gggaaactgt ttaatatcac atgaagaccc tagctttaag agaagctgta     1199
tcctctaacc acgagaccct caaccagccc aacatcttcc atggacacat gacattgaag     1259
accatcccaa gctatcgcca cccttggaga tgatgtctta tttattagat ggataatggt     1319
tttattttta atctcttaag tcaatgtaaa aagtataaaa ccccttcaga cttctacatt     1379
aatgatgtat gtgttgctga ctgaaaagct atactgatta gaaatgtctg gcctcttcaa     1439
gacagctaag gcttgggaaa agtcttccag ggtgcggaga tggaaccaga ggctgggtta     1499
ctggtaggaa taaggtaggg ggttcagaaa tggtgccatt gaagccacaa agccggtaaa     1559
tgcctcaata cgttctggga gaaaacttag caaatccatc agcagggatc tgtcccctct     1619
gttggggaga gaggaagagt gtgtgtgtct acacaggata aacccaatac atattgtact     1679
gctcagtgat taaatgggtt cacttcctcg tgagccctcg gtaagtatgt ttagaaatag     1739
aacattagcc acgagccata ggcatttcag gccaaatcca tgaagggggg accagtcatt     1799
```

```
tattttccat tttgttgctt ggttggtttg ttgctttatt tttaaaagga gaagtttaac    1859
tttgctattt attttcgagc actaggaaaa ctattccagt aatttttttt tcctcatttc    1919
cattcaggat gccggcttta ttaacaaaaa ctctaacaag tcacctccac tatgtgggtc    1979
ttcctttccc ctcaagagaa ggagcaattg ttcccctgag catctgggtc catctgaccc    2039
atggggcctg cctgtgagaa acagtgggtc ccttcaaata catagtggat agctcatccc    2099
taggaatttt cattaaaatt tggaaacaga gtaatgaaga aataatatat aaactcctta    2159
tgtgaggaaa tgctactaat atctgaaaag tgaaagattt ctatgtatta actcttaagt    2219
gcacctagct tattacatcg tgaaaggtac atttaaaata tgttaaattg cttgaaatt     2279 ttcagagaat tttgtcttcc cctaattctt cttccttggt ctggaagaac aatttctatg    2339 aatttctct ttattttttt ttataattca gacaattcta tgacccgtgt cttcattttt     2399
ggcactctta tttaacaatg ccacacctga agcacttgga tctgttcaga gctgacccc     2459 tagcaacgta gttgacacag ctccaggttt taaattact aaaataagtt caagtttaca     2519
tcccttgggc cagatatgtg ggttgaggct tgactgtagc atcctgctta gagaccaatc    2579
aacggacact ggttttttaga cctctatcaa tcagtagtta gcatccaaga gactttgcag   2639
aggcgtagga atgaggctgg acagatggcg gaagcagagg ttccctgcga agacttgaga    2699
tttagtgtct gtgaatgttc tagttcctag gtccagcaag tcacacctgc cagtgccctc    2759
atccttatgc ctgtaacaca catgcagtga gaggcctcac atatacgcct ccctagaagt    2819
gccttccaag tcagtccttt ggaaaccagc aggtctgaaa aagaggctgc atcaatgcaa    2879
gcctggttgg accattgtcc atgcctcagg atagaacagc ctggcttatt tggggatttt    2939
tcttctagaa atcaaatgac tgataagcat tggatccctc tgccatttaa tggcaatggt    2999
agtctttggt tagctgcaaa aatactccat ttcaagttaa aaatgcatct tctaatccat    3059
ctctgcaagc tccctgtgtt tccttgccct ttagaaaatg aattgttcac tacaattaga    3119
gaatcattta acatcctgac ctggtaagct gccacacacc tggcagtggg gagcatcgct    3179
gtttccaatg gctcaggaga caatgaaaag ccccccattta aaaaataac aaacattttt    3239 taaaaggcct ccaatactct tatggagcct ggattttttcc cactgctcta caggctgtga    3299
ctttttttaa gcatcctgac aggaaatgtt ttcttctaca tggaaagata gacagcagcc    3359
aaccctgatc tggaagacag ggccccggct ggacacacgt ggaaccaagc cagggatggg    3419
ctggccattg tgtccccgca ggagagatgg gcagaatggc cctagagttc ttttcctga    3479 gaaaggagaa aaagatggga ttgccactca cccacccaca ctggtaaggg aggagaattt    3539
gtgcttctgg agcttctcaa gggattgtgt tttgcaggta cagaaaactg cctgttatct    3599
tcaagccagg ttttcgaggg cacatgggtc accagttgct ttttcagtca atttggccgg    3659
gatggactaa tgaggctcta acactgctca ggagacccct gccctctagt tggttctggg    3719
ctttgatctc ttccaacctg cccagtcaca gaaggaggaa tgactcaaat gcccaaaacc    3779
aagaacacat tgcagaagta agacaaacat gtatatttt aaatgttcta acataagacc     3839
tgttctctct agccattgat ttaccaggct ttctgaaaga tctagtggtt cacacagaga    3899
gagagagagt actgaaaaag caactcctct tcttagtctt aataatttac taaaatggtc    3959 aactttcat tatctttatt ataataaacc tgatgctttt tttagaact ccttactctg      4019 atgtctgtat atgttgcact gaaaggtta atattaatg ttttaattta ttttgtgtgg      4079
taagttaatt ttgattctg taatgtgtta atgtgattag cagttatttt ccttaatatc     4139
```

```
tgaattatac ttaaagagta gtgagcaata taagacgcaa ttgtgttttt cagtaatgtg    4199
cattgttatt gagttgtact gtaccttatt tggaaggatg aaggaatgaa tcttttttc     4259 ctaaa                                                                4264
```

<210> SEQ ID NO 26
<211> LENGTH: 160
<212> TYPE: PRT
<213> ORGANISM: Homo sapiens

<400> SEQUENCE: 26

```
Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
            20                  25                  30

Asp Pro Val Ala Ala Ala Val Val Ser His Phe Asn Asp Cys Pro
        35                  40                  45

Asp Ser His Thr Gln Phe Cys Phe His Gly Thr Cys Arg Phe Leu Val
    50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Ala Ala Ser Gln Lys
                85                  90                  95

Lys Gln Ala Ile Thr Ala Leu Val Val Val Ser Ile Val Ala Leu Ala
            100                 105                 110

Val Leu Ile Ile Thr Cys Val Leu Ile His Cys Cys Gln Val Arg Lys
        115                 120                 125

His Cys Glu Trp Cys Arg Ala Leu Ile Cys Arg His Glu Lys Pro Ser
    130                 135                 140

Ala Leu Leu Lys Gly Arg Thr Ala Cys Cys His Ser Glu Thr Val Val
145                 150                 155                 160
```

<210> SEQ ID NO 27
<211> LENGTH: 4
<212> TYPE: PRT
<213> ORGANISM: Artificial
<220> FEATURE:
<223> OTHER INFORMATION: an artificially synthesized sequence

<400> SEQUENCE: 27

```
Gly Gly Gly Ser
1
```

<210> SEQ ID NO 28
<211> LENGTH: 4
<212> TYPE: PRT
<213> ORGANISM: Artificial
<220> FEATURE:
<223> OTHER INFORMATION: an artificially synthesized sequence

<400> SEQUENCE: 28

```
Ser Gly Gly Gly
1
```

<210> SEQ ID NO 29
<211> LENGTH: 5
<212> TYPE: PRT
<213> ORGANISM: Artificial
<220> FEATURE:
<223> OTHER INFORMATION: an artificially synthesized sequence

<400> SEQUENCE: 29

```
Gly Gly Gly Gly Ser
1               5

<210> SEQ ID NO 30
<211> LENGTH: 5
<212> TYPE: PRT
<213> ORGANISM: Artificial
<220> FEATURE:
<223> OTHER INFORMATION: an artificially synthesized sequence

<400> SEQUENCE: 30

Ser Gly Gly Gly Gly
1               5

<210> SEQ ID NO 31
<211> LENGTH: 6
<212> TYPE: PRT
<213> ORGANISM: Artificial
<220> FEATURE:
<223> OTHER INFORMATION: an artificially synthesized sequence

<400> SEQUENCE: 31

Gly Gly Gly Gly Gly Ser
1               5

<210> SEQ ID NO 32
<211> LENGTH: 6
<212> TYPE: PRT
<213> ORGANISM: Artificial
<220> FEATURE:
<223> OTHER INFORMATION: an artificially synthesized sequence

<400> SEQUENCE: 32

Ser Gly Gly Gly Gly Gly
1               5

<210> SEQ ID NO 33
<211> LENGTH: 7
<212> TYPE: PRT
<213> ORGANISM: Artificial
<220> FEATURE:
<223> OTHER INFORMATION: an artificially synthesized sequence

<400> SEQUENCE: 33

Gly Gly Gly Gly Gly Gly Ser
1               5

<210> SEQ ID NO 34
<211> LENGTH: 7
<212> TYPE: PRT
<213> ORGANISM: Artificial
<220> FEATURE:
<223> OTHER INFORMATION: an artificially synthesized sequence

<400> SEQUENCE: 34

Ser Gly Gly Gly Gly Gly Gly
1               5

<210> SEQ ID NO 35
<211> LENGTH: 47
<212> TYPE: PRT
<213> ORGANISM: Homo sapiens

<400> SEQUENCE: 35

Gln Val Ser Ile Thr Lys Cys Ser Ser Asp Met Asn Gly Tyr Cys Leu
1               5                   10                  15
```

His Gly Gln Cys Ile Tyr Leu Val Asp Met Ser Gln Asn Tyr Cys Arg
                20                  25                  30

Cys Glu Val Gly Tyr Thr Gly Val Arg Cys Glu His Phe Phe Leu
            35                  40                  45

<210> SEQ ID NO 36
<211> LENGTH: 47
<212> TYPE: PRT
<213> ORGANISM: Homo sapiens

<400> SEQUENCE: 36

Val Ser His Phe Asn Asp Cys Pro Asp Ser His Thr Gln Phe Cys Phe
1               5                   10                  15

His Gly Thr Cys Arg Phe Leu Val Gln Glu Asp Lys Pro Ala Cys Val
                20                  25                  30

Cys His Ser Gly Tyr Val Gly Ala Arg Cys Glu His Ala Asp Leu
            35                  40                  45

<210> SEQ ID NO 37
<211> LENGTH: 317
<212> TYPE: PRT
<213> ORGANISM: Artificial
<220> FEATURE:
<223> OTHER INFORMATION: an artificially synthesized sequence

<400> SEQUENCE: 37

Met Val Leu Ala Ser Ser Thr Thr Ser Ile His Thr Met Leu Leu Leu
1               5                   10                  15

Leu Leu Met Leu Ala Gln Pro Ala Met Ala Val Ser His Phe Asn Asp
                20                  25                  30

Cys Pro Asp Ser His Thr Gln Phe Cys Phe His Gly Thr Cys Arg Phe
                35                  40                  45

Leu Val Gln Glu Asp Lys Pro Ala Cys Val Cys His Ser Gly Tyr Val
            50                  55                  60

Gly Ala Arg Cys Glu His Ala Asp Leu Leu Ala Val Val Ala Ala Ser
65              70                  75                  80

Gln Lys Lys Gln Glu Pro Arg Gly Pro Thr Ile Lys Pro Cys Pro Pro
                85                  90                  95

Cys Lys Cys Pro Ala Pro Asn Leu Leu Gly Gly Pro Ser Val Phe Ile
            100                 105                 110

Phe Pro Pro Lys Ile Lys Asp Val Leu Met Ile Ser Leu Ser Pro Ile
            115                 120                 125

Val Thr Cys Val Val Val Asp Val Ser Glu Asp Asp Pro Asp Val Gln
            130                 135                 140

Ile Ser Trp Phe Val Asn Asn Val Glu Val His Thr Ala Gln Thr Gln
145                 150                 155                 160

Thr His Arg Glu Asp Tyr Asn Ser Thr Leu Arg Val Val Ser Ala Leu
                165                 170                 175

Pro Ile Gln His Gln Asp Trp Met Ser Gly Lys Glu Phe Lys Cys Lys
            180                 185                 190

Val Asn Asn Lys Asp Leu Pro Ala Pro Ile Glu Arg Thr Ile Ser Lys
            195                 200                 205

Pro Lys Gly Ser Val Arg Ala Pro Gln Val Tyr Val Leu Pro Pro Pro
        210                 215                 220

Glu Glu Glu Met Thr Lys Lys Gln Val Thr Leu Thr Cys Met Val Thr
225                 230                 235                 240

```
Asp Phe Met Pro Glu Asp Ile Tyr Val Glu Trp Thr Asn Asn Gly Lys
                245                 250                 255

Thr Glu Leu Asn Tyr Lys Asn Thr Glu Pro Val Leu Asp Ser Asp Gly
            260                 265                 270

Ser Tyr Phe Met Tyr Ser Lys Leu Arg Val Glu Lys Lys Asn Trp Val
        275                 280                 285

Glu Arg Asn Ser Tyr Ser Cys Ser Val Val His Glu Gly Leu His Asn
    290                 295                 300

His His Thr Thr Lys Ser Phe Ser Arg Thr Pro Gly Lys
305                 310                 315

<210> SEQ ID NO 38
<211> LENGTH: 954
<212> TYPE: DNA
<213> ORGANISM: Artificial
<220> FEATURE:
<223> OTHER INFORMATION: an artificially synthesized sequence

<400> SEQUENCE: 38
atggttcttg ccagctctac caccagcatc cacaccatgc tgctcctgct cctgatgctg    60
gcccagccgg ccatggcggt gtcccatttt aatgactgcc agattccca cactcagttc   120 tgcttccatg gaacctgcag gtttttggtg caggaggaca agccagcatg tgtctgccat   180
tctgggtacg ttggtgcacg ctgtgagcat gcggacctcc tggccgtggt ggctgccagc   240
cagaagaagc aggaacctcg cggaccgaca atcaagccct gtcctccatg caaatgccca   300
gcacctaacc tcttgggtgg accatccgtc ttcatcttcc ctccaaagat caaggatgta   360
ctcatgatct ccctgagccc catagtcaca tgtgtggtgg tggatgtgag cgaggatgac   420
ccagatgtcc agatcagctg gtttgtgaac aacgtggaag tacacacagc tcagacacaa   480
acccatagag aggattacaa cagtactctc cgggtggtca gtgccctccc catccagcac   540
caggactgga tgagtggcaa ggagttcaaa tgcaaggtca acaacaaaga cctcccagcg   600
cccatcgaga gaaccatctc aaaacccaaa gggtcagtaa gagctccaca ggtatatgtc   660
ttgcctccac cagaagaaga gatgactaag aaacaggtca ctctgacctg catggtcaca   720
gacttcatgc ctgaagacat ttacgtggag tggaccaaca cgggaaaaac agagctaaac   780
tacaagaaca ctgaaccagt cctggactct gatggttctt acttcatgta cagcaagctg   840
agagtggaaa agaagaactg ggtggaaaga aatagctact cctgttcagt ggtccacgag   900
ggtctgcaca tcaccacac gactaagagc ttctcccgga ctccgggtaa atga         954

<210> SEQ ID NO 39
<211> LENGTH: 219
<212> TYPE: PRT
<213> ORGANISM: Artificial
<220> FEATURE:
<223> OTHER INFORMATION: an artificially synthesized sequence

<400> SEQUENCE: 39

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60
```

```
Pro Gly Thr Ala Pro Lys Tyr Gly Ile Arg Gly Ile Pro Thr Leu Leu
 65                 70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Asp Ile Gly Ile Asn Ser Asp Pro Asn Ser Val Ser His Phe Asn Asp
                165                 170                 175

Cys Pro Asp Ser His Thr Gln Phe Cys Phe His Gly Thr Cys Arg Phe
                180                 185                 190

Leu Val Gln Glu Asp Lys Pro Ala Cys Val Cys His Ser Gly Tyr Val
            195                 200                 205

Gly Ala Arg Cys Glu His Ala Asp Leu Leu Ala
        210                 215
```

<210> SEQ ID NO 40
<211> LENGTH: 660
<212> TYPE: DNA
<213> ORGANISM: Artificial
<220> FEATURE:
<223> OTHER INFORMATION: an artificially synthesized sequence

<400> SEQUENCE: 40

```
atgagcgata aaattattca cctgactgac gacagttttg acacggatgt actcaaagcg     60
gacgggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg gccatatgca ccatcatcat    360
catcattctt ctggtctggt gccacgcggt tctggtatga agaaaccgc tgctgctaaa    420
ttcgaacgcc agcacatgga cagcccagat ctgggtaccg acgacgacga caaggccatg    480
gatatcggaa ttaattcgga tccgaattcg gtgtcccatt ttaatgactg cccagattcc    540
cacactcagt tctgcttcca tggaacctgc aggttttgg tgcaggagga caagccagca    600
tgtgtctgcc attctgggta cgttggtgca cgctgtgagc atgcggacct cctggcctga    660
```

<210> SEQ ID NO 41
<211> LENGTH: 907
<212> TYPE: PRT
<213> ORGANISM: Artificial
<220> FEATURE:
<223> OTHER INFORMATION: an artificially synthesized sequence

<400> SEQUENCE: 41

```
Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
```

```
                35                  40                  45
Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
                115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Asn Cys Gln
                195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
                275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
                355                 360                 365

Leu His Ile Leu Pro Val Ala Phe Arg Gly Asp Ser Phe Thr His Thr
                370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
                435                 440                 445

Gly Leu Arg Ser Leu Lys Glu Ile Ser Asp Gly Asp Val Ile Ile Ser
450                 455                 460
```

```
Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser Cys Arg Asn
    515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Val Thr Val Pro Ser Ser Leu Gly Thr Gln
                645                 650                 655

Thr Tyr Ile Cys Asn Val Asn His Lys Pro Ser Asn Thr Lys Val Asp
            660                 665                 670

Lys Lys Val Glu Pro Lys Ser Cys Asp Lys Thr His Thr Cys Pro Pro
        675                 680                 685

Cys Pro Ala Pro Glu Leu Leu Gly Gly Pro Ser Val Phe Leu Phe Pro
    690                 695                 700

Pro Lys Pro Lys Asp Thr Leu Met Ile Ser Arg Thr Pro Glu Val Thr
705                 710                 715                 720

Cys Val Val Val Asp Val Ser His Glu Asp Pro Glu Val Lys Phe Asn
                725                 730                 735

Trp Tyr Val Asp Gly Val Glu Val His Asn Ala Lys Thr Lys Pro Arg
            740                 745                 750

Glu Glu Gln Tyr Asn Ser Thr Tyr Arg Val Val Ser Val Leu Thr Val
        755                 760                 765

Leu His Gln Asp Trp Leu Asn Gly Lys Glu Tyr Lys Cys Lys Val Ser
    770                 775                 780

Asn Lys Ala Leu Pro Ala Pro Ile Glu Lys Thr Ile Ser Lys Ala Lys
785                 790                 795                 800

Gly Gln Pro Arg Glu Pro Gln Val Tyr Thr Leu Pro Pro Ser Arg Asp
                805                 810                 815

Glu Leu Thr Lys Asn Gln Val Ser Leu Thr Cys Leu Val Lys Gly Phe
            820                 825                 830

Tyr Pro Ser Asp Ile Ala Val Glu Trp Glu Ser Asn Gly Gln Pro Glu
        835                 840                 845

Asn Asn Tyr Lys Thr Thr Pro Pro Val Leu Asp Ser Asp Gly Ser Phe
850                 855                 860

Phe Leu Tyr Ser Lys Leu Thr Val Asp Lys Ser Arg Trp Gln Gln Gly
865                 870                 875                 880
```

Asn Val Phe Ser Cys Ser Val Met His Glu Ala Leu His Asn His Tyr
            885                 890                 895

Thr Gln Lys Ser Leu Ser Leu Ser Pro Gly Lys
        900                 905

<210> SEQ ID NO 42
<211> LENGTH: 2724
<212> TYPE: DNA
<213> ORGANISM: Artificial
<220> FEATURE:
<223> OTHER INFORMATION: an artificially synthesized sequence

<400> SEQUENCE: 42

| | | | | | |
|---|---|---|---|---|---|
| atgcgaccct | ccgggacggc | cggggcagcg | ctcctggcgc | tgctggctgc | gctctgcccg | 60 |
| gcgagtcggg | ctctggagga | aaagaaagtt | tgccaaggca | cgagtaacaa | gctcacgcag | 120 |
| ttgggcactt | ttgaagatca | tttctcagc | ctccagagga | tgttcaataa | ctgtgaggtg | 180 |
| gtccttggga | atttgaaat | tacctatgtg | cagaggaatt | atgatctttc | cttcttaaag | 240 |
| accatccagg | aggtggctgg | ttatgtcctc | attgccctca | acacagtgga | gcgaattcct | 300 |
| ttggaaaacc | tgcagatcat | cagaggaaat | atgtactacg | aaaattccta | tgccttagca | 360 |
| gtcttatcta | actatgatgc | aaataaaacc | ggactgaagg | agctgcccat | gagaaattta | 420 |
| caggaaatcc | tgcatggcgc | cgtgcggttc | agcaacaacc | ctgccctgtg | caacgtggag | 480 |
| agcatccagt | ggcgggacat | agtcagcagt | gactttctca | gcaacatgtc | gatggacttc | 540 |
| cagaaccacc | tgggcagctg | ccaaaagtgt | gatccaagct | gtcccaatgg | gagctgctgg | 600 |
| ggtgcaggag | aggagaactg | ccagaaactg | accaaaatca | tctgtgccca | gcagtgctcc | 660 |
| gggcgctgcc | gtggcaagtc | ccccagtgac | tgctgccaca | accagtgtgc | tgcaggctgc | 720 |
| acaggccccc | gggagagcga | ctgcctggtc | tgccgcaaat | tccgagacga | agccacgtgc | 780 |
| aaggacacct | gcccccact | catgctctac | aaccccacca | cgtaccagat | ggatgtgaac | 840 |
| cccgagggca | aatacagctt | tggtgccacc | tgcgtgaaga | agtgtccccg | taattatgtg | 900 |
| gtgacagatc | acggctcgtg | cgtccgagcc | tgtggggccg | acagctatga | gatggaggaa | 960 |
| gacggcgtcc | gcaagtgtaa | gaagtgcgaa | gggccttgcc | gcaaagtgtg | taacggaata | 1020 |
| ggtattggtg | aatttaaaga | ctcactctcc | ataaatgcta | cgaatattaa | acacttcaaa | 1080 |
| aactgcacct | ccatcagtgg | cgatctccac | atcctgccgg | tggcatttag | ggtgactcc | 1140 |
| ttcacacata | ctcctcctct | ggatccacag | gaactggata | ttctgaaaac | cgtaaaggaa | 1200 |
| atcacagggt | ttttgctgat | tcaggcttgg | cctgaaaaca | ggacggacct | ccatgccttt | 1260 |
| gagaacctag | aaatcatacg | cggcaggacc | aagcaacatg | gtcagttttc | tcttgcagtc | 1320 |
| gtcagcctga | acataacatc | cttgggatta | cgctccctca | aggagataag | tgatggagat | 1380 |
| gtgataattt | caggaaacaa | aaatttgtgc | tatgcaaata | caataaactg | gaaaaaactg | 1440 |
| tttgggacct | ccggtcagaa | aaccaaaatt | ataagcaaca | gaggtgaaaa | cagctgcaag | 1500 |
| gccacaggcc | aggtctgcca | tgccttgtgc | tcccccgagg | gctgctgggg | cccggagccc | 1560 |
| agggactgcg | tctcttgccg | gaatgtcagc | cgaggcaggg | aatgcgtgga | caagtgcaac | 1620 |
| cttctggagg | gtgagccaag | ggagtttgtg | gagaactctg | agtgcataca | gtgccaccca | 1680 |
| gagtgcctgc | ctcaggccat | gaacatcacc | tgcacaggac | ggggaccaga | caactgtatc | 1740 |
| cagtgtgccc | actacattga | cggcccccac | tgcgtcaaga | cctgcccggc | aggagtcatg | 1800 |
| ggagaaaaca | cacccctggt | ctggaagtac | gcagacgccg | gcatgtgtgc | cacctgtgc | 1860 |
| catccaaact | gcacctacgg | atgcactggg | ccaggtcttg | aaggctgtcc | aacgaatggg | 1920 |

```
cctaagatcc cgtcggtcac cgtgccctcc agcagcttgg gcacccagac ctacatctgc   1980
aacgtgaatc acaagcccag caacaccaag gtggacaaga agttgagcc caaatcttgt    2040 gacaaaactc acacatgccc accgtgccca gcacctgaac tcctgggggg accgtcagtc   2100
ttcctcttcc ccccaaaacc caaggacacc ctcatgatct cccggacccc tgaggtcaca   2160
tgcgtggtgg tggacgtgag ccacgaagac cctgaggtca agttcaactg gtacgtggac   2220
ggcgtggagg tgcataatgc caagacaaag ccgcgggagg agcagtacaa cagcacgtac   2280
cgtgtggtca gcgtcctcac cgtcctgcac caggactggc tgaatggcaa ggagtacaag   2340
tgcaaggtct ccaacaaagc cctcccagcc cccatcgaga aaaccatctc caaagccaaa   2400
gggcagcccc gagaaccaca ggtgtacacc ctgcccccat cccgggatga gctgaccaag   2460
aaccaggtca gcctgacctg cctggtcaaa ggcttctatc ccagcgacat cgccgtggag   2520
tgggagagca atgggcagcc ggagaacaac tacaagacca cgcctcccgt gctggactcc   2580
gacggctcct tcttcctcta cagcaagctc accgtggaca agagcaggtg gcagcagggg   2640
aacgtcttct catgctccgt gatgcatgag gctctgcaca accactacac gcagaagagc   2700
ctctccctgt ctccgggtaa atga                                         2724
```

<210> SEQ ID NO 43
<211> LENGTH: 351
<212> TYPE: DNA
<213> ORGANISM: Mus musculus

<400> SEQUENCE: 43

```
gatgtgcagc ttcaggagtc gggacctggc ctggtgaaac cttctcagtc tctgtccctc    60
acctgcactg tcactggcta ctcaatcacc agtgattatg cctggaactg gatccggctg   120
tttccaggaa acaaactgga gtggatgggc ttcataaact acagtggtaa cactagctac   180
aacccatctc tcaaaagtcg aatctctatc actcgagaca catccaagaa ccagttcttc   240
ctgaagttga attctttgac tactgacgac acagccacat attactgtgc aagagggggc   300
ctatcgcggt tccttactgg gggccaaggg actctggtca ccgtctctgc a            351
```

<210> SEQ ID NO 44
<211> LENGTH: 117
<212> TYPE: PRT
<213> ORGANISM: Mus musculus

<400> SEQUENCE: 44

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Leu Phe Pro Gly Asn Lys Leu Glu Trp
        35                  40                  45

Met Gly Phe Ile Asn Tyr Ser Gly Asn Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Lys Leu Asn Ser Leu Thr Thr Asp Asp Thr Ala Thr Tyr Tyr Cys
                85                  90                  95

Ala Arg Gly Gly Leu Ser Arg Phe Pro Tyr Trp Gly Gln Gly Thr Leu
            100                 105                 110

Val Thr Val Ser Ala

-continued

```
<210> SEQ ID NO 45
<211> LENGTH: 321
<212> TYPE: DNA
<213> ORGANISM: Mus musculus

<400> SEQUENCE: 45
gatatccaga tgacacagac tacatcctcc ctgtctgcct ctctgggaga cagagtcacc      60
atcagttgca ggtcaagtca ggacattaga aattatttaa actggtatca gcagaaacca     120
gatggaactg ttaaactcct gatctactat acatccagat cacactcagg agtcccctca     180
aggttcagtg gcagtgggtc tggaacagat tattctctca ccattagcaa cctggagcag     240
gaagatattg ccacttactt ttgccaacag ggtaatatgt ttccgttcac gttcggaggg     300
gggaccaagc tggaaataaa a                                               321

<210> SEQ ID NO 46
<211> LENGTH: 107
<212> TYPE: PRT
<213> ORGANISM: Mus musculus

<400> SEQUENCE: 46

Asp Ile Gln Met Thr Gln Thr Thr Ser Ser Leu Ser Ala Ser Leu Gly
1               5                   10                  15

Asp Arg Val Thr Ile Ser Cys Arg Ser Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Ser His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Met Phe Pro Phe
                85                  90                  95

Thr Phe Gly Gly Gly Thr Lys Leu Glu Ile Lys
            100                 105

<210> SEQ ID NO 47
<211> LENGTH: 6
<212> TYPE: PRT
<213> ORGANISM: Mus musculus

<400> SEQUENCE: 47

Ser Asp Tyr Ala Trp Asn
1               5

<210> SEQ ID NO 48
<211> LENGTH: 16
<212> TYPE: PRT
<213> ORGANISM: Mus musculus

<400> SEQUENCE: 48

Phe Ile Asn Tyr Ser Gly Asn Thr Ser Tyr Asn Pro Ser Leu Lys Ser
1               5                   10                  15

<210> SEQ ID NO 49
<211> LENGTH: 8
<212> TYPE: PRT
<213> ORGANISM: Mus musculus
```

<400> SEQUENCE: 49

Gly Gly Leu Ser Arg Phe Pro Tyr
1               5

<210> SEQ ID NO 50
<211> LENGTH: 11
<212> TYPE: PRT
<213> ORGANISM: Mus musculus

<400> SEQUENCE: 50

Arg Ser Ser Gln Asp Ile Arg Asn Tyr Leu Asn
1               5                   10

<210> SEQ ID NO 51
<211> LENGTH: 7
<212> TYPE: PRT
<213> ORGANISM: Mus musculus

<400> SEQUENCE: 51

Tyr Thr Ser Arg Ser His Ser
1               5

<210> SEQ ID NO 52
<211> LENGTH: 9
<212> TYPE: PRT
<213> ORGANISM: Mus musculus

<400> SEQUENCE: 52

Gln Gln Gly Asn Met Phe Pro Phe Thr
1               5

<210> SEQ ID NO 53
<211> LENGTH: 1398
<212> TYPE: DNA
<213> ORGANISM: Artificial
<220> FEATURE:
<223> OTHER INFORMATION: an artificially synthesized sequence

<400> SEQUENCE: 53

| | | | | | | |
|---|---|---|---|---|---|---|
| atgagagtgc | tgattctttt | gtggctgttc | acagcctttc | ctggtatcct | gtctgatgtg | 60 |
| cagcttcagg | agtcgggacc | tggcctggtg | aaaccttctc | agtctctgtc | cctcacctgc | 120 |
| actgtcactg | gctactcaat | caccagtgat | tatgcctgga | actggatccg | gctgtttcca | 180 |
| ggaaacaaac | tggagtggat | gggcttcata | aactacagtg | gtaacactag | ctacaaccca | 240 |
| tctctcaaaa | gtcgaatctc | tatcactcga | gacacatcca | agaaccagtt | cttcctgaag | 300 |
| ttgaattctt | tgactactga | cgacacagcc | acatattact | gtgcaagagg | gggcctatcg | 360 |
| cggtttcctt | actggggcca | agggactctg | gtcaccgtct | ctgcagctag | caccaagggc | 420 |
| ccatcggtct | tccccctggc | accctcctcc | aagagcacct | ctgggggcac | agcggccctg | 480 |
| ggctgcctgg | tcaaggacta | cttccccgaa | ccggtgacgg | tgtcgtggaa | ctcaggcgcc | 540 |
| ctgaccagcg | gcgtgcacac | cttcccggct | gtcctacagt | cctcaggact | ctactccctc | 600 |
| agcagcgtgg | tgaccgtgcc | ctccagcagc | ttgggcaccc | agacctacat | ctgcaacgtg | 660 |
| aatcacaagc | ccagcaacac | caaggtggac | aagaaagttg | agcccaaatc | ttgtgacaaa | 720 |
| actcacacat | gcccaccgtg | cccagcacct | gaactcctgg | ggggaccgtc | agtcttcctc | 780 |
| ttccccccaa | aacccaagga | caccctcatg | atctcccgga | cccctgaggt | cacatgcgtg | 840 |
| gtggtggacg | tgagccacga | agaccctgag | gtcaagttca | actggtacgt | ggacggcgtg | 900 |
| gaggtgcata | atgccaagac | aaagccgcgg | gaggagcagt | acaacagcac | gtaccgtgtg | 960 |

-continued

```
gtcagcgtcc tcaccgtcct gcaccaggac tggctgaatg gcaaggagta caagtgcaag    1020
gtctccaaca aagccctccc agcccccatc gagaaaacca tctccaaagc caagggcag    1080 ccccgagaac acaggtgta caccctgccc ccatcccggg atgagctgac caagaaccag    1140
gtcagcctga cctgcctggt caaaggcttc tatcccagcg acatcgccgt ggagtgggag    1200
agcaatgggc agccggagaa caactacaag accacgcctc ccgtgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatga                                                  1398
```

<210> SEQ ID NO 54
<211> LENGTH: 465
<212> TYPE: PRT
<213> ORGANISM: Artificial
<220> FEATURE:
<223> OTHER INFORMATION: an artificially synthesized sequence

<400> SEQUENCE: 54

```
Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Thr Val Thr Gly Tyr Ser Ile Thr
            35                  40                  45

Ser Asp Tyr Ala Trp Asn Trp Ile Arg Leu Phe Pro Gly Asn Lys Leu
    50                  55                  60

Glu Trp Met Gly Phe Ile Asn Tyr Ser Gly Asn Thr Ser Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Lys Leu Asn Ser Leu Thr Thr Asp Asp Thr Ala Thr Tyr
            100                 105                 110

Tyr Cys Ala Arg Gly Gly Leu Ser Arg Phe Pro Tyr Trp Gly Gln Gly
        115                 120                 125

Thr Leu Val Thr Val Ser Ala Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
```

```
                275                 280                 285
Pro Glu Val Lys Phe Asn Trp Tyr Val Asp Gly Val Glu Val His Asn
        290                 295                 300
Ala Lys Thr Lys Pro Arg Glu Glu Gln Tyr Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Ala Leu Pro Ala Pro Ile Glu Lys
            340                 345                 350
Thr Ile Ser Lys Ala Lys Gly Gln Pro Arg Glu Pro Gln Val Tyr Thr
            355                 360                 365
Leu Pro Pro Ser Arg Asp Glu Leu Thr Lys Asn Gln Val Ser Leu Thr
    370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
    435                 440                 445
Ala Leu His Asn His Tyr Thr Gln Lys Ser Leu Ser Leu Ser Pro Gly
    450                 455                 460
Lys
465

<210> SEQ ID NO 55
<211> LENGTH: 705
<212> TYPE: DNA
<213> ORGANISM: Artificial
<220> FEATURE:
<223> OTHER INFORMATION: an artificially synthesized sequence

<400> SEQUENCE: 55
atgatgtcct ctgctcagtt ccttggtctc ctgttgctct gttttcaagg taccagatgt      60
gatatccaga tgacacagac tacatcctcc ctgtctgcct ctctgggaga cagagtcacc     120
atcagttgca ggtcaagtca ggacattaga aattatttaa actggtatca gcagaaacca     180
gatggaactg ttaaactcct gatctactat acatccagat cacactcagg agtcccctca     240
aggttcagtg gcagtgggtc tggaacagat tattctctca ccattagcaa cctggagcag     300
gaagatattg ccacttactt ttgccaacag gtaatatgt ttccgttcac gttcggaggg       360
gggaccaagc tggaaataaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gttga                    705

<210> SEQ ID NO 56
<211> LENGTH: 234
<212> TYPE: PRT
<213> ORGANISM: Artificial
<220> FEATURE:
<223> OTHER INFORMATION: an artificially synthesized sequence
```

<400> SEQUENCE: 56

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ser Ser Gln Asp
        35                  40                  45

Ile Arg Asn Tyr Leu Asn Trp Tyr Gln Gln Lys Pro Asp Gly Thr Val
50                  55                  60

Lys Leu Leu Ile Tyr Tyr Thr Ser Arg Ser His Ser Gly Val Pro Ser
65                  70                  75                  80

Arg Phe Ser Gly Ser Gly Ser Gly Thr Asp Tyr Ser Leu Thr Ile Ser
            85                  90                  95

Asn Leu Glu Gln Glu Asp Ile Ala Thr Tyr Phe Cys Gln Gln Gly Asn
            100                 105                 110

Met Phe Pro Phe Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230
```

<210> SEQ ID NO 57
<211> LENGTH: 1413
<212> TYPE: DNA
<213> ORGANISM: Artificial
<220> FEATURE:
<223> OTHER INFORMATION: an artificially synthesized sequence

<400> SEQUENCE: 57

```
atgagagtgc tgattctttt gtggctgttc acagcctttc ctggtatcct gtctgatgtg      60
cagcttcagg agtcgggacc tggcctggtg aaaccttctc agtctctgtc cctcacctgc     120
actgtcactg gctactcaat caccagtgat tatgcctgga actggatccg gctgtttcca     180
ggaaacaaac tggagtggat gggcttcata aactacagtg gtaacactag ctacaaccca     240
tctctcaaaa gtcgaatctc tatcactcga gacacatcca agaaccagtt cttcctgaag     300
ttgaattctt tgactactga cgacacagcc acatattact gtgcaagagg gggcctatcg     360
cggtttcctt actggggcca agggactctg gtcaccgtct ctgcagcgaa acaacagcc     420
ccatcggtct atccactggc ccctgtgtgt ggaggtacaa ctggctcctc ggtgactcta     480
ggatgcctgg tcaagggtta tttccctgag ccagtgacct tgacctggaa ctctggatcc     540
ctgtccagtg gtgtgcacac cttcccagct ctcctgcagt ctggcctcta caccctcagc     600
agctcagtga ctgtaaccct gaacacctgg cccagccaga ccatcacctg caatgtggcc     660
```

```
cacccggcaa gcagcaccaa agtggacaag aaaattgagc ccagagtgcc cataacacag    720
aacccctgtc ctccactcaa agagtgtccc ccatgcgcag ctccagacct cttgggtgga    780
ccatccgtct tcatcttccc tccaaagatc aaggatgtac tcatgatctc cctgagcccc    840
atggtcacat gtgtggtggt ggatgtgagc gaggatgacc cagacgtcca gatcagctgg    900
tttgtgaaca acgtggaagt acacacagct cagacacaaa cccatagaga ggattacaac    960
agtactctcc gggtggtcag tgccctcccc atccagcacc aggactggat gagtggcaag   1020
gagttcaaat gcaaggtcaa caacagagcc ctcccatccc ccatcgagaa aaccatctca   1080
aaacccagag ggccagtaag agctccacag gtatatgtct tgcctccacc agcagaagag   1140
atgactaaga aagagttcag tctgacctgc atgatcacag gcttcttacc tgccgaaatt   1200
gctgtggact ggaccagcaa tgggcgtaca gagcaaaact acaagaacac cgcaacagtc   1260
ctggactctg atggttctta cttcatgtac agcaagctca gagtacaaaa gagcacttgg   1320
gaaagaggaa gtcttttcgc ctgctcagtg gtccacgagg gtctgcacaa tcaccttacg   1380
actaagacca tctcccggtc tctgggtaaa tga                                 1413
```

<210> SEQ ID NO 58
<211> LENGTH: 470
<212> TYPE: PRT
<213> ORGANISM: Artificial
<220> FEATURE:
<223> OTHER INFORMATION: an artificially synthesized sequence

<400> SEQUENCE: 58

```
Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Ile Arg Leu Phe Pro Gly Asn Lys Leu
    50                  55                  60

Glu Trp Met Gly Phe Ile Asn Tyr Ser Gly Asn Thr Ser Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Lys Leu Asn Ser Leu Thr Thr Asp Asp Thr Ala Thr Tyr
            100                 105                 110

Tyr Cys Ala Arg Gly Gly Leu Ser Arg Phe Pro Tyr Trp Gly Gln Gly
        115                 120                 125

Thr Leu Val Thr Val Ser Ala Ala Lys Thr Thr Ala Pro Ser Val Tyr
    130                 135                 140

Pro Leu Ala Pro Val Cys Gly Thr Thr Gly Ser Ser Val Thr Leu
145                 150                 155                 160

Gly Cys Leu Val Lys Gly Tyr Phe Pro Glu Pro Val Thr Leu Thr Trp
                165                 170                 175

Asn Ser Gly Ser Leu Ser Ser Gly Val His Thr Phe Pro Ala Leu Leu
            180                 185                 190

Gln Ser Gly Leu Tyr Thr Leu Ser Ser Val Thr Val Thr Ser Asn
        195                 200                 205

Thr Trp Pro Ser Gln Thr Ile Thr Cys Asn Val Ala His Pro Ala Ser
    210                 215                 220
```

Ser Thr Lys Val Asp Lys Lys Ile Glu Pro Arg Val Pro Ile Thr Gln
225                 230                 235                 240

Asn Pro Cys Pro Pro Leu Lys Glu Cys Pro Cys Ala Ala Pro Asp
            245                 250                 255

Leu Leu Gly Gly Pro Ser Val Phe Ile Phe Pro Pro Lys Ile Lys Asp
            260                 265                 270

Val Leu Met Ile Ser Leu Ser Pro Met Val Thr Cys Val Val Val Asp
        275                 280                 285

Val Ser Glu Asp Asp Pro Asp Val Gln Ile Ser Trp Phe Val Asn Asn
        290                 295                 300

Val Glu Val His Thr Ala Gln Thr Gln Thr His Arg Glu Asp Tyr Asn
305                 310                 315                 320

Ser Thr Leu Arg Val Val Ser Ala Leu Pro Ile Gln His Gln Asp Trp
                325                 330                 335

Met Ser Gly Lys Glu Phe Lys Cys Lys Val Asn Asn Arg Ala Leu Pro
            340                 345                 350

Ser Pro Ile Glu Lys Thr Ile Ser Lys Pro Arg Gly Pro Val Arg Ala
            355                 360                 365

Pro Gln Val Tyr Val Leu Pro Pro Ala Glu Glu Met Thr Lys Lys
370                 375                 380

Glu Phe Ser Leu Thr Cys Met Ile Thr Gly Phe Leu Pro Ala Glu Ile
385                 390                 395                 400

Ala Val Asp Trp Thr Ser Asn Gly Arg Thr Glu Gln Asn Tyr Lys Asn
                405                 410                 415

Thr Ala Thr Val Leu Asp Ser Asp Gly Ser Tyr Phe Met Tyr Ser Lys
            420                 425                 430

Leu Arg Val Gln Lys Ser Thr Trp Glu Arg Gly Ser Leu Phe Ala Cys
            435                 440                 445

Ser Val Val His Glu Gly Leu His Asn His Leu Thr Thr Lys Thr Ile
        450                 455                 460

Ser Arg Ser Leu Gly Lys
465                 470

<210> SEQ ID NO 59
<211> LENGTH: 705
<212> TYPE: DNA
<213> ORGANISM: Artificial
<220> FEATURE:
<223> OTHER INFORMATION: an artificially synthesized sequence

<400> SEQUENCE: 59
atgatgtcct ctgctcagtt cctTggtctc ctgttgctct gttttcaagg taccagatgt      60
gatatccaga tgacacagac tacatcctcc ctgtctgcct ctctgggaga cagagtcacc     120
atcagttgca ggtcaagtca ggacattaga aattatttaa actggtatca gcagaaacca     180
gatggaactg ttaaactcct gatctactat acatccagat cacactcagg agtcccctca     240
aggttcagtg gcagtgggtc tggaacagat tattctctca ccattagcaa cctggagcag     300
gaagatattg ccacttactt ttgccaacag ggtaatatgt tccgttcac gttcggaggg      360 gggaccaagc tggaaataaa acgggctgat gctgcaccaa ctgtatccat cttcccacca     420
tccagtgagc agttaacatc tggaggtgcc tcagtcgtgt gcttcttgaa caacttctac     480
cccaaagaca tcaatgtcaa gtggaagatt gatggcagtg aacgacaaaa tggcgtcctg     540
aacagttgga ctgatcagga cagcaaagac agcacctaca gcatgagcag caccctcacg     600
ttgaccaagg acgagtatga acgacataac agctataccT gtgaggccac tcacaagaca     660
tcaacttcac ccattgtcaa gagcttcaac aggaatgagt gttag    705

<210> SEQ ID NO 60
<211> LENGTH: 234
<212> TYPE: PRT
<213> ORGANISM: Artificial
<220> FEATURE:
<223> OTHER INFORMATION: an artificially synthesized sequence

<400> SEQUENCE: 60

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ser Ser Gln Asp
        35                  40                  45

Ile Arg Asn Tyr Leu Asn Trp Tyr Gln Gln Lys Pro Asp Gly Thr Val
    50                  55                  60

Lys Leu Leu Ile Tyr Tyr Thr Ser Arg Ser His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Met Phe Pro Phe Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 61
<211> LENGTH: 5
<212> TYPE: PRT
<213> ORGANISM: Mus musculus

<400> SEQUENCE: 61

Asp Thr Tyr Ile Gln
1               5

<210> SEQ ID NO 62
<211> LENGTH: 17
<212> TYPE: PRT
<213> ORGANISM: Mus musculus

<400> SEQUENCE: 62

Arg Ile Asp Pro Leu Asn Gly Asn Thr Lys Tyr Val Pro Lys Phe Gln
1               5                   10                  15

Gly

<210> SEQ ID NO 63
<211> LENGTH: 7
<212> TYPE: PRT
<213> ORGANISM: Mus musculus

<400> SEQUENCE: 63

Ser Gly Thr Leu Phe Asp Phe
1               5

<210> SEQ ID NO 64
<211> LENGTH: 11
<212> TYPE: PRT
<213> ORGANISM: Mus musculus

<400> SEQUENCE: 64

Lys Ala Ser Gln Asp Ile His Lys Tyr Ile Ala
1               5                   10

<210> SEQ ID NO 65
<211> LENGTH: 7
<212> TYPE: PRT
<213> ORGANISM: Mus musculus

<400> SEQUENCE: 65

Tyr Thr Ser Thr Leu Gln Pro
1               5

<210> SEQ ID NO 66
<211> LENGTH: 8
<212> TYPE: PRT
<213> ORGANISM: Mus musculus

<400> SEQUENCE: 66

Leu Gln Tyr Asp Asn Leu Arg Thr
1               5

<210> SEQ ID NO 67
<211> LENGTH: 5
<212> TYPE: PRT
<213> ORGANISM: Mus musculus

<400> SEQUENCE: 67

Asn Tyr Trp Met Asn
1               5

<210> SEQ ID NO 68
<211> LENGTH: 17
<212> TYPE: PRT
<213> ORGANISM: Mus musculus

<400> SEQUENCE: 68

Arg Ile His Pro Ser Asp Ser Glu Thr His Tyr Asn Gln Lys Phe Lys
1               5                   10                  15

Asn

<210> SEQ ID NO 69
<211> LENGTH: 8
<212> TYPE: PRT
<213> ORGANISM: Mus musculus

<400> SEQUENCE: 69

```
Leu Tyr Tyr Tyr Thr Met Asp Tyr
1               5
```

<210> SEQ ID NO 70
<211> LENGTH: 11
<212> TYPE: PRT
<213> ORGANISM: Mus musculus

<400> SEQUENCE: 70

```
Lys Ala Ser Gln Asp Ile Asn Lys Asn Ile Ala
1               5                   10
```

<210> SEQ ID NO 71
<211> LENGTH: 7
<212> TYPE: PRT
<213> ORGANISM: Mus musculus

<400> SEQUENCE: 71

```
Tyr Thr Ser Thr Leu Gln Pro
1               5
```

<210> SEQ ID NO 72
<211> LENGTH: 9
<212> TYPE: PRT
<213> ORGANISM: Mus musculus

<400> SEQUENCE: 72

```
Leu Gln Tyr Asp Asn Leu Pro Tyr Thr
1               5
```

<210> SEQ ID NO 73
<211> LENGTH: 5
<212> TYPE: PRT
<213> ORGANISM: Mus musculus

<400> SEQUENCE: 73

```
Ser Tyr Trp Met His
1               5
```

<210> SEQ ID NO 74
<211> LENGTH: 17
<212> TYPE: PRT
<213> ORGANISM: Mus musculus

<400> SEQUENCE: 74

```
Glu Ile Asn Pro Tyr Asn Gly Gly Thr Asn Tyr Asn Glu Lys Phe Lys
1               5                   10                  15

Ser
```

<210> SEQ ID NO 75
<211> LENGTH: 6
<212> TYPE: PRT
<213> ORGANISM: Mus musculus

<400> SEQUENCE: 75

```
Trp Lys Leu Gly Thr Tyr
1               5
```

<210> SEQ ID NO 76
<211> LENGTH: 11
<212> TYPE: PRT
<213> ORGANISM: Mus musculus

<400> SEQUENCE: 76

-continued

Arg Ala Ser Gln Glu Ile Ser Gly Tyr Leu Ser
1               5                   10

<210> SEQ ID NO 77
<211> LENGTH: 7
<212> TYPE: PRT
<213> ORGANISM: Mus musculus

<400> SEQUENCE: 77

Ala Ala Ser Thr Leu Asp Ser
1               5

<210> SEQ ID NO 78
<211> LENGTH: 9
<212> TYPE: PRT
<213> ORGANISM: Mus musculus

<400> SEQUENCE: 78

Leu Gln Tyr Ala Ser Tyr Pro Arg Thr
1               5

<210> SEQ ID NO 79
<211> LENGTH: 5
<212> TYPE: PRT
<213> ORGANISM: Mus musculus

<400> SEQUENCE: 79

Val Tyr Ser Leu His
1               5

<210> SEQ ID NO 80
<211> LENGTH: 17
<212> TYPE: PRT
<213> ORGANISM: Mus musculus

<400> SEQUENCE: 80

Val Ile Ser Thr Tyr Tyr Gly Asp Ala Ile Tyr Asn Gln Lys Phe Lys
1               5                   10                  15

Gly

<210> SEQ ID NO 81
<211> LENGTH: 9
<212> TYPE: PRT
<213> ORGANISM: Mus musculus

<400> SEQUENCE: 81

Glu Gly Asn Gly Asn Pro Leu Asp Tyr
1               5

<210> SEQ ID NO 82
<211> LENGTH: 12
<212> TYPE: PRT
<213> ORGANISM: Mus musculus

<400> SEQUENCE: 82

Thr Ala Ser Ser Ser Val Ser Ser Ser Tyr Leu His
1               5                   10

<210> SEQ ID NO 83
<211> LENGTH: 7
<212> TYPE: PRT
<213> ORGANISM: Mus musculus

<400> SEQUENCE: 83

Ser Thr Ser Asn Leu Ala Ser
1               5

<210> SEQ ID NO 84
<211> LENGTH: 9
<212> TYPE: PRT
<213> ORGANISM: Mus musculus

<400> SEQUENCE: 84

His Gln Tyr His Arg Ser Pro Leu Thr
1               5

<210> SEQ ID NO 85
<211> LENGTH: 5
<212> TYPE: PRT
<213> ORGANISM: Mus musculus

<400> SEQUENCE: 85

Ser Tyr Gly Val His
1               5

<210> SEQ ID NO 86
<211> LENGTH: 16
<212> TYPE: PRT
<213> ORGANISM: Mus musculus

<400> SEQUENCE: 86

Val Ile Trp Arg Asp Gly Ser Thr Thr Tyr Asn Ser Ala Leu Lys Ser
1               5                   10                  15

<210> SEQ ID NO 87
<211> LENGTH: 8
<212> TYPE: PRT
<213> ORGANISM: Mus musculus

<400> SEQUENCE: 87

Asn Trp Asn Gly Leu Met Asp Tyr
1               5

<210> SEQ ID NO 88
<211> LENGTH: 11
<212> TYPE: PRT
<213> ORGANISM: Mus musculus

<400> SEQUENCE: 88

Arg Ala Ser Gln Asp Ile Ser Tyr Tyr Leu Asn
1               5                   10

<210> SEQ ID NO 89
<211> LENGTH: 7
<212> TYPE: PRT
<213> ORGANISM: Mus musculus

<400> SEQUENCE: 89

Tyr Thr Ser Arg Leu His Ser
1               5

<210> SEQ ID NO 90
<211> LENGTH: 9
<212> TYPE: PRT
<213> ORGANISM: Mus musculus

<400> SEQUENCE: 90

Gln Gln Gly His Thr Val Pro Trp Thr
1               5

<210> SEQ ID NO 91
<211> LENGTH: 5
<212> TYPE: PRT
<213> ORGANISM: Mus musculus

<400> SEQUENCE: 91

Ser Tyr Trp Met His
1               5

<210> SEQ ID NO 92
<211> LENGTH: 16
<212> TYPE: PRT
<213> ORGANISM: Mus musculus

<400> SEQUENCE: 92

Ala Ile Tyr Pro Gly Asn Ser Asp Ser Tyr Asn Gln Lys Phe Lys Gly
1               5                   10                  15

<210> SEQ ID NO 93
<211> LENGTH: 4
<212> TYPE: PRT
<213> ORGANISM: Mus musculus

<400> SEQUENCE: 93

Val Met Ala Tyr
1

<210> SEQ ID NO 94
<211> LENGTH: 11
<212> TYPE: PRT
<213> ORGANISM: Mus musculus

<400> SEQUENCE: 94

Arg Ala Ser Gln Asp Ile Ser Tyr Tyr Leu Asn
1               5                   10

<210> SEQ ID NO 95
<211> LENGTH: 7
<212> TYPE: PRT
<213> ORGANISM: Mus musculus

<400> SEQUENCE: 95

Ala Thr Ser Asn Leu Asp Ser
1               5

<210> SEQ ID NO 96
<211> LENGTH: 9
<212> TYPE: PRT
<213> ORGANISM: Mus musculus

<400> SEQUENCE: 96

Leu Gln Tyr Ala Ser Ser Pro Trp Thr
1               5

<210> SEQ ID NO 97
<211> LENGTH: 116
<212> TYPE: PRT
<213> ORGANISM: Mus musculus

<400> SEQUENCE: 97

Glu Asp Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

```
Tyr Ile Gln Trp Val Lys Leu Arg Pro Glu Gln Gly Leu Glu Trp Ile
             35                  40                  45

Gly Arg Ile Asp Pro Leu Asn Gly Asn Thr Lys Tyr Val Pro Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Val Arg Ser Gly Thr Leu Phe Asp Phe Trp Gly Gln Gly Thr Thr Leu
             100                 105                 110

Thr Val Ser Ser
         115
```

<210> SEQ ID NO 98
<211> LENGTH: 106
<212> TYPE: PRT
<213> ORGANISM: Mus musculus

<400> SEQUENCE: 98

```
Asp Ile Gln Met Thr Gln Ser Pro Ser Ser Leu Ser Ala Ser Leu Gly
 1               5                  10                  15

Gly Lys Val Thr Ile Thr Cys Lys Ala Ser Gln Asp Ile His Lys Tyr
             20                  25                  30

Ile Ala Trp Tyr Gln His Lys Pro Gly Lys Pro Arg Leu Leu Ile
             35                  40                  45

Gln Tyr Thr Ser Thr Leu Gln Pro Gly Ile Pro Ser Arg Phe Ser Gly
 50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asn Leu Arg Thr
                 85                  90                  95

Phe Gly Gly Gly Thr Lys Leu Glu Ile Lys
             100                 105
```

<210> SEQ ID NO 99
<211> LENGTH: 117
<212> TYPE: PRT
<213> ORGANISM: Mus musculus

<400> SEQUENCE: 99

```
Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Asn Tyr
             20                  25                  30

Trp Met Asn Trp Val Lys Gln Arg Pro Gly Arg Gly Leu Glu Trp Ile
             35                  40                  45

Gly Arg Ile His Pro Ser Asp Ser Glu Thr His Tyr Asn Gln Lys Phe
 50                  55                  60

Lys Asn Lys Ala Thr Leu Thr Val Asp Lys Ser Ser Thr Ala Tyr
 65                  70                  75                  80

Ile Gln Leu Ser Ser Leu Thr Ser Glu Asp Ser Ala Val Tyr Tyr Cys
                 85                  90                  95

Ala Asn Leu Tyr Tyr Tyr Thr Met Asp Tyr Trp Gly Gln Gly Thr Ser
             100                 105                 110

Val Thr Val Ser Ser
         115
```

-continued

<210> SEQ ID NO 100
<211> LENGTH: 107
<212> TYPE: PRT
<213> ORGANISM: Mus musculus

<400> SEQUENCE: 100

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Asn
            20                  25                  30

Ile Ala Trp His Gln His Lys Pro Gly Lys Gly Pro Arg Leu Leu Ile
        35                  40                  45

Trp Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Pro Tyr
                85                  90                  95

Thr Phe Gly Ser Gly Thr Lys Leu Glu Ile Lys
            100                 105
```

<210> SEQ ID NO 101
<211> LENGTH: 115
<212> TYPE: PRT
<213> ORGANISM: Mus musculus

<400> SEQUENCE: 101

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Tyr Asn Gly Gly Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ile Trp Lys Leu Gly Thr Tyr Trp Gly Gln Gly Thr Leu Val Thr
            100                 105                 110

Val Ser Ala
        115
```

<210> SEQ ID NO 102
<211> LENGTH: 107
<212> TYPE: PRT
<213> ORGANISM: Mus musculus

<400> SEQUENCE: 102

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60
```

```
Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Ser Tyr Pro Arg
                 85                  90                  95

Thr Phe Gly Gly Gly Thr Lys Leu Glu Ile Lys
            100                 105
```

<210> SEQ ID NO 103
<211> LENGTH: 118
<212> TYPE: PRT
<213> ORGANISM: Mus musculus

<400> SEQUENCE: 103

```
Gln Val Gln Leu Gln Gln Ser Gly Ala Glu Leu Val Arg Pro Gly Val
 1               5                  10                  15

Ser Val Lys Ile Ser Cys Lys Gly Ser Gly Tyr Thr Phe Thr Val Tyr
                20                  25                  30

Ser Leu His Trp Val Lys Gln Ser His Ala Arg Ser Leu Glu Trp Ile
            35                  40                  45

Gly Val Ile Ser Thr Tyr Tyr Gly Asp Ala Ile Tyr Asn Gln Lys Phe
 50                  55                  60

Lys Gly Lys Ala Thr Met Thr Val Asp Lys Ser Ser Thr Ala Tyr
 65                  70                  75                  80

Met Glu Leu Ala Arg Leu Thr Ser Glu Asp Ser Ala Ile Tyr Tyr Cys
                 85                  90                  95

Ala Arg Glu Gly Asn Gly Asn Pro Leu Asp Tyr Trp Gly Gln Gly Thr
            100                 105                 110

Thr Leu Thr Val Ser Ser
            115
```

<210> SEQ ID NO 104
<211> LENGTH: 108
<212> TYPE: PRT
<213> ORGANISM: Mus musculus

<400> SEQUENCE: 104

```
Gln Ile Val Leu Thr Gln Ser Pro Ala Ile Met Ser Ala Ser Leu Gly
 1               5                  10                  15

Glu Arg Val Thr Met Thr Cys Thr Ala Ser Ser Ser Val Ser Ser Ser
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Thr Asn Met Glu
 65                  70                  75                  80

Ala Glu Asp Ser Ala Thr Tyr Tyr Cys His Gln Tyr His Arg Ser Pro
                 85                  90                  95

Leu Thr Phe Gly Ala Gly Thr Lys Leu Glu Leu Lys
            100                 105
```

<210> SEQ ID NO 105
<211> LENGTH: 116
<212> TYPE: PRT
<213> ORGANISM: Mus musculus

```
<400> SEQUENCE: 105

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Gly Val His Trp Val Arg Gln Pro Pro Gly Lys Gly Leu Glu Trp Leu
        35                  40                  45

Gly Val Ile Trp Arg Asp Gly Ser Thr Thr Tyr Asn Ser Ala Leu Lys
    50                  55                  60

Ser Arg Leu Ser Ile Ser Lys Asp Gly Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asn Trp Asn Gly Leu Met Asp Tyr Trp Gly Gln Gly Thr Ser Val
            100                 105                 110

Thr Val Ser Ser
            115

<210> SEQ ID NO 106
<211> LENGTH: 107
<212> TYPE: PRT
<213> ORGANISM: Mus musculus

<400> SEQUENCE: 106

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Tyr Tyr
            20                  25                  30

Leu Asn Trp Tyr Gln Gln Arg Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Glu Ser Ser Leu Thr Ile Ser Asn Leu Glu Gln
65                  70                  75                  80

Glu Asp Ile Ala Thr Tyr Phe Cys Gln Gln Gly His Thr Val Pro Trp
                85                  90                  95

Thr Phe Gly Gly Gly Thr Lys Leu Glu Ile Lys
            100                 105

<210> SEQ ID NO 107
<211> LENGTH: 112
<212> TYPE: PRT
<213> ORGANISM: Mus musculus

<400> SEQUENCE: 107

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Ser Tyr Asn Gln Lys Phe Lys
    50                  55                  60

Gly Lys Ala Lys Leu Thr Ala Val Thr Ser Thr Ser Thr Ala Tyr Met
65                  70                  75                  80
```

```
Glu Leu Ser Ser Leu Thr Asn Glu Asp Ser Ala Val Tyr Tyr Cys Thr
                85                  90                  95
Ser Val Met Ala Tyr Trp Gly Gln Gly Thr Ser Val Thr Val Ser Ser
            100                 105                 110

<210> SEQ ID NO 108
<211> LENGTH: 107
<212> TYPE: PRT
<213> ORGANISM: Mus musculus

<400> SEQUENCE: 108

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Asn Ser
            20                  25                  30

Leu Asn Trp Leu Gln Gln Glu Pro Asp Gly Thr Ile Lys Arg Leu Ile
        35                  40                  45

Tyr Ala Thr Ser Asn Leu Asp Ser Gly Val Ser Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Ser Pro Trp
                85                  90                  95

Thr Phe Gly Gly Gly Thr Lys Leu Glu Ile Lys
            100                 105
```